US012370197B2

(12) United States Patent
Yang et al.

(10) Patent No.: US 12,370,197 B2
(45) Date of Patent: Jul. 29, 2025

(54) COMBINATION PRODUCT OF A BCL-2/BCL-XL INHIBITOR AND A CHEMOTHERAPEUTIC AGENT AND USE THEREOF IN THE PREVENTION AND/OR TREATMENT OF DISEASES

(71) Applicants: ASCENTAGE PHARMA (SUZHOU) CO., LTD., Suzhou (CN); ASCENTAGE PHARMA GROUP CORP LIMITED, Hong Kong (CN)

(72) Inventors: Dajun Yang, Suzhou (CN); Yifan Zhai, Suzhou (CN); Douglas Dong Fang, Suzhou (CN); Qiuqiong Tang, Suzhou (CN)

(73) Assignees: ASCENTAGE PHARMA (SUZHOU) CO., LTD., Jiangsu (CN); ASCENTAGE PHARMA GROUP CORP LIMITED, Hong Kong (CN)

( * ) Notice: Subject to any disclaimer, the term of this patent is extended or adjusted under 35 U.S.C. 154(b) by 260 days.

(21) Appl. No.: 17/282,024

(22) PCT Filed: Jul. 30, 2020

(86) PCT No.: PCT/CN2020/105810
§ 371 (c)(1),
(2) Date: Apr. 1, 2021

(87) PCT Pub. No.: WO2021/018240
PCT Pub. Date: Feb. 4, 2021

(65) Prior Publication Data
US 2022/0143039 A1    May 12, 2022

(30) Foreign Application Priority Data

Jul. 31, 2019 (WO) ................ PCT/CN2019/098625
Jul. 3, 2020 (CN) ......................... 202010631089.7

(51) Int. Cl.
| | |
|---|---|
| A61K 31/55 | (2006.01) |
| A61K 31/496 | (2006.01) |
| A61K 31/635 | (2006.01) |
| A61K 31/675 | (2006.01) |
| A61K 45/06 | (2006.01) |
| A61P 35/02 | (2006.01) |

(52) U.S. Cl.
CPC ............ *A61K 31/55* (2013.01); *A61K 31/496* (2013.01); *A61K 31/635* (2013.01); *A61K 31/675* (2013.01); *A61K 45/06* (2013.01); *A61P 35/02* (2018.01)

(58) Field of Classification Search
CPC ........ A61P 35/02; A61K 31/55; A61K 31/496
See application file for complete search history.

(56) References Cited

FOREIGN PATENT DOCUMENTS

| CN | 102976924 B | 9/2014 | | |
|---|---|---|---|---|
| WO | WO-2014113413 A1 * | 7/2014 | ........... | A61K 31/496 |
| WO | 2016024230 A1 | 2/2016 | | |

(Continued)

OTHER PUBLICATIONS

Kuroda J. et al. "ABT-737 is a useful component of combinatory chemotherapies for chronic myeloid leukaemias with diverse drug-resistance mechanisms;" 2007, British Journal of Haematology, 140, pp. 181-190 (Year: 2007).*

(Continued)

*Primary Examiner* — Brenda L Coleman
*Assistant Examiner* — Madeline E Braun
(74) *Attorney, Agent, or Firm* — Barnes & Thornburg LLP

(57) ABSTRACT

Provided herein is a combination product comprising a Bcl-2/Bcl-xL inhibitor and a chemotherapeutic agent, in particular a Bcl-2/Bcl-xL inhibitor of formula (I-A) and homoharringtonine or an active derivative thereof, in free or pharmaceutically acceptable salt or solvate form. Provided herein is also the use of the aforementioned combination for the preparation of a medicament for the prevention and/or treatment of cancer, in particular of hematological malignancies, and to a method for the prevention and/or treatment of cancer, in particular of hematological malignancies, using the aforementioned combination.

8 Claims, 7 Drawing Sheets

(56) References Cited

FOREIGN PATENT DOCUMENTS

WO    WO-2018027097 A1 *  2/2018  .......... A61K 31/437
WO       2020024976 A1     2/2020

OTHER PUBLICATIONS

Dinavahi et al. "Moving Synergistically Acting Drug Combinations to the Clinic by Comparing Sequential versus Simultaneous Drug Administrations", 2018, Molecular Pharmacology, 93, pp. 190-196 (Year: 2018).*

Oltersdorf et al., "An inhibitor of Bcl-2 family proteins induces regression of solid tumors", 2005, Nature, 435, pp. 677-681 (Year: 2005).*

International Search Report from PCT/CN2020/105810, dated Nov. 4, 2020.

International Preliminary Report from PCT/CN2020/105810, dated Feb. 1, 2022.

Kuroda J. et al. "ABT-737 is a useful component of combinatory chemotherapies for chronic myeloid leukaemias wifh diverse drug-resistance mechanisms;" British Journal of Haematology; , vol. 140, Nov. 20, 2007 (Nov. 20, 2007), pp. 181-190.

Adams, Jerry M. and Cory, Suzanne, The Bcl-2 Protein Family: Arbiters of Cell Survival; Science, vol. 281, (Aug. 1998); pp. 1322-1326.

Chao, Debra T. and Korsmeyer, Stanley J., "BCL-2 Family: Regulators of Cell Death," Annual Review of Immunology, (1998), 16; pp. 395-419.

Kin Tam, "Estimating the "First in human" dose—a revisit with particular emphasis on oncology drugs," ADMET & DMPK 1(4), (Dec. 2013), pp. 63-75.

Minn, A.J. et al., "Recent Progress on the Regulation of Apoptosis by Bcl-2 Family Members," Advances in Immunology (1998); 70; pp. 245-279.

Pan et al., "Synthetic Lethality of Combined Bcl-2 Inhibition and p53 Activation in AML: Mechanisms and Superior Antileukemic Efficacy," Cancer Cell, 32(6), (Dec. 2017), pp. 748-760.

Reed et al., "BCL-2 Family Proteins: Regulators of Cell Death Involved in the Pathogenesis of Cancer and Resistance to Therapy," Journal of Cellular Biochemistry, (1996) 60: pp. 23-32.

Reed, John C., "Bcl-2 Family Proteins: Strategies for Overcoming Chemoresistance in Cancer," Advances in Pharmacology, (1997), vol. 41, pp. 501-553.

Wei, et al., "Homoharringtonine is synergistically lethal with BCL-2 inhibitor APG-2575 in acute myeloid leukemia," Journal of Translational Medicine (2022) 20:299, https://doi.org/10.1186/s12967-022-03497-2.

* cited by examiner

C

D

A

B

A

B

COMBINATION PRODUCT OF A BCL-2/BCL-XL INHIBITOR AND A CHEMOTHERAPEUTIC AGENT AND USE THEREOF IN THE PREVENTION AND/OR TREATMENT OF DISEASES

CROSS REFERENCE TO RELATED APPLICATIONS

This application is a national phase of International Patent Application No. PCT/CN2020/105810, filed Jul. 30, 2020, which claims priority to International Patent Application No. PCT/CN2019/098625, filed Jul. 31, 2019 and Chinese Patent Application No. 202010631089.7, filed Jul. 3, 2020, all of which are incorporated by reference herein in their entirety.

TECHNICAL FIELD

The invention belongs to the technical field of medicines, and particularly relates to a combination product comprising a Bcl-2/Bcl-xL inhibitor and a chemotherapeutic drug and use thereof in preventing, delaying the progression of and/or treating cancers, particularly hematological malignancies.

BACKGROUND

Apoptosis, also known as programmed cell death, is a precisely controlled cell death mechanism in organisms. It can orderly eliminate unnecessary or damaged cells in vivo, and has important effects on embryonic development and cell homeostasis maintenance.

The Bcl-2 protein family related to the apoptosis function is considered to play an important role in the apoptosis regulation process, and the protein family members can be divided into two subfamilies according to the structure and the function, namely, an anti-apoptosis protein family such as Bcl-2, Bcl-xl, Mcl-1 and the like, and a pro-apoptosis protein family such as Bak, Bax, Bim, Bid, Noxa, Puma and the like.

The anti-apoptosis proteins such as Bcl-2, Bcl-xl, Mcl-1 and the like are involved in the apoptosis, differentiation and cell cycle regulation of cells, and can inhibit cell death. The over-expression of the anti-apoptosis proteins then can cause the over-proliferation of cells, further cause cancers or malignant tumors, and are closely related to the generation of tumor drug resistance. Studies have shown that anti-apoptotic proteins are indeed overexpressed in many cancer types, and one of the major manners by which cancer cells avoid apoptosis is by upregulating anti-apoptotic Bcl-2 family proteins. These over-expressions are associated with poor prognosis in several types of cancer, as well as clinical resistance to chemotherapeutic agents and radiation. Consistent with clinical observations, laboratory studies have established that overexpression of Bcl-2 or Bcl-xL in vitro and in vivo causes cancer cells to become more resistant to chemotherapy (D. T. Chao et al, Annu Rev Immunol 1998; 16; 395-419; J. C. Reed et al, Advances in Pharmacology 1997; 41; 501-553; J. C. Reed et al, J Cell Biochem 1996; 60: 23-32; A. J. Minn et at, Advances in Immunology 1998; 70; 245-279; J. M. Adams et at, Science 1998; 281; 1322).

Therefore, targeting anti-apoptotic proteins Bel-2 and the like has been used as a strategy for treating cancers, and inhibiting the Bcl-2 activity of cancer cells can increase cancer cell death and reduce chemotherapy resistance. For example, overexpression of anti-apoptotic Bcl-2 family proteins is a common cause of chemotherapy resistance and poor prognosis in hematological malignancies such as Acute Myeloid Leukemia (AML) patients, and preclinical studies have shown that the BCL-2 inhibitor Venetoclax sensitizes Acute Myeloid Leukemia (AML) by causing apoptosis (Pan, R., et at (2017) "Synthetic Lethality of Combined Bcl-2 Inhibition and p53 Activation in AML: Mechanisms and Superior Antileukemic Efficacy", Cancer Cell 32(6): 748-760 e746). Therefore, inhibition of anti-apoptotic Bcl-2 family proteins is an effective strategy for the treatment of cancers such as hematological malignancies, e.g., AML or myelodysplastic syndrome.

The anti-apoptotic protein members Bcl-2, Bcl-xL, Mcl-1, etc. inhibit apoptosis by heterodimerization with pro-apoptotic proteins such as Bak, Bax, Bim, Bid, etc. Therefore, inhibitors blocking heterodimerization between the two may act as antagonists for the anti-apoptotic proteins Bcl-2 and the like, with therapeutic potential for human cancers in which the anti-apoptotic proteins are overexpressed (WO2018027097A1).

The protein translation elongation inhibitor homoharringtonine has been included in Chinese Pharmacopoeia since 1990, and is used for clinically treating various hematological diseases such as acute non-lymphocytic leukemia and chronic lymphoma (CN102976924B), and has been approved for treating chronic granulocytic leukemia in the United states.

With the progress of the molecular biology, molecular targeted therapy has become a hot spot for medical, especially tumor researches. The biological behavior of most tumors is not dominated by a single signaling pathway, but multiple signaling pathways work together. In some cases, drugs with different mechanisms of action may be used in combination. However, it is not necessary that any combination of drugs with different mechanisms of action but acting in similar fields may produce a combination with beneficial effects. Therefore, although there is a need in the art for a combination regimen and product directing to different target proteins and/or different signal transduction pathways, it remains a challenge in the medical field to find a combination regimen and product that is feasible and can bring about a more superior effect (reduced dosage of a single drug, reduced toxic side effects of a single drug, and/or acting in a synergistic manner, etc.) compared to a single drug, in view of the complexity of the tumorigenesis mechanism, the unpredictability of the interaction between different drugs, etc. Meanwhile, in the practice of cancer treatment, the generation of drug resistance of tumor cells to single-target drugs is also a difficult problem to be overcome.

Upon long-term and extensive studies, the inventors have surprisingly found that the combination product comprising a Bel-2/Bcl-xL inhibitor and a chemotherapeutic agent, as defined in the specification, in particular in the claims, is capable of providing a prophylactic and/or therapeutic effect on cancers, in particular hematological malignancies, in a synergistic manner. Especially, the combination of the two may exert prophylactic and/or therapeutic effects in a synergistic manner on drug-resistant hematological malignancies such as AML or myelodysplastic syndrome, thereby providing a more effective treatment for the diseases.

DISCLOSURE OF INVENTION

The invention provides a combination product comprising a Bcl-2/Bcl-xL inhibitor and a chemotherapeutic drug and use thereof in preventing and/or treating cancers.

In particular, the first aspect of the present invention relates to a combination product comprising a Bcl-2/Bcl-xL inhibitor and a chemotherapeutic agent, wherein the inhibitor is a compound of formula I-A:

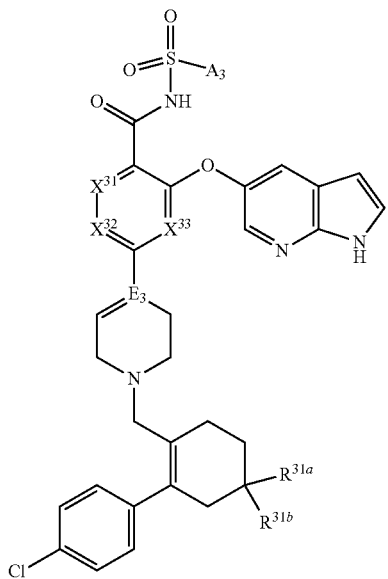

(I-A)

wherein:

$A_3$ is selected from the group consisting of

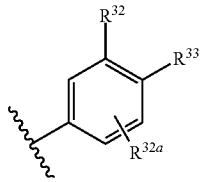

A-1

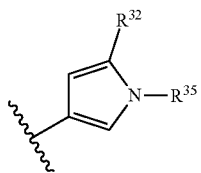

A-2

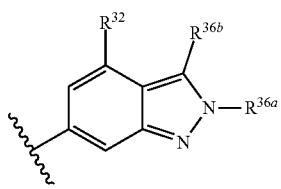

A-3

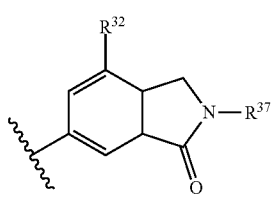

A-4

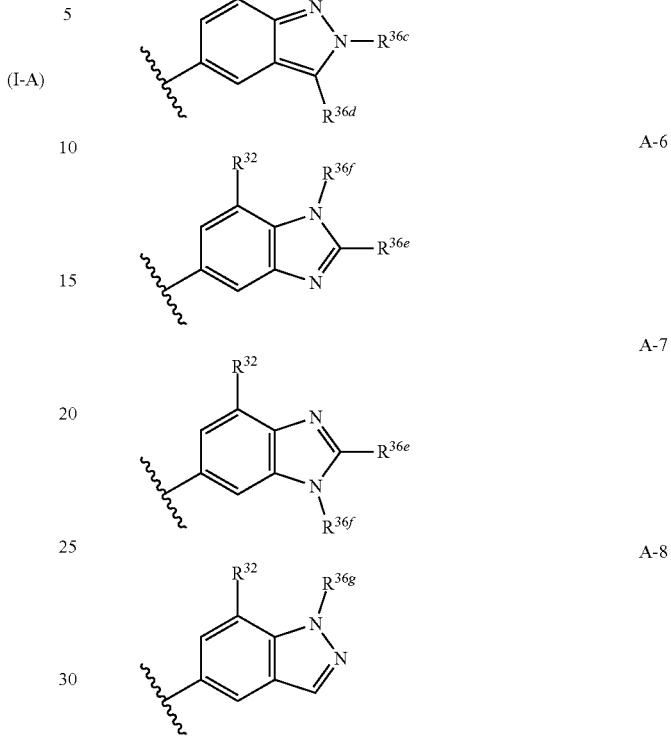

A-5

A-6

A-7

A-8

A-9

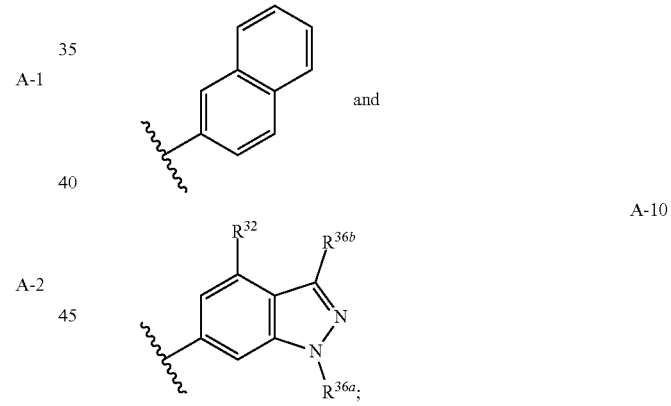

and

A-10

$E_3$ is a C atom and === is a double bond;
or $E_3$ is —C(H)— and === is a single bond;
or $E_3$ is a N atom and === is a single bond;
$X^{31}$, $X^{32}$, and $X^{33}$ are each independently —$CR^{38}$= or —N=;
$R^{31a}$ and $R^{31b}$ taken together with the C atom to which they are attached form 3-, 4-, or 5-membered optionally substituted cycloalkyl; or
$R^{31a}$ and $R^{31b}$ taken together with the C atom to which they are attached form a 4- or 5-membered optionally substituted heterocyclic ring;
$R^{32}$ is —$NO_2$, —$SO_2CH_3$, or —$SO_2CF_3$;
$R^{32a}$ is H or X;
$R^{33}$ is H, —CN, —C≡CH, or —$N(R^{34a})(R^{34b})$;
$R^{34a}$ is optionally substituted $C_{1-6}$alkyl, optionally substituted $C_{3-6}$cycloalkyl, heterocycle, heteroalkyl, (cycloalkyl)alkyl or heterocycloalkyl;

$R^{34b}$ is H or $C_{1-4}$alkyl;

$R^{35}$ is optionally substituted $C_{1-6}$alkyl, heterocycle, heteroalkyl, (cycloalkyl)alkyl or heterocycloalkyl;

$R^{36a}$, $R^{36c}$, $R^{36e}$, $R^{36f}$ and $R^{36g}$ are each independently H, optionally substituted $C_{1-6}$ alkyl, optionally substituted $C_{3-6}$cycloalkyl, optionally substituted aryl, optionally substituted heteroaryl, heterocycle, heteroalkyl, (cycloalkyl)alkyl, or heterocycloalkyl;

$R^{36b}$ and $R^{36d}$ are each independently H, $C_{1-4}$alkyl or halogen;

$R^{37}$ is optionally substituted $C_{1-6}$alkyl, heterocycle, heteroalkyl, (cycloalkyl)alkyl, or heterocycloalkyl;

$R^{38}$ is H or halogen.

In some embodiments, the inhibitor is selected from the group consisting of the compounds shown in Table 1 and Tables 1A-1C of the present specification, in particular the following compounds or pharmaceutically acceptable salts or solvates thereof:

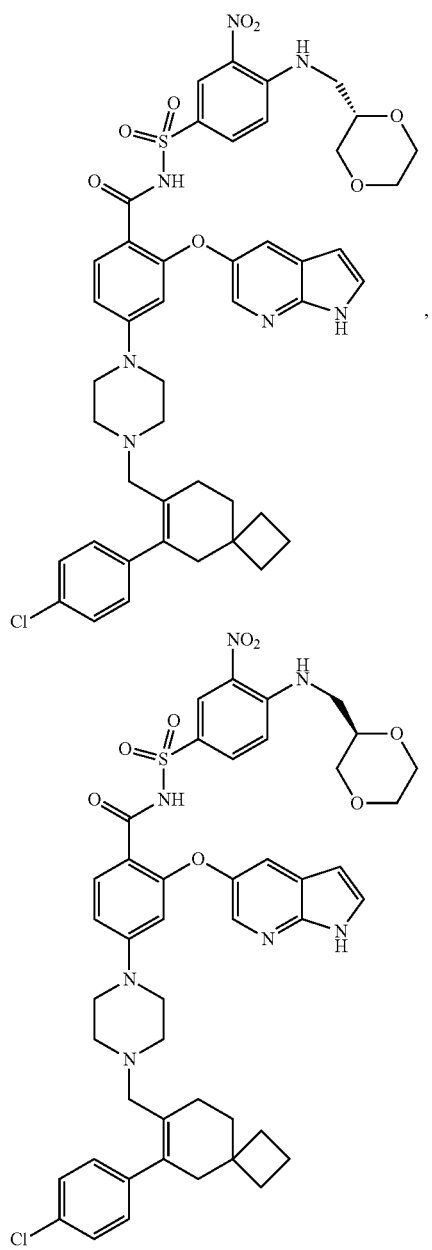

and

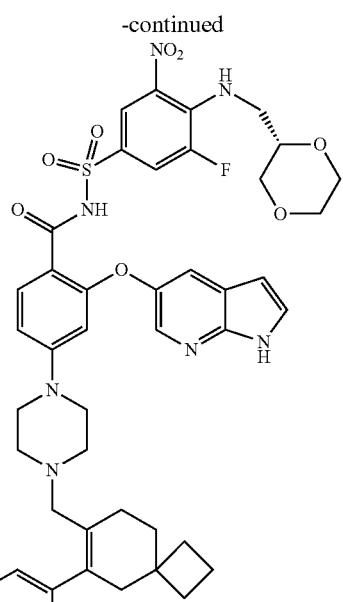

In some embodiments, the inhibitor in the combination product is the following compound or a pharmaceutically acceptable salt or solvate thereof:

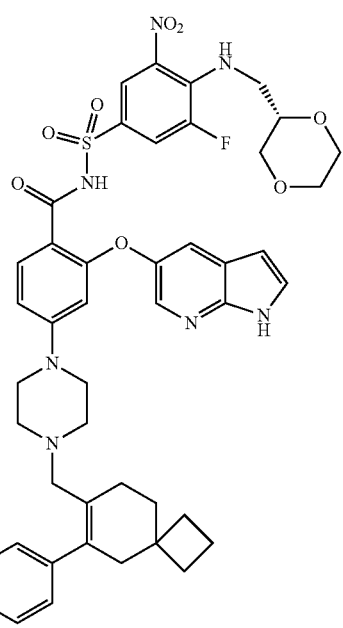

In some embodiments, the Bcl-2/Bcl-xL inhibitor is a compound having the formula (I), (II), (III), or (IV):

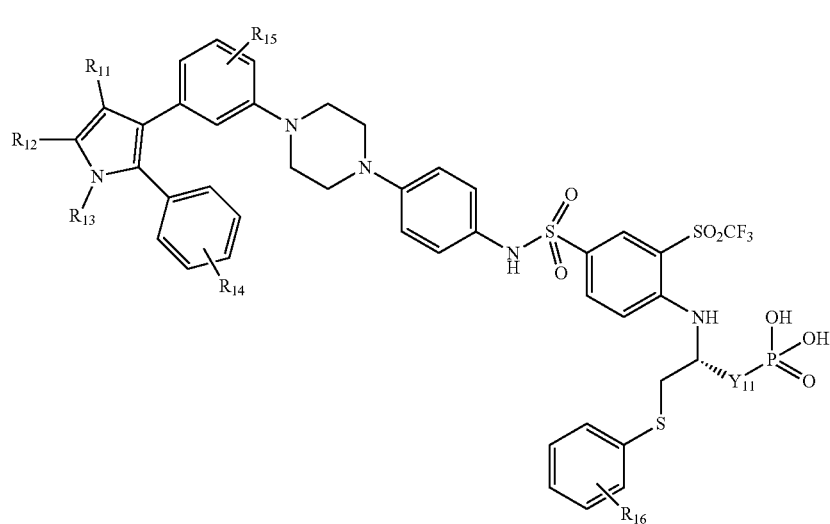
(I)
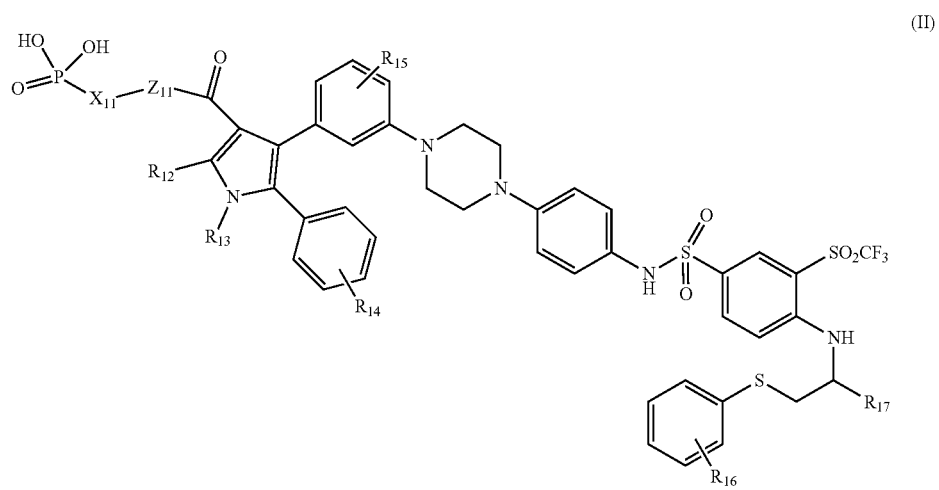
(II)
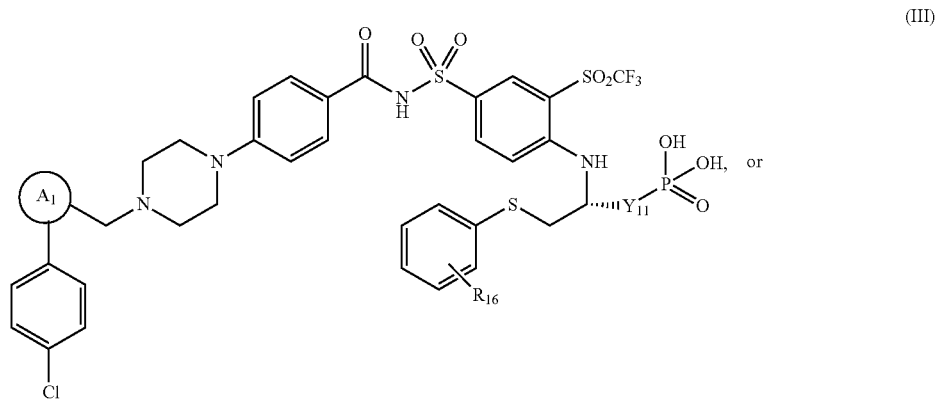
(III)

-continued (IV)

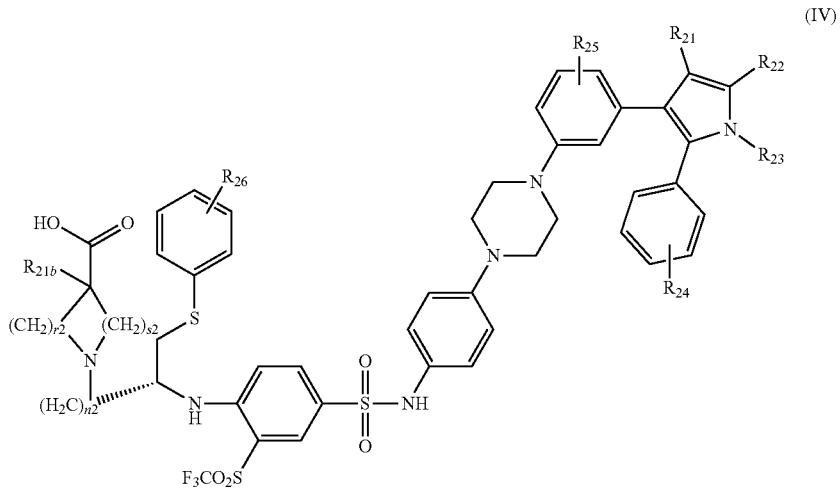

wherein the ring $A_1$ is

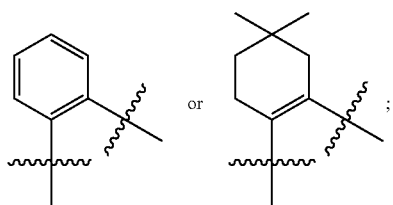

Substituted or unsubstituted $X_{11}$ is selected from the group consisting of alkylene, alkenylene, cycloalkylene, cycloalkenylene, and heterocycloalkylene;

$Y_{11}$ is selected from the group consisting of $(CH_2)_nN(R_{11}{}^a)$ and

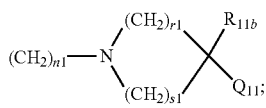

$Q_{11}$ is selected from the group consisting of O, $O(CH_2)_{1-3}$, $NR_{11}{}^c$, $NR_{11}{}^c(C_{1-3}alkylene)$, $OC(=O)(C_{1-3}alkylene)$, $C(=O)O$, $C(=O)O(C_{1-3}alkylene)$, $NHC(=O)(C_{1-3}alkylene)$, $C(=O)NH$ and $C(=O)NH(C_{1-3}alkylene)$;

$Z_{11}$ is O or $NR_{11}{}^c$;

$R_{11}$ and $R_{12}$ are independently selected from the group consisting of H, CN, $NO_2$, halogen, alkyl, cycloalkyl, alkenyl, cycloalkenyl, alkynyl, aryl, heteroaryl, heterocycloalkyl, $OR_1'$, $SR_1'$, $NR_1'R_1''$, $COR_1'$, $CO_2R_1'$, $OCOR_1'$, $CONR_1'R_1''$, $CONR_1'SO_2R_1''$, $NR_1'COR_1''$, $NR_1'CONR_1''R_1'''$, $NR_1'C=SNR_1''R_1'''$, $NR_1'SO_2R_1''$, $SO_2R_1'$ and $SO_2NR_1'R_1''$;

$R_{13}$ is selected from the group consisting of H, alkyl, cycloalkyl, alkenyl, cycloalkenyl, alkynyl, aryl, heteroaryl, heterocycloalkyl, $OR_1'$, $NR_1'R_1''$, $OCOR_1'$, $CO_2R_1'$, $COR_1'$, $CONR_1'R_1''$, $CONR_1'SO_2R_1''$, $C_{1-3}$alkyleneCH(OH)CH$_2$OH, $SO_2R_1'$ and $SO_2NR_1'R_1''$;

$R_1'$, $R_1''$ and $R_1'''$ are each independently H, alkyl, cycloalkyl, alkenyl, cycloalkenyl, alkynyl, aryl, heteroaryl, $C_{1-3}$alkyleneheterocycloalkyl or heterocycloalkyl;

$R_1'$ and $R_1''$ or $R_1''$ and $R_1'''$ may together with the atoms to which they are attached form a 3-7 membered ring;

$R_{14}$ is hydrogen, halogen, $C_{1-3}$alkyl, $CF_3$ or CN;

$R_{15}$ is hydrogen, halogen, $C_{1-3}$alkyl, substituted $C_{1-3}$alkyl, hydroxyalkyl, alkoxy or substituted alkoxy;

$R_{16}$ is selected from the group consisting of H, CN, $NO_2$, halogen, alkyl, cycloalkyl, alkenyl, cycloalkenyl, alkynyl, aryl, heteroaryl, heterocycloalkyl, $OR_1'$, $SR_1'$, $NR_1'R_1''$, $CO_2R_1'$, $OCOR_1'$, $CONR_1'R_1''$, $CONR_1'SO_2R_1''$, $NR_1'COR_1''$, $NR_1'CONR_1''R_1'''$, $NR_1'C=SNR_1''R_1'''$, $NR_1'SO_2R_1''$, $SO_2R_1'$ and $SO_2NR_1'R_1''$;

Substituted or unsubstituted $R_{17}$ is selected from the group consisting of hydrogen, alkyl, alkenyl, $(CH_2)_{0-3}$-cycloalkyl, $(CH_2)_{0-3}$-cycloalkenyl, $(CH_2)_{0-3}$-heterocycloalkyl, $(CH_2)_{0-3}$aryl, and $(CH_2)_{0-3}$heteroaryl;

$R_{18}$ is selected from the group consisting of hydrogen, halogen, $NO_2$, CN, $CF_3SO_2$, and $CF_3$;

$R_{11}{}^a$ is selected from the group consisting of hydrogen, alkyl, heteroalkyl, alkenyl, hydroxyalkyl, alkoxy, substituted alkoxy, cycloalkyl, cycloalkenyl and heterocycloalkyl;

$R_{11}{}^b$ is hydrogen or alkyl;

$R_{11}{}^c$ is selected from the group consisting of hydrogen, alkyl, substituted alkyl, hydroxyalkyl, alkoxy, and substituted alkoxy; and $n_1$, $r_1$ and $s_1$ are each independently 1, 2, 3, 4, 5 or 6;

$R_{21}$ is $SO_2R_2'$;

$R_{22}$ is alkyl, preferably $C_{1-4}$alkyl, more preferably methyl, propyl or isopropyl;

$R_{23}$ is alkyl, preferably $C_{1-4}$alkyl, more preferably methyl, propyl or isopropyl;

$R_{24}$ is halogen, preferably fluorine, chlorine;

$R_{25}$ is halogen, preferably fluorine, chlorine;

$R_{26}$ is selected from the group consisting of H, halogen and alkyl, preferably fluoro, chloro, $C_{1-4}$alkyl, more preferably methyl, propyl or isopropyl;

$R_{21b}$ is H or alkyl, preferably $C_{1-4}$alkyl, more preferably methyl, propyl or isopropyl;

$n_2$, $r_2$ and $s_2$ are each independently 1, 2, 3, 4, 5 or 6, more preferably $r_2$ and $s_2$ are both 2 and $n_2$ is 3, 4 or 5, more preferably $n_2$, $r_2$ and $s_2$ are all 2; and $R_2'$ is alkyl, preferably $C_{1-4}$alkyl, more preferably methyl, propyl or isopropyl.

In some embodiments, the Bcl-2/Bcl-xL inhibitor is selected from the compounds of Table 2 of the specification. In some embodiments, the Bcl-2/Bcl-xL inhibitor is selected from Compound 81 and Compound 97.

In some embodiments, the chemotherapeutic agent is selected from one or more of actinomycin, all-trans retinoic acid, azacitidine, azathioprine, bleomycin, bortezomib, carboplatin, capecitabine, cisplatin, chlorambucil, cyclophosphamide, cytarabine, daunorubicin, doxifluridine, doxorubicin, epirubicin, valrubicin, adriamycin, epothilone, fluorouracil, gemcitabine, hydroxyurea, idarubicin, imatinib, irinotecan, mechlorethamine, mercaptopurine, methotrexate, mitoxantrone, oxaliplatin, paclitaxel, docetaxel, pemetrexed, teniposide, etoposide, thioguanine, topotecan, vemurafenib, vinblastine, vincristine, vindesine, vinorelbine, camptothecin, or hydroxycamptothecine.

In some embodiments, the chemotherapeutic agent is selected from cephalotaxine alkaloids or active derivatives thereof, including but not limited to cephalotaxine, harringtonine, isoharringtonine, homoharringtonine, deoxyharringtonine, homodeoxyharringtonine, drupacine (CAS No. 49686-57-9), demethylcephalotaxinone (CAS No. 51020-45-2), 11-hydroxycephalotaxine, or epiwilsonine (CAS No. 39024-15-2).

In some embodiments, the chemotherapeutic agent is homoharringtonine (HHT).

In some embodiments, the combination product of the invention comprises an inhibitor selected from the group consisting of,

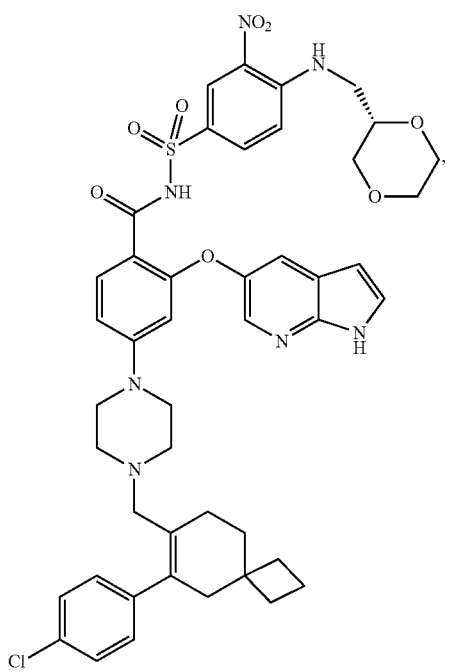

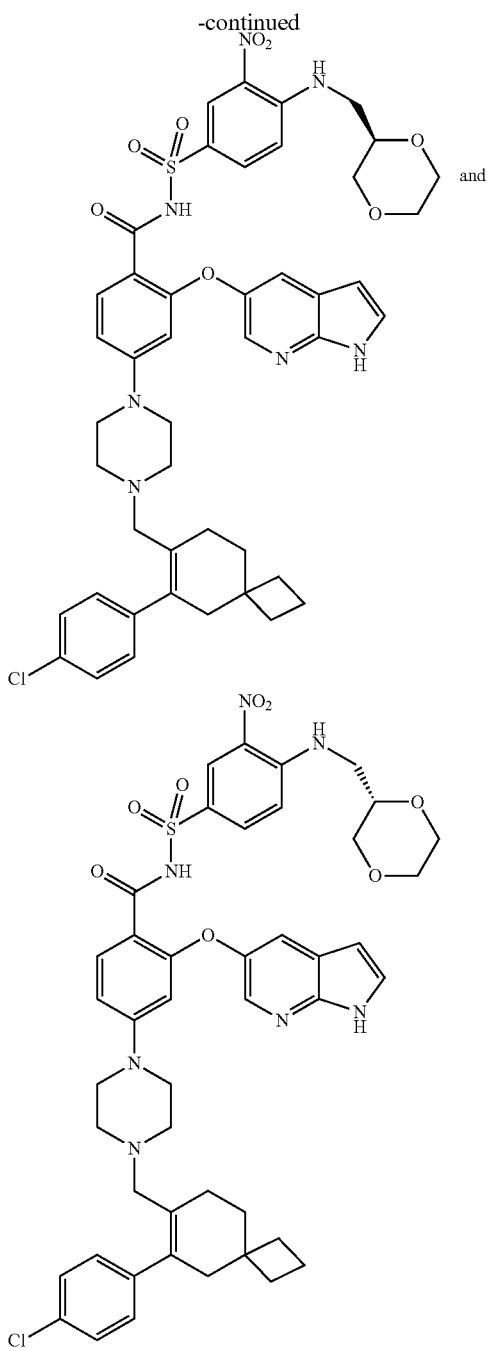

and homoharringtonine.

In some embodiments, the combination product is in the form of a pharmaceutical composition.

In some embodiments, the Bcl-2/Bcl-xL inhibitor and the chemotherapeutic agent are each in separate formulations.

In some embodiments, the Bcl-2/Bcl-xL inhibitor and the chemotherapeutic agent are administered simultaneously or sequentially.

In some embodiments, the combination product further comprises a pharmaceutically acceptable carrier, diluent or excipient.

In some embodiments, the combination product is in the form of a tablet, capsule, granule, syrup, powder, lozenge, sachet, cachet, elixir, suspension, emulsion, solution, syrup, aerosol, ointment, cream, and injection.

The second aspect of the present invention relates to the use of a Bcl-2/Bcl-xL inhibitor in combination with a chemotherapeutic agent in the manufacture of a medicament for the prevention and/or treatment of cancer, in particular the Bcl-2/Bcl-xL inhibitor in combination with the chemotherapeutic agent of the first aspect above in the manufacture of a medicament for the prevention and/or treatment of cancer.

The third aspect of the present invention relates to a combination product comprising a Bel-2/Bcl-xL inhibitor and a chemotherapeutic agent, in particular a Bcl-2/Bcl-xL inhibitor and a chemotherapeutic agent as described above in the first aspect, for use in the prevention and/or treatment of cancer.

The fourth aspect of the present invention relates to a method for the prevention and/or treatment of cancer comprising administering to a patient in need thereof a jointly effective amount of a Bcl-2/Bcl-xL inhibitor in combination with a chemotherapeutic, particularly a Bcl-2/Bcl-xL inhibitor in combination with a chemotherapeutic as described above in the first aspect.

For the various aspects of the invention, the cancer includes, but is not limited to, a tissue cancer type, such as a solid tumor, or a migratory cancer type, such as a hematological malignancy. Such solid tumors include, but are not limited to, bladder cancer, breast cancer, cervical cancer, colon cancer (including colorectal cancer), esophageal cancer, head and neck cancer, liver cancer, lung cancer (small cell lung cancer and non-small cell lung cancer), melanoma, myeloma, neuroblastoma, ovarian cancer, pancreatic cancer, prostate cancer, kidney cancer, sarcoma (including osteosarcoma), skin cancer (including squamous cell carcinoma), stomach cancer, testicular cancer, thyroid cancer, uterine cancer, mesothelioma, cholangiocarcinoma, leiomyosarcoma, liposarcoma, melanoma, nasopharyngeal cancer, neuroendocrine cancer, ovarian cancer, renal cancer, salivary gland cancer, spindle cell carcinoma-induced metastases; the cancer also includes migratory tumors such as hematological malignancies, including but not limited to Acute Myeloid Leukemia (AML), Acute Lymphoblastic Leukemia (ALL), Chronic Lymphocytic Leukemia (CLL), Chronic Myeloid Leukemia (CML), acute eosinophilic cell leukemia, acute erythrocytic leukemia, acute megakaryocytic leukemia, acute monocytic leukemia, acute promyelocytic leukemia, adult T-cell leukemia/lymphoma, aggressive NK-cell leukemia, mast cell leukemia, hairy cell leukemia, mixed lineage leukemia, non-Hodgkin lymphoma, Hodgkin lymphoma, Mantle Cell Lymphoma (MCL), diffuse large B-cell lymphoma (DLBCL), Follicular Lymphoma (FL), B-cell lymphoma, mucosa-associated lymphoid tissue (MALT) lymphoma, anaplastic large cell lymphoma, T-cell lymphoma, Burkitt's lymphoma, T lymphoblastic lymphoma, primary central nervous system lymphoma, primary effusion lymphoma, multiple myeloma, macroglobulinemia, myelodysplastic syndrome (MDS), primary thrombocytosis, polycythemia vera, primary myelofibrosis.

In some embodiments, the cancer is Acute Myeloid Leukemia; in other embodiments, the cancer is myelodysplastic syndrome (MDS).

In some embodiments, the cancer is a drug-resistant cancer, such as a drug-resistant hematological malignancy, including but not limited to drug-resistant Acute Myeloid Leukemia or myelodysplastic syndrome.

In some embodiments, the Bcl-2/Bcl-xL inhibitor or a pharmaceutically acceptable salt or solvate thereof, is administered in an amount of about 0.0025 to 1500 mg/day.

In some embodiments, the chemotherapeutic agent, or a pharmaceutically acceptable salt or solvate thereof, is administered in an amount of about 0.005 mg/day to about 1000 mg/day.

DRAWINGS

FIG. 1 shows the synergistic anti-proliferative effect of compound 6 in combination with homoharringtonine on tumor cells in AML/MDS cell lines: AML/MDS cells were treated with gradient concentrations of Compound 6, homoharringtonine (HHT) in single or combination for 24 h and cell growth inhibitory activity was measured by CellTiter-Glo luminescence, with cell viability percent expressed as Mean±SEM and n=2.

FIG. 2 shows the synergistic apoptosis-inducing effect of Compound 6 in combination with homoharringtonine on tumor cells in AML/MDS cell lines: treating in vitro with 10 nM or 30 nM homoharringtonine (HHT) and 10 nM Compound 6 in single or combination for 24 h;
  A: apoptosis graphical representation; B: statistics of FIG. A;
  *: $p<0.05$ versus DMSO group;
  $: $p<0.05$ versus Compound 6 monotherapy;
  #: $p<0.05$ versus homoharringtonine (HHT) monotherapy;
  the percentage of Annexin $V^+$ cells (i.e. apoptotic cells) is expressed as Mean±SEM, n=2.

FIG. 3 shows that Compound 6 in combination with homoharringtonine reduced the expression of the anti-apoptotic proteins MCL-1 and the proto-oncoprotein MYC and enhanced the expression of the apoptosis markers cl-Caspase and cl-PARP in AML/MDS cell lines: MV-4-11, OCI-AML-3 and SKM-1 cells in the logarithmic growth phase were treated in vitro with 10 nM of Compound 6 in combination with the indicated concentration of homoharringtonine for 4 hours before cells were collected for protein extraction and immunoblot analysis.

FIG. 4 shows that the combination of Compound 6 with homoharringtonine disrupted the complexes Bcl-2:BIM (4A), Mcl-1:BIM (4B), Mcl-1:BAK (4C) and Bel-1:PUMA (4D), released pro-apoptotic proteins BIM, BAK and PUMA, in AML/MDS cell lines: MV-4-11, OCI-AML-3 and SKM-1 cells in the logarithmic growth phase were treated in vitro with the indicated concentrations of Compound 6 in combination with homoharringtonine (HHT) for 4 hours before cells were collected for protein extraction and MSD analysis. Electrochemical signal intensity is expressed as Mean±SEM, n=2.

DEFINITIONS

Figure 1:
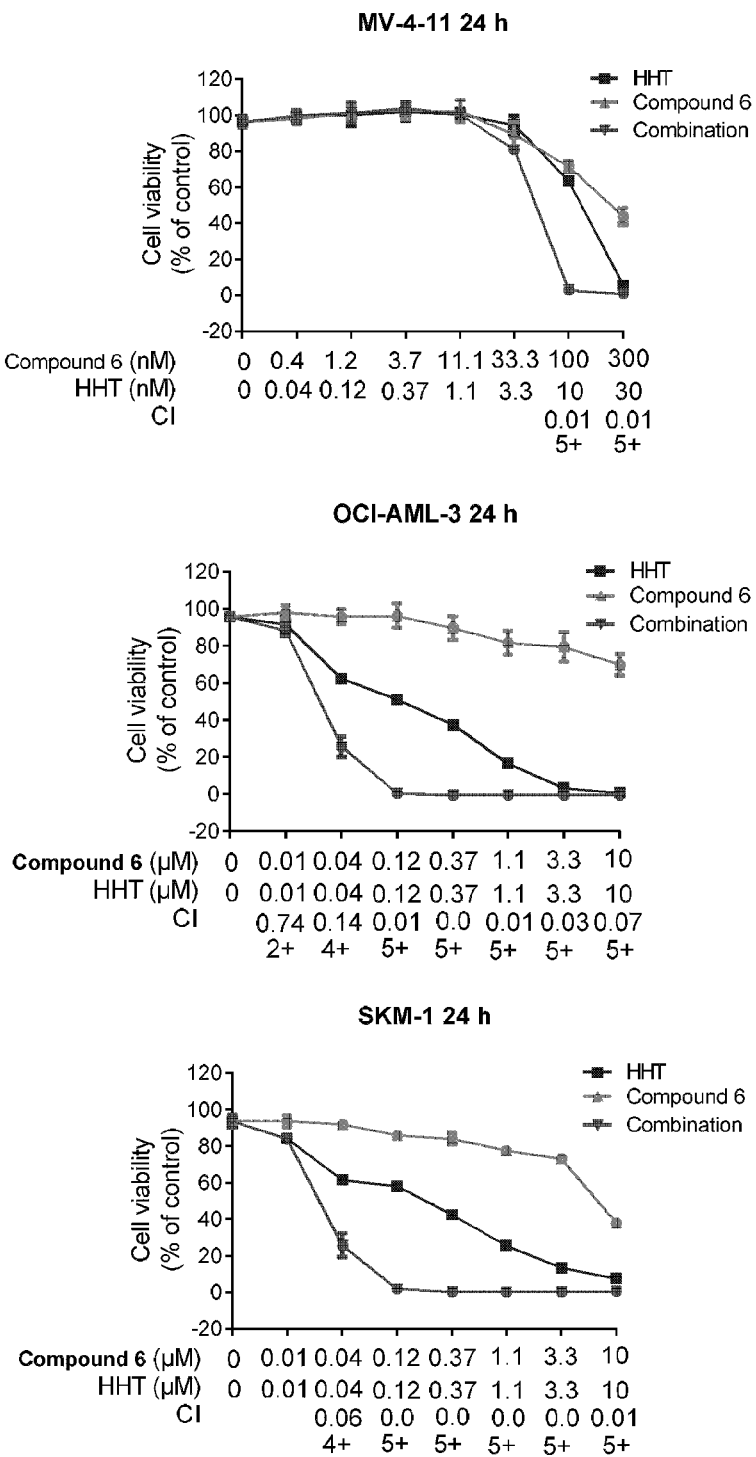

The term "Bcl-2/Bcl-xL" as used herein refers to Bcl-2, Bcl-xL, or Bcl-2 and Bcl-xL, i.e., Bcl-2 and/or Bcl-xL.

The term "pharmaceutically acceptable salt" as used herein refers to salts of the free acid or free base, typically prepared by reacting the free base with a suitable organic or inorganic acid or by reacting an acid with a suitable organic or inorganic base. The term may be used for any compound in the present invention. Representative salts include: acetate, benzenesulfonate, benzoate, bicarbonate, bisulfate, bitartrate, borate, bromide, calcium edetate, camphorsulfonate, carbonate, chloride, clavulanate, citrate, dihydrochloride, edetate, edisylate, estolate, ethanesulfonate (esylate), fumarate, glucoheptonate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, methanesulfonate, bromite, nitrite, sulfite, butenedioic acid monopotassium salt, Mucate, naphthalenesulfonate, nitrate, N-methylglucosamine salt, oxalate, pamoate, palmitate, pantothenate, phosphate/diphosphate, polygalacturonate, potassium salt, salicylate, sodium salt, stearate, subacetate, succinate, tannate, tartrate, teoclate, p-toluenesulfonate, triethiodode, trimethylamine, and valerate. When an acidic substituent such as —COOH is present, ammonium, morpholine, sodium, potassium, barium, calcium salts, and the like may be formed for use in a dosage form. When a basic group is present (e.g. in a limonoid or 1,1-dimethylbiguanide), for example an amino group or a basic heteroaryl group such as pyridyl, an acidic salt may be formed, such as hydrochloride, hydrobromide, phosphate, sulphate, trifluoroacetate, trichloroacetate, acetate, oxalate, maleate, pyruvate, malonate, succinate, citrate, tartrate, fumarate, mandelate, benzoate, cinnamate, mesylate, ethanesulphonate, picrate and the like.

The term "solvate" as used herein is a complex, physical association, and/or solvation, e.g. di-, mono-, semi-solvate of a compound as contemplated by the present invention with solvent molecules. The compounds of the present invention may be in solvated forms with pharmaceutically acceptable solvents such as water, methanol, ethanol and the like, which do not significantly affect the pharmacological activity or toxicity of the compounds and may act as pharmacological equivalents.

The term "cephalotaxine alkaloids" as used herein refers to alkaloid compounds derived mainly from *Cephalotaxus* plants such as *Cephalotaxus fortunei, Cephalotaxus sinensis, Cephalotaxus hainanensis, Cephalotaxus harringtonia, Cephalotaxus oliveri*, etc., and also includes alkaloid compounds obtained by culture of the plant cells, or semi-synthetic *Cephalotaxus* alkaloids obtained by attaching different ester side chains synthesized in advance to natural *Cephalotaxus* alkaloids. The term also includes Cephalotaxine compounds obtained by total-synthesis methods. Specific examples include those illustrated in the summary of the invention section above.

The term "active derivative of cephalotaxin alkaloid" as used herein refers to a derivative obtained by modifying cephalotaxin alkaloid by means including, but not limited to, biological or chemical means, which derivative retains the biological activity of cephalotaxin alkaloid.

The term "homoharringtonine" as used herein has the following structure, CAS 26833-87-4:

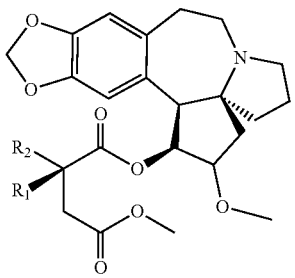

$R_1 = $ —OH, $R_2 = $ —$CH_2CH_2CH_2C(OH)(CH_3)_2$

The term "preventing" or "prevention" or "prophylactic" as used herein means that when used in relation to a disease or disorder (e.g., cancer), the compound or drug can reduce the frequency of or delay the onset of symptoms of the medical disorder in a subject as compared to a subject not administered the compound or drug (e.g., a combination product as claimed herein).

The term "treating" or "treatment" or "therapeutic" as used herein refers to alleviating, relieving or ameliorating symptom(s) of a disease or disorder, ameliorating an underlying metabolic-induced symptom, inhibiting a disease or disorder, e.g., arresting the extension of a disease or disorder, relieving a disease or disorder, causing regression of a disease or disorder, relieving a condition caused by a disease or disorder, or arresting a symptom of a disease or disorder.

The term "cancer" as used herein refers to a neoplasm or tumor caused by abnormal uncontrolled cell growth. Cancer often infiltrates adjacent tissues and spreads (metastasizes) to remote organs, such as to the bone, liver, lungs, or brain. Non-limiting examples of the term "cancer" as used herein include migratory tumor types (such as, but not limited to, melanoma, lymphoma, leukemia, fibrosarcoma, rhabdomyosarcoma, and mast cell tumor) and tissue cancer types (such as, but not limited to, colorectal cancer, small cell lung cancer, and non-small cell lung cancer, breast cancer, pancreatic cancer, bladder cancer, kidney cancer, stomach cancer, glioblastoma, primary liver cancer, ovarian cancer, prostate cancer, urinary tract cancer, thyroid cancer, esophageal cancer, and uterine leiomyosarcoma, among others), particularly those exemplary cancers described in the detailed description of the invention.

The term "cancer" as used herein includes diseases involving both premalignant and malignant cancer cells, and also includes all types of cancers of the present invention that are resistant to chemotherapy.

The term "subject" as used herein is meant to include humans (e.g., human patients) and animals (e.g., mice, rats, dogs, cats, rabbits, chickens, monkeys, etc.). When the subject is a human patient (typically having a body weight of 60 kg), the dosage described herein can be converted using conversion factors with experimental animals (e.g., human dose=mouse dose/12.3) unless otherwise indicated (see, for example, kin Tam, "Estimating the "First in human" dose—a revisit with particular emphasis on oncology drugs, ADMET & DMPK 1(4) (2013) 63-75). One of ordinary skill in the art would be able to, based on general knowledge, make reasonable adjustments to the dosage based on the subject's specific weight, the type and severity of the disease, and other factors, and such adjusted technical solutions are within the scope of the presently claimed invention.

The term "effective amount" or "prophylactically and/or therapeutically effective amount" as used herein refers to a sufficient amount (e.g., dose) of a drug or compound administered that will alleviate to some extent one or more of the symptoms of the disease or disorder being treated. The result may be a reduction and/or alleviation of the cause of a condition or disease or any other desired alteration of a biological system. For example, an "effective amount" for therapeutic use is that amount of a compound or drug (e.g., a combination product as claimed herein) that is provided such that the clinical symptoms of the disease or disorder are significantly reduced, without undue toxic side effects.

The terms "co-administration," "concurrent administration," "simultaneous administration," and similar expressions, as used herein, refer to the administration of two or more agents concurrently to a subject to be treated. By "concurrently" is meant that each agent is administered simultaneously, or each agent is administered sequentially in any order at different time points. If not simultaneously, it is meant that they are administered to the individual in any order and close enough in time to provide the desired therapeutic effect.

The term "kit" as used herein means that the ingredients (the Bcl-2/Bcl-xL inhibitor in free or pharmaceutically acceptable salt or solvate form and the combination partner chemotherapeutic agent of the invention) can be administered independently of each other or by using different fixed combinations with the specified amounts of the ingredients, i.e. at different time points or simultaneously. Thus, the parts of the kit may be administered simultaneously or chronologically staggered, that is at different time points and with equal or different time intervals for each part of the kit. The time intervals are preferably chosen such that the combined use of the parts results in a therapeutic effect on a disease or condition which is greater than the effect which would be obtained by use of either part alone. The components of the kit may each be in separate formulations, which may be the same or different.

The "kit" preferably has at least one beneficial effect, e.g. an effect of the individual combination partners which are mutually enhanced, additional advantageous effects, less side effects, combined therapeutic effects at non-effective doses of one or the individual components, and especially a synergistic effect, e.g. a more than additive effect between the Bel-2/Bcl-xL inhibitor in free or pharmaceutically acceptable salt or solvate form and the chemotherapeutic agent of the invention.

The term "dose" as used herein refers to the weight (e.g., milligrams (mg)) of active substance per kilogram (kg) of subject body weight.

The term "IC$_{50}$" as used herein refers to the concentration of drug that achieves 50% inhibition of the maximal effect in an assay measuring the corresponding effect.

The term "room temperature" as used herein means 25° C.±1° C. Meanwhile, the experimental temperatures are all room temperature unless otherwise specified.

The term "about" as used herein means ±10%, more preferably ±5%, and most preferably ±2% of the numerical value modified by the term, so that a person of ordinary skill in the art can clearly determine the range of the term "about" according to the modified numerical value.

Technical and scientific terms used herein that are not specifically defined have the same meaning as commonly understood by one of ordinary skill in the art to which this invention belongs.

DETAILED DESCRIPTION

Pharmacological studies of the present invention have shown that the combined use of a Bcl-2/Bcl-xL inhibitor, especially the preferred inhibitor as defined in the present specification and claims, and a chemotherapeutic agent, especially homoharringtonine, is capable of significantly inhibiting cancer cell proliferation, especially Acute Myeloid Leukemia cell proliferation, in a synergistic manner and significantly inducing apoptosis of cancer cells, especially Acute Myeloid Leukemia cells, in a synergistic manner.

Furthermore, the studies of the present inventors have also shown that the combined use of the two above significantly reduces the levels of the proto-oncoproteins MYC and Mcl-1 and synergistically disrupts the Bcl-2:BIM, Mcl-1:BAK and Bcl-1:PUMA complexes in cancer cells, thereby releasing the pro-apoptotic proteins BIM, BAK and PUMA.

Accordingly, in a first aspect the present invention provides a combination product comprising or consisting of a Bcl-2/Bcl-xL inhibitor and a chemotherapeutic agent, wherein the inhibitor is a compound having formula I-A:

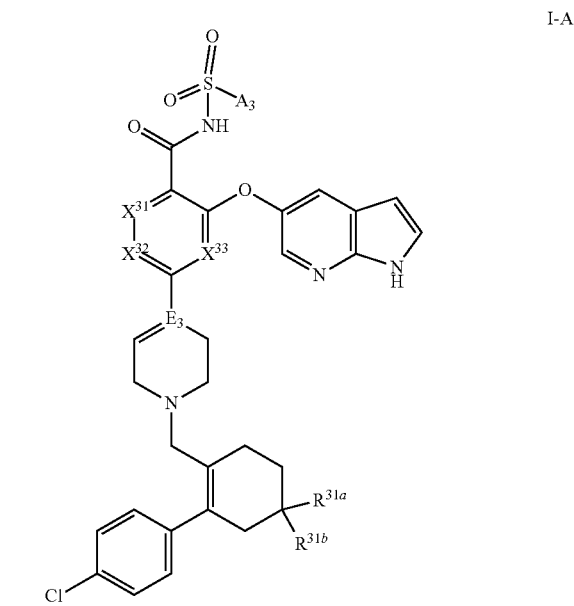

wherein

A$_3$ is selected from the group consisting of

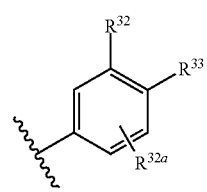

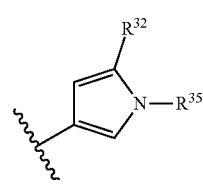

-continued

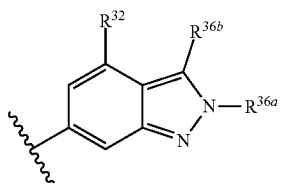
A-3

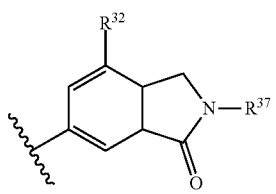
A-4

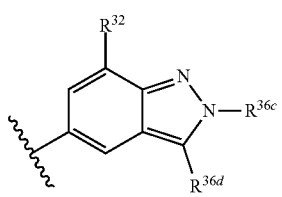
A-5

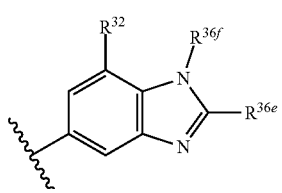
A-6

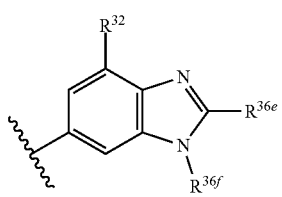
A-7

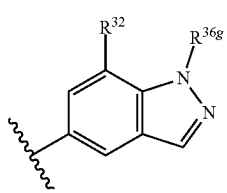
A-8

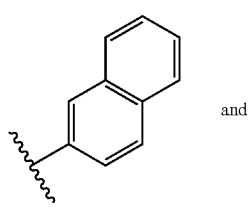
and
A-9

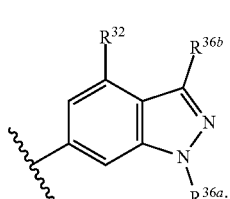
A-10

$E_3$ is a C atom and $=\!=\!=$ is a double bond;
or $E_3$ is —C(H)— and $=\!=\!=$ is a single bond;
or $E_3$ is a N atom and $=\!=\!=$ is a single bond;
$X^{31}$, $X^{32}$, and $X^{33}$ are each independently —CR$^{38}$= or —N=;
$R^{31a}$ and $R^{31b}$ taken together with the C atom to which they are attached form 3-, 4-, or 5-membered optionally substituted cycloalkyl; or
$R^{31a}$ and $R^{31b}$ taken together with the C atom to which they are attached form a 4- or 5-membered optionally substituted heterocyclic ring;
$R^{32}$ is —NO$_2$, —SO$_2$CH$_3$, or —SO$_2$CF$_3$;
$R^{32a}$ is H or X;
$R^{33}$ is H, —CN, —C≡CH, or —N(R$^{34a}$)(R$^{34b}$);
$R^{34a}$ is optionally substituted C$_{1-6}$alkyl, optionally substituted C$_{3-6}$cycloalkyl, heterocycle, heteroalkyl, (cycloalkyl)alkyl or heterocycloalkyl;
$R^{34b}$ is H or C$_{1-4}$alkyl;
$R^{35}$ is optionally substituted C$_{1-6}$alkyl, heterocycle, heteroalkyl, (cycloalkyl)alkyl or heterocycloalkyl;
$R^{36a}$, $R^{36c}$, $R^{36e}$, $R^{36f}$ and $R^{36g}$ are each independently H, optionally substituted C$_{1-6}$ alkyl, optionally substituted C$_{3-6}$cycloalkyl, optionally substituted aryl, optionally substituted heteroaryl, heterocycle, heteroalkyl, (cycloalkyl)alkyl, or heterocycloalkyl;
$R^{36b}$ and $R^{36d}$ are each independently H, C$_{1-4}$alkyl or halogen;
$R^{37}$ is optionally substituted C$_{1-6}$alkyl, heterocycle, heteroalkyl, (cycloalkyl)alkyl, or heterocycloalkyl;
$R^{38}$ is H or halogen.

In the compounds of the formula I-A above, "X" in the definition of the variable $R^{32a}$ refers to halogen. Further, the halogen means fluorine (F), chlorine (Cl), bromine (Br) or iodine (I).

In some embodiments, the inhibitor is a compound having the formula I-A, wherein: $A_3$ is A-1, A-2, A-3, A-4, A-5, A-6, A-7, A-8 or A-9; $R^{34a}$ is optionally substituted C$_{1-6}$alkyl, heterocycle, heteroalkyl, (cycloalkyl)alkyl or heterocycloalkyl; $R^{36a}$, $R^{36c}$, $R^{36e}$, $R^{36f}$ and $R^{36g}$ are each independently H, optionally substituted C$_{1-6}$ alkyl, heterocycle, heteroalkyl, (cycloalkyl)alkyl or heterocycloalkyl.

In some embodiments, the inhibitor is a compound having formula I-b, or a pharmaceutically acceptable salt or solvate thereof,

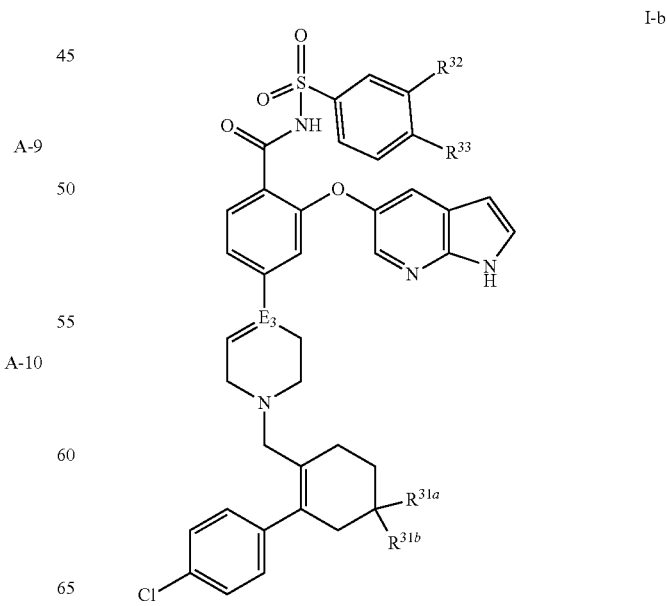

I-b wherein:

E$_3$ is a C atom and === is a double bond; or E$_3$ is —C(H)— and === is a single bond; or E$_3$ is a N atom and === is a single bond;

R$^{31a}$ and R$^{31b}$ taken together with the C atom to which they are attached form a 3-, 4- or 5-membered optionally substituted cycloalkyl; or R$^{31a}$ and R$^{31b}$ taken together with the C atom to which they are attached form a 4- or 5-membered optionally substituted heterocyclic ring;

R$^{32}$ is —NO$_2$, —SO$_2$CH$_3$, or —SO$_2$CF$_3$;

R$^{33}$ is H, —CN, —C≡CH, or —N(R$^{34a}$)(R$^{34b}$);

R$^{34a}$ is optionally substituted C$_{1-6}$alkyl, heterocycle, (cycloalkyl)alkyl or heterocycloalkyl;

R$^{34b}$ is H or C$_{1-4}$alkyl.

In some embodiments, the inhibitor is a compound having formula I-c, or a pharmaceutically acceptable salt or solvate thereof,

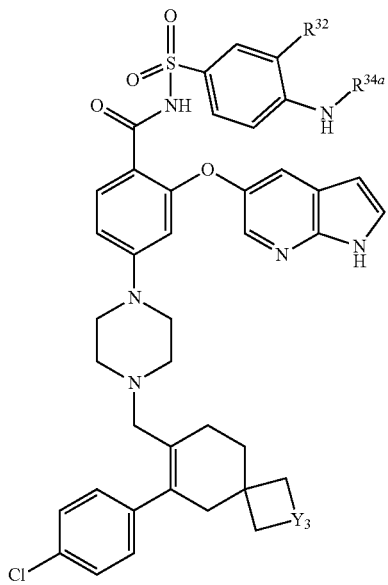

I-c wherein Y$_3$ is —CH$_2$— or —O—, R$^{32}$ and R$^{34a}$ are as defined for formula I-b.

In some embodiments, the inhibitor is a compound having formula I-d, or a pharmaceutically acceptable salt or solvate thereof,

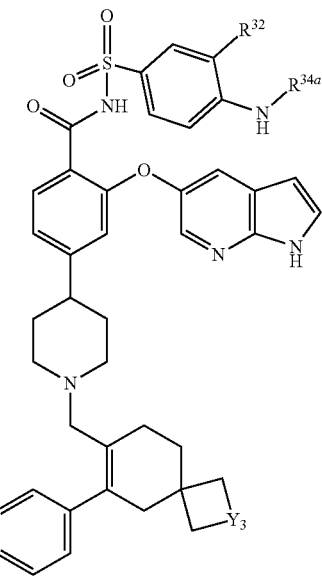

I-d wherein Y$_3$ is —CH$_2$— or —O—, R$^{32}$ and R$^{34a}$ are as defined for formula I-b.

In some embodiments, the inhibitor is a compound having formula I-e, or a pharmaceutically acceptable salt or solvate thereof,

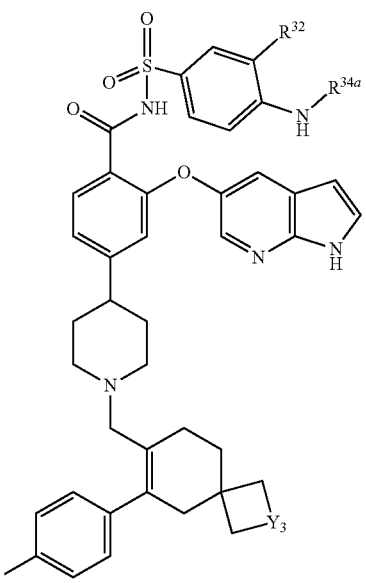

I-e wherein Y$_3$ is —CH$_2$— or —O—, R$^{32}$ and R$^{34a}$ are as defined for formula I-b.

In some embodiments, the inhibitor is a compound having formula I-f, or a pharmaceutically acceptable salt or solvate thereof, I-f

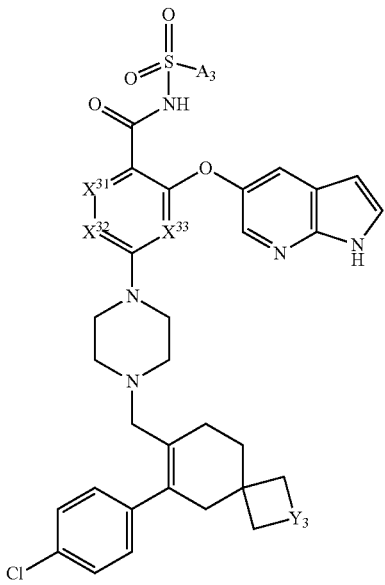

wherein $Y_3$ is —$CH_2$— or —O—, $A_3$, $X^{31}$, $X^{32}$ and $X^{33}$ are as defined for formula I-A.

In some embodiments, the inhibitor is a compound having the formula I-g, or a pharmaceutically acceptable salt or solvate thereof, I-g

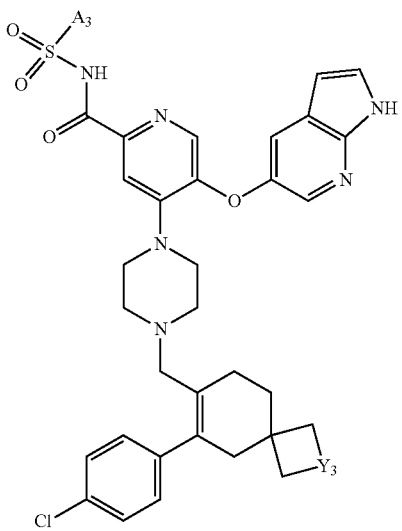

wherein $Y_3$ is —$CH_2$— or —O—, $A_3$ is as defined for formula I-A.

In some embodiments, the inhibitor is a compound having the formula I-A, I-f or I-g, or a pharmaceutically acceptable salt or solvate thereof, wherein $A_3$ is A-1.

In some embodiments, the inhibitor is a compound having the formula I-A, I-f or I-g, or a pharmaceutically acceptable salt or solvate thereof, wherein $A_3$ is A-2.

In some embodiments, the inhibitor is a compound having the formula I-A, I-f or I-g, or a pharmaceutically acceptable salt or solvate thereof, wherein $A_3$ is A-3.

In some embodiments, the inhibitor is a compound having the formula I-A, I-f or I-g, or a pharmaceutically acceptable salt or solvate thereof, wherein $A_3$ is A-4.

In some embodiments, the inhibitor is a compound having the formula I-A, I-f or I-g, or a pharmaceutically acceptable salt or solvate thereof, wherein $A_3$ is A-5.

In some embodiments, the inhibitor is a compound having the formula I-A, I-f or I-g, or a pharmaceutically acceptable salt or solvate thereof, wherein $A_3$ is A-6.

In some embodiments, the inhibitor is a compound having the formula I-A, I-f or I-g, or a pharmaceutically acceptable salt or solvate thereof, wherein $A_3$ is A-7.

In some embodiments, the inhibitor is a compound having the formula I-A, I-f or I-g, or a pharmaceutically acceptable salt or solvate thereof, wherein $A_3$ is A-8.

In some embodiments, the inhibitor is a compound having the formula I-A, I-f or I-g, or a pharmaceutically acceptable salt or solvate thereof, wherein $A_3$ is A-9.

In some embodiments, the inhibitor is a compound having the formula I-A, I-f or I-g, or a pharmaceutically acceptable salt or solvate thereof, wherein $A_3$ is A-10.

In some embodiments, the inhibitor is a compound having formula I-h, or a pharmaceutically acceptable salt or solvate thereof, I-h

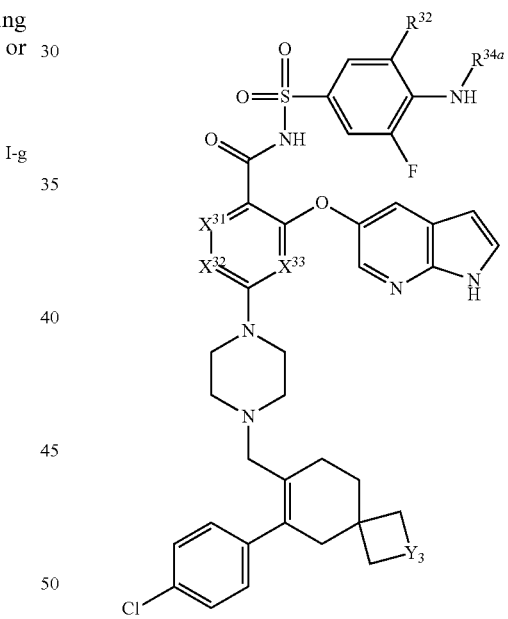

wherein $Y_3$ is —$CH_2$— or —O—, $X^{31}$, $X^{32}$, $X^{33}$, $R^{32}$ and $R^{34a}$ are as defined for formula I-A.

In some embodiments, the inhibitor is a compound having the formula I-A, I-f or I-h, or a pharmaceutically acceptable salt or solvate thereof, wherein $X^{31}$, $X^{32}$, and $X^{33}$ are all —CH=.

In some embodiments, the inhibitor is a compound having the formula I-A, I-f or I-h, or a pharmaceutically acceptable salt or solvate thereof, wherein $X^{31}$ is —CF=, and $X^{32}$ and $X^{33}$ are both —CH=.

In some embodiments, the inhibitor is a compound having the formula I-A, I-f or I-h, or a pharmaceutically acceptable salt or solvate thereof, wherein $X^{31}$ and $X^{33}$ are both —CH=, and $X^{32}$ is —CF=.

In some embodiments, the inhibitor is a compound having the formula I-A, I-f or I-h, or a pharmaceutically acceptable salt or solvate thereof, wherein $X^{31}$ and $X^{32}$ are both —CH=, and $X^{33}$ is —CF=.

In some embodiments, the inhibitor is a compound having the formula I-A, I-f or I-h, or a pharmaceutically acceptable salt or solvate thereof, wherein $X^{31}$ is —N=, and $X^{32}$ and $X^{33}$ are both —CH=.

In some embodiments, the inhibitor is a compound having the formula I-A, I-f or I-h, or a pharmaceutically acceptable salt or solvate thereof, wherein $X^{31}$ and $X^{33}$ are both —CH=, and $X^{32}$ is —N=.

In some embodiments, the inhibitor is a compound having the formula I-A, I-f or I-h, or a pharmaceutically acceptable salt or solvate thereof, wherein $X^{31}$ and $X^{32}$ are both —CH=, and $X^{33}$ is —N=.

In some embodiments, the inhibitor is a compound having any one of formulae I-c through I-h, or a pharmaceutically acceptable salt or solvate thereof, wherein $Y_3$ is —O—.

In some embodiments, the inhibitor is a compound having any one of formulae I-c through I-h, or a pharmaceutically acceptable salt or solvate thereof, wherein $Y_3$ is —CH$_2$—.

In some embodiments, the inhibitor is a compound having any one of formulae I-A or I-b~I-h, or a pharmaceutically acceptable salt or solvate thereof, wherein $R^{32}$ is —NO$_2$.

In some embodiments, the inhibitor is a compound having any one of formulae I-b~I-e, or a pharmaceutically acceptable salt or solvate thereof, wherein $R^{34a}$ is:

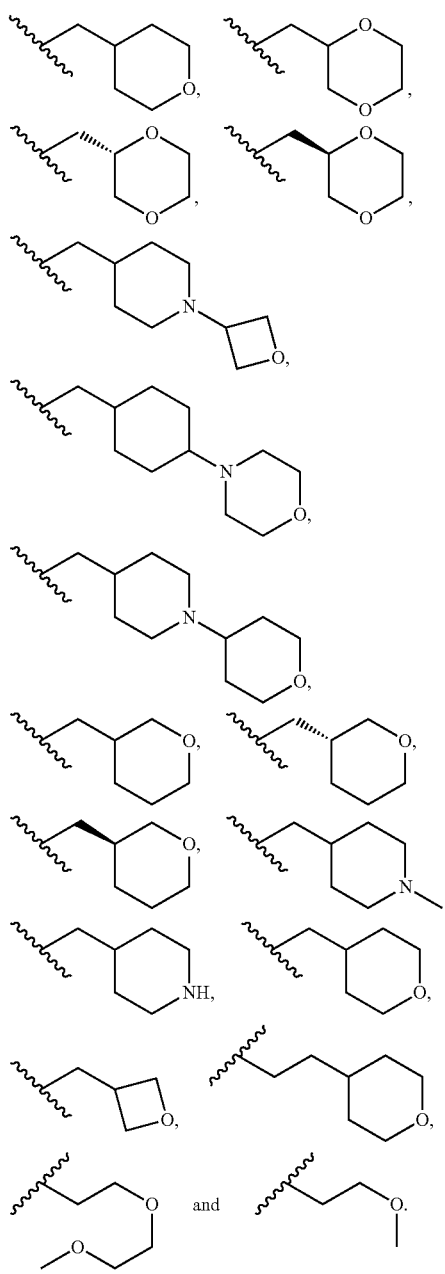

In some embodiments, the inhibitor is a compound having any one of formulae I-a or I-f~I-h, or a pharmaceutically acceptable salt or solvate thereof, wherein $R^{34a}$, $R^{35}$, $R^{36a}$, and $R^{37}$ are independently:

In some embodiments, the inhibitor is a compound having formula I-i, or a pharmaceutically acceptable salt or solvate thereof, wherein $R^{32a}$, is H or F, $R^{34a}$ is as defined for formula I-A.

I-i

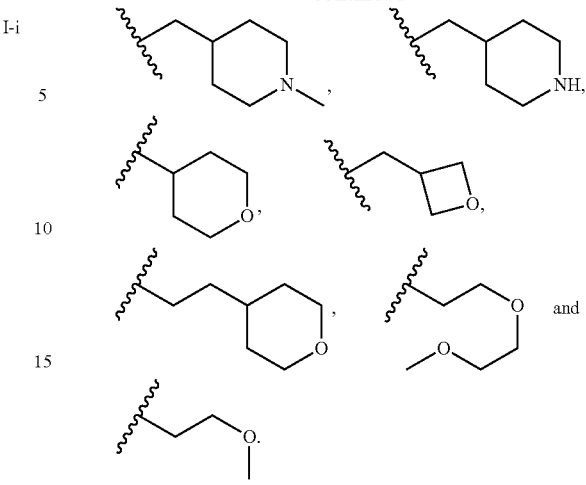

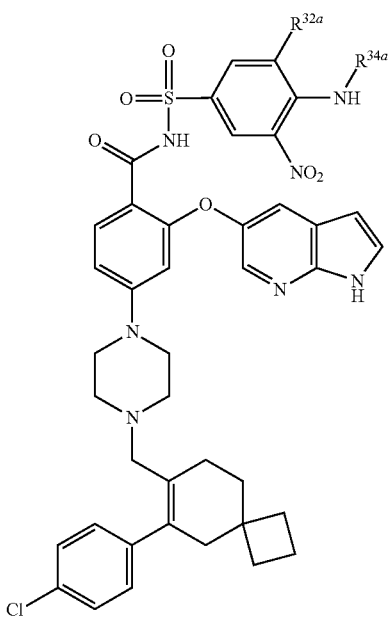

In some embodiments, the inhibitor is a compound having formula I-i, or a pharmaceutically acceptable salt or solvate thereof, wherein $R^{34a}$ is:

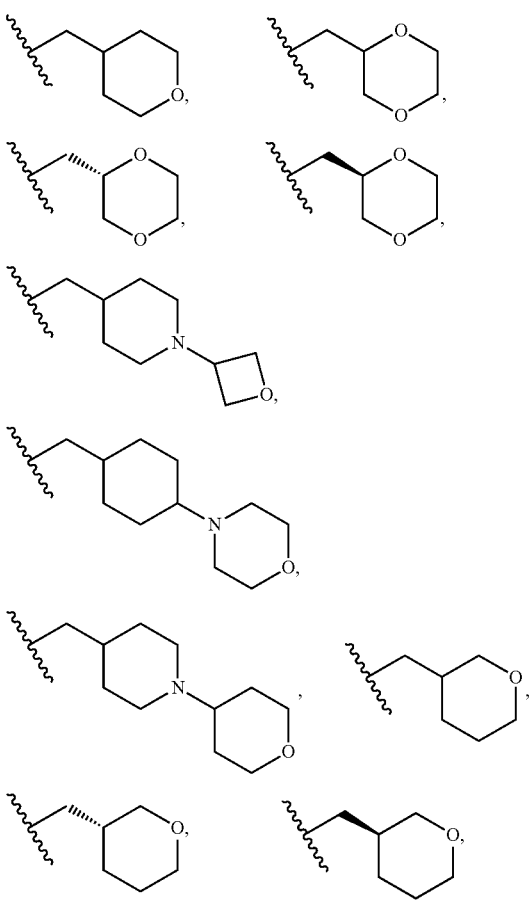

-continued

For the inhibitors of formula I-A~I-i above in the present application, the term "halogen" by itself or as part of another group refers to —Cl, —F, —Br or —I.

For the inhibitors of formulae I-A~I-i above in the present application, the term "nitro", used alone or as part of another group, means —NO$_2$.

For the inhibitors of formulae I-A~I-i above of the present application, the term "cyano" as such or as part of another group refers to —CN.

For the inhibitors of formulae I-A~I-i above in the present application, the term "hydroxy" used alone or as part of another group refers to —OH.

For the inhibitors of formulae I-A~I-I above in the present application, the term "amino" by itself or as part of another group refers to —NH$_2$.

For the inhibitors of the above formulae I-A~I-i of the present application, the term "alkyl" by itself or as part of another group refers to unsubstituted straight or branched chain aliphatic hydrocarbons containing from one to twelve carbon atoms, i.e., $C_{1-12}$alkyl, or a specified number of carbon atoms, e.g., $C_1$alkyl such as methyl, $C_2$alkyl such as ethyl, $C_3$alkyl such as propyl or isopropyl, $C_{1-3}$alkyl such as methyl, ethyl, propyl or isopropyl, and the like. In one embodiment, alkyl is a straight chain $C_{1-6}$group. In another embodiment, the alkyl group is a branched $C_{3-6}$alkyl group. In another embodiment, the alkyl group is a straight chain $C_{1-4}$alkyl group. In another embodiment, the alkyl group is a branched $C_{3-4}$alkyl group. In another embodiment, the alkyl group is a straight or branched chain $C_{3-4}$alkyl group. In another embodiment, the alkyl group is partially or fully deuterated, i.e., one or more hydrogen atoms of the alkyl group are substituted with deuterium atoms. Non-limiting exemplary $C_{1-12}$alkyl groups include methyl, —CD$_3$, ethyl, propyl, isopropyl, butyl, sec-butyl, tert-butyl, isobutyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and isobutyl. Non-limiting exemplary $C_{1-4}$groups include methyl, ethyl, propyl, isopropyl, and tert-butyl.

For the inhibitors of formulae I-A~I-i above of the present application, the term "optionally substituted alkyl" by itself or as part of another group refers to unsubstituted alkyl or alkyl substituted with one, two or three substituents independently selected from halogen, nitro, cyano, hydroxy, alkoxy, amino, alkylamino, dialkylamino and optionally substituted aryl. In one embodiment, the optionally substituted alkyl is substituted with two substituents. In another embodiment, the optionally substituted alkyl is substituted with one substituent. In another embodiment, optionally substituted alkyl is unsubstituted. Non-limiting optionally substituted alkyl groups include —CH$_2$Ph, —CH$_2$CH$_2$NO$_2$, —CH$_2$CH$_2$OH, —CH$_2$CH$_2$OCH$_3$, and —CH$_2$CH$_2$F.

For the inhibitors of formula I-A~I-i above of the present application, the term "cycloalkyl" by itself or as part of another group refers to unsubstituted saturated or partially unsaturated, e.g. one or two double bonds-containing cyclic aliphatic hydrocarbons, containing one to three rings with three to twelve carbon atoms, i.e., C$_{3-12}$cycloalkyl, or a specified number of carbon atoms. In one embodiment, the cycloalkyl group has two rings. In one embodiment, the cycloalkyl group has one ring. In another embodiment, cycloalkyl is C$_{3-8}$cycloalkyl. In another embodiment, cycloalkyl is C$_{3-6}$ cycloalkyl. In another embodiment, cycloalkyl is C$_{3-5}$cycloalkyl. The term "cycloalkyl" is meant to include groups wherein -CH$_2$— is replaced by —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, cyclopentanone, spiro[3.3]heptane, and bicyclo[3.3]nonane.

For the inhibitors of formulae I-A~I-i above of the present application, the term "optionally substituted cycloalkyl" by itself or as part of another group refers to cycloalkyl unsubstituted or substituted with one, two or three substituents independently selected from: halogen, nitro, cyano, hydroxy, alkyl, alkoxy, amino, alkylamino, dialkylamino, haloalkyl, and heterocyclyl. In one embodiment, optionally substituted cycloalkyl is substituted with two substituents. In another embodiment, optionally substituted cycloalkyl is substituted with one substituent. In another embodiment, optionally substituted cycloalkyl is unsubstituted.

For the inhibitors of formulae I-A~I-i above of the present application, the term "haloalkyl" as such or as part of another group refers to an alkyl group substituted with one or more fluorine, chlorine, bromine and/or iodine atoms. In one embodiment, the alkyl group is substituted with one, two or three fluorine and/or chlorine atoms. In another embodiment, haloalkyl is C$_{1-4}$haloalkyl. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl.

For the inhibitors of formulae I-A~I-i above of the present application, the term "alkoxy" by itself or as part of another group refers to an optionally substituted alkyl group attached to the terminal oxygen atom. In one embodiment, alkoxy is C$_{1-6}$alkyl attached to a terminal oxygen atom. In another embodiment, alkoxy is C$_{1-4}$alkyl attached to a terminal oxygen atom. Non-limiting exemplary alkoxy groups include methoxy, ethoxy, and t-butoxy.

For the inhibitors of formulae I-A~I-i above of the present application, the term "aryl" by itself or as part of another group refers to an unsubstituted monocyclic or bicyclic aromatic ring system having 6 to 14 carbon atoms, i.e., C$_{6-14}$aryl. Non-limiting exemplary aryl groups include phenyl (abbreviated "Ph"), naphthyl, phenanthryl, anthracyl, indenyl, azulenyl, biphenyl, biphenylene, and fluorenyl. In one embodiment, aryl is phenyl or naphthyl.

For the inhibitors of formulae I-A~I-i above of the present application, the term "optionally substituted aryl" by itself or as part of another group refers to unsubstituted aryl or aryl substituted with 1-5 substituents independently selected from halogen, nitro, cyano, hydroxy, alkyl, alkoxy, amino, alkylamino, dialkylamino, haloalkyl and heterocyclyl. In one embodiment, the optionally substituted aryl is optionally substituted phenyl. In another embodiment, the optionally substituted phenyl group has one substituent. In another embodiment, the optionally substituted phenyl is unsubstituted. Non-limiting exemplary substituted aryl groups include 2-methylphenyl, 2-methoxyphenyl, 2-fluorophenyl, and 4-chlorophenyl.

For the inhibitors of formulae I-A~I-i above of the present application, the term "heterocyclyl" by itself or as part of another group means unsubstituted saturated or partially unsaturated, e.g., containing one or two double bonds, cyclic groups containing one, two or three rings having 3 to 14 ring members, i.e., 3 to 14 membered heterocyclic rings, wherein at least one carbon atom of one ring is substituted with a heteroatom. The term "heterocyclyl" is meant to include cyclic urea groups, such as imidazolidin-2-ones, cyclic amide groups, such as beta-lactams, gamma-lactams, delta-lactams, and epsilon-lactams, and cyclic carbamate groups, such as oxazolidin-2-ones. In one embodiment, heterocyclyl is a 4-, 5-, 6-, 7-, or 8-membered cyclic group containing one ring and one or two oxygen and/or nitrogen atoms. In one embodiment, heterocyclyl is a 5- or 6-membered cyclic group containing one ring and one or two nitrogen atoms. In one embodiment, heterocyclyl is an 8-, 9-, 10-, 11-, or 12-membered cyclic group containing two rings and one or two nitrogen atoms. In one embodiment, heterocyclyl is a 4- or 5-membered cyclic group containing one ring and one oxygen atom. The heterocyclyl group may optionally be attached to the remainder of the molecule through a carbon or nitrogen atom. Non-limiting exemplary heterocyclyl groups include 1,4-dioxane, 2-oxopyrrolidin-3-yl, 2-imidazolidinone, piperidinyl, morpholinyl, piperazinyl, pyrrolidinyl, 8-azabicyclo[3.2.1]octane(nortropane), 6-azaspiro[2.5]octane, 6-azaspiro[3.4]octane, indolinyl, indolin-2-one, and 1,3-dihydro-2H-benzo[d]imidazol-2-one.

For the inhibitors of formulae I-A~I-i above of the present application, the term "optionally substituted heterocyclyl" by itself or as part of another group as used herein refers to a heterocycle that is unsubstituted or substituted with one, two or three substituents independently selected from: halogen, nitro, cyano, hydroxy, alkyl, alkoxy, amino, alkylamino, dialkylamino, haloalkyl, and heterocyclyl. Non-limiting optionally substituted heterocyclyl groups include:

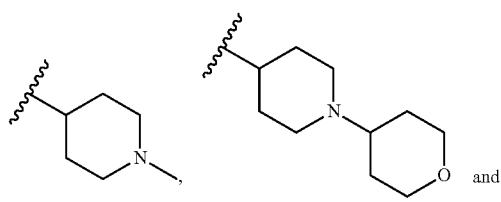

and

-continued

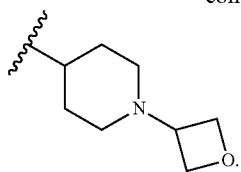

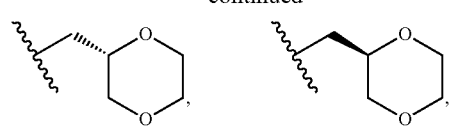

For the inhibitors of formulae I-A~I-i above of the present application, the term "alkylamino" used alone or as part of another group refers to —NHR$^{10}$, where R$^{10}$ is C$_{1-6}$ alkyl. In one embodiment, R$^{10}$ is C$_{1-4}$alkyl. Non-limiting exemplary alkylamino groups include —N(H)CH$_3$ and —N(H)CH$_2$CH$_3$.

For the inhibitors of formula I-A~I-i above of the present application, the term "dialkylamino" used alone or as part of another group, refers to —NR$^{11a}$R$^{11b}$, wherein R$^{11a}$ and R$^{11b}$ are each independently C$_{1-6}$alkyl. In one embodiment, R$^{11a}$ and R$^{11b}$ are each independently C$_{1-4}$alkyl. Non-limiting exemplary dialkylamino groups include —N(CH$_3$)$_2$ and —N(CH$_3$)CH$_2$CH(CH$_3$)$_2$.

For the inhibitors of formulae I-A~I-i above of the present application, the term "(cycloalkyl)alkyl" as used by itself or as part of another group refers to an alkyl group substituted with one optionally substituted cycloalkyl. In one embodiment, (cycloalkyl)alkyl is C$_{1-4}$alkyl substituted with one optionally substituted C$_{3-6}$cycloalkyl. In one embodiment, optionally substituted cycloalkyl is substituted with heterocyclyl. Non-limiting exemplary (cycloalkyl)alkyl groups include:

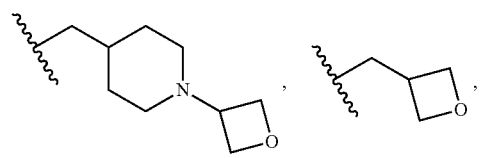

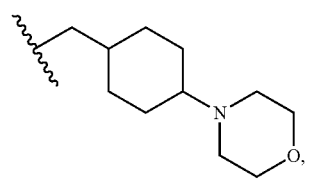

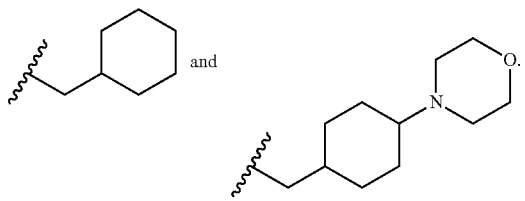 [SMILES: *CC1CCCCC1 ; *CC1CCC(N2CCOCC2)CC1]

For the inhibitors of formulae I-A~I-i above of the present application, the term "heterocycloalkyl" used by itself or as part of another group refers to an alkyl group substituted with one optionally substituted heterocyclic group. In one embodiment, heterocycloalkyl is C$_{1-4}$alkyl substituted with one optionally substituted 4- to 6-membered heterocyclyl. The heterocyclic group may be attached to the alkyl group through a carbon or nitrogen atom. Non-limiting exemplary (heterocyclic)alkyl groups include:

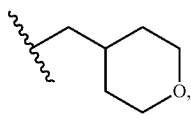 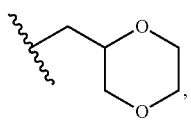

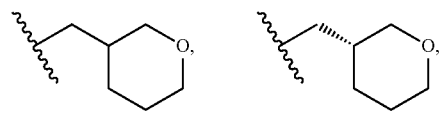

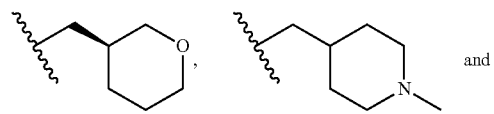

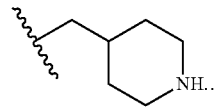

For the inhibitors of formulae I-A~I-i above of the present application, the term "heteroalkyl," as used by itself or as part of another group, refers to an unsubstituted straight or branched chain aliphatic hydrocarbon containing from 6 to 12 chain atoms, i.e., a 6 to 12 membered heteroalkyl, or a specified number of chain atoms, wherein at least two —CH$_2$— groups are independently replaced by —O—, —N(H)— or —S—. —O—, —N(H)— or —S— may independently be located at any internal position of the aliphatic hydrocarbon chain, provided that each —O—, N(H)— or —S— group is separated by at least two —CH$_2$— groups. In one embodiment, two —CH$_2$— groups are replaced by two —O— groups. In another embodiment, three —CH$_2$— groups are replaced by three —O— groups. Non-limiting exemplary heteroalkyl groups include —CH$_2$CH$_2$OCH$_2$CH$_2$OCH$_3$, —CH$_2$CH$_2$OCH$_2$CH$_2$N(H)CH$_3$, and —CH$_2$CH$_2$OCH$_2$CH$_2$OCH$_2$CH$_2$OCH$_3$.

In some embodiments, the inhibitor of formulae I-A~I-i is one or more of the compounds in the following table, or a pharmaceutically acceptable salt or solvate thereof.

TABLE 1

| No. | Structure | Name |
|---|---|---|
| 1 | 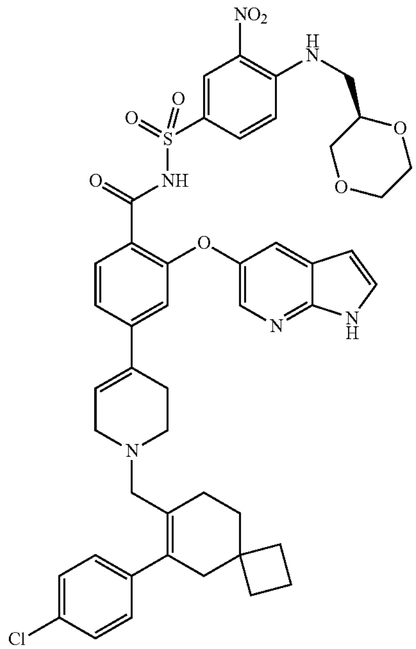 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide |
| 2 | 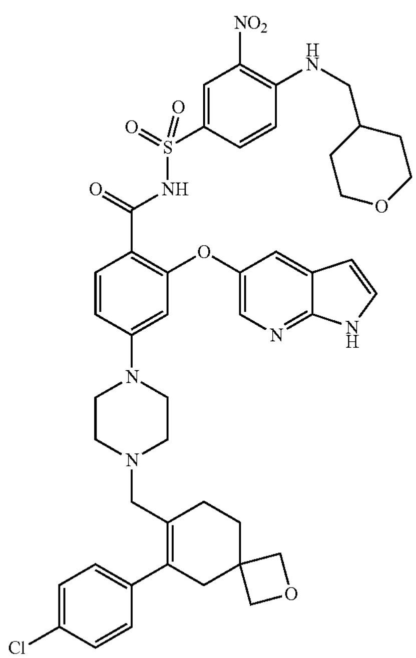 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide |

TABLE 1-continued
| No. | Structure | Name |
|---|---|---|
| 3 | 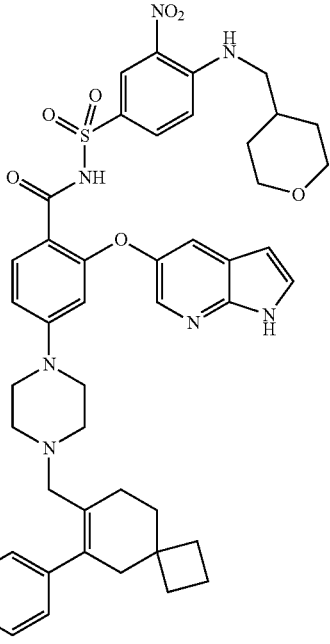 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide |
| 4 | 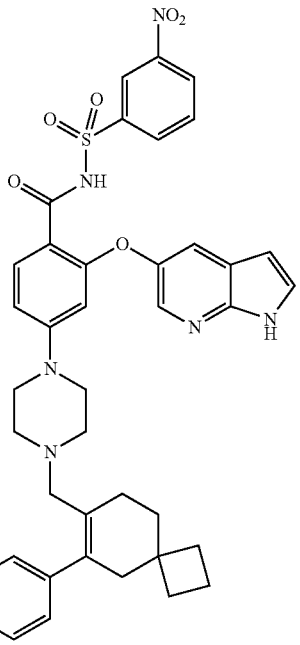 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitrophenyl)sulfonyl)benzamide |

TABLE 1-continued

| No. | Structure | Name |
|-----|-----------|------|
| 5 | 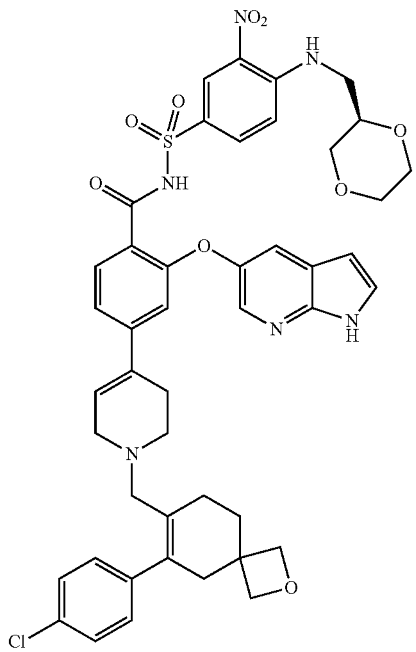 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)benzamide |
| 6 | 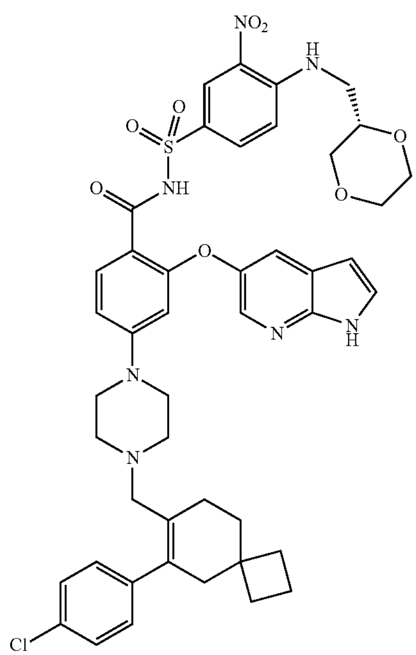 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-continued
| No. | Structure | Name |
|---|---|---|
| 7 | 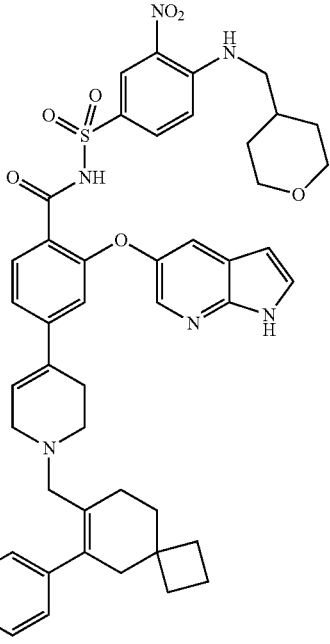 | 2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 8 | 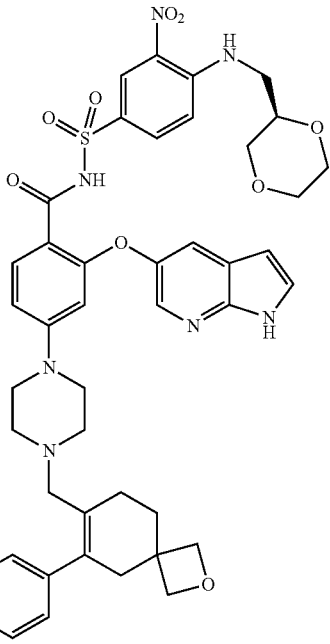 | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide |

TABLE 1-continued
| No. | Structure | Name |
|---|---|---|
| 9 | 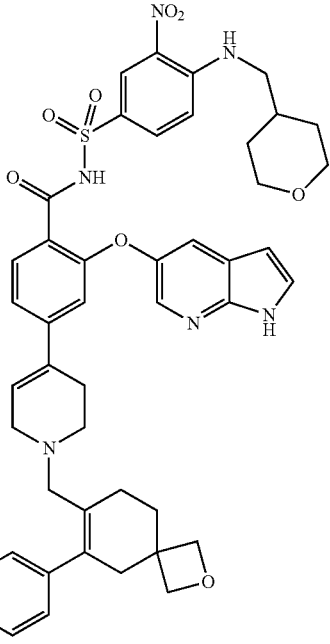 | 2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 10 | 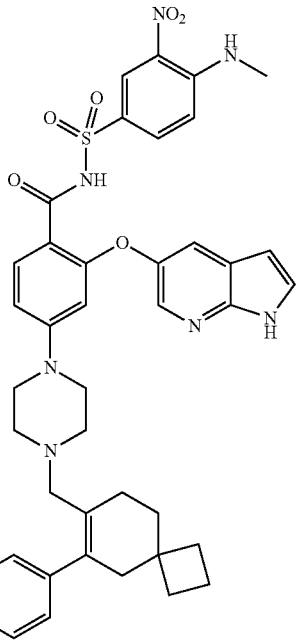 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(methylamino)-3-nitrophenyl)sulfonyl)benzamide |

TABLE 1-continued
| No. | Structure | Name |
|---|---|---|
| 11 | 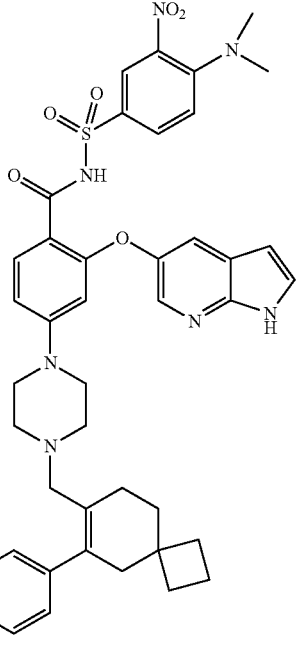 | 2-((1H-pyrrolo[2,3-b]pyridin-5-yl)oxy)-4-(4-(((6-(4-chlorophenyl)spiro[3.5]non-6-en-7-yl)methyl)piperazin-1-yl)-N-((4-(dimethylamino)-3-nitrophenyl)sulfonyl)benzamide |
| 12 | 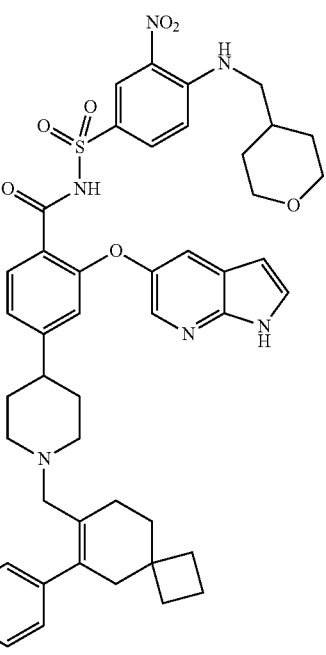 | 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide |

TABLE 1-continued
| No. | Structure | Name |
|---|---|---|
| 13 | 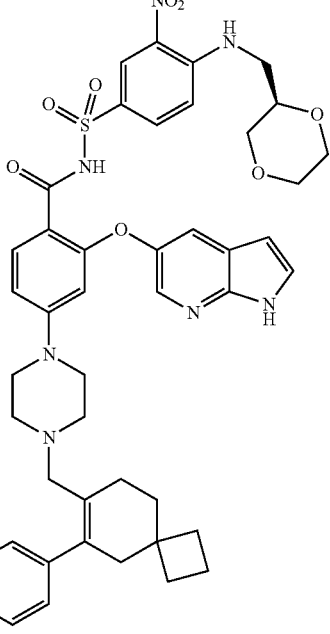 | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 14 | 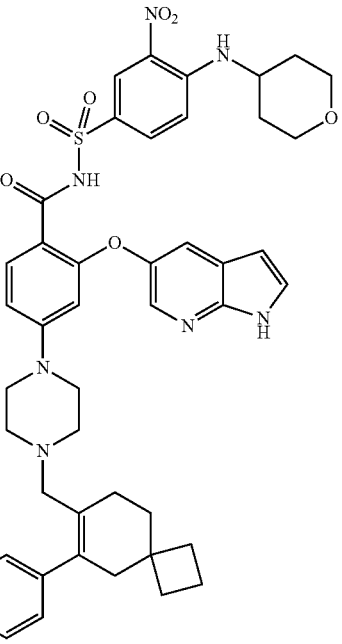 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((tetrahydro-2H-pyran-4-yl)amino)phenyl)sulfonyl)benzamide |

TABLE 1-continued
| No. | Structure | Name |
|---|---|---|
| 15 | 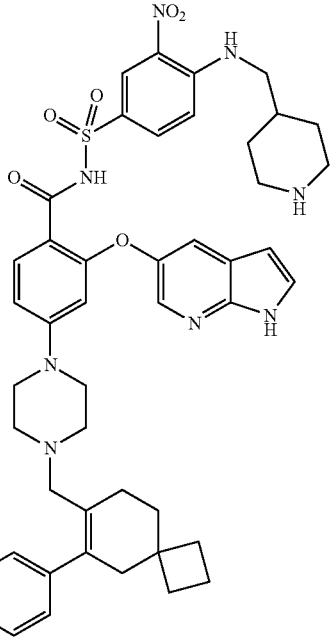 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((piperidin-4-ylmethyl)amino)phenyl)sulfonyl)benzamide |
| 16 | 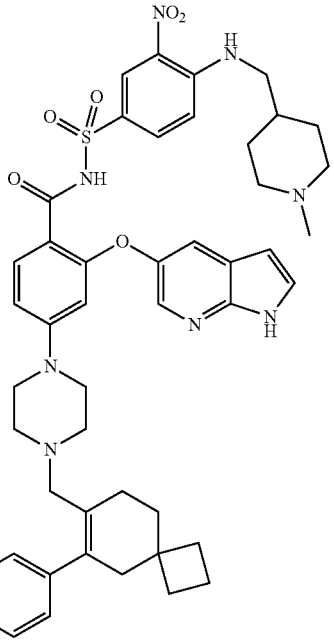 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(((1-methylpiperidin-4-yl)methyl)amino)-3-nitrophenyl)sulfonyl)benzamide |

TABLE 1-continued
| No. | Structure | Name |
|---|---|---|
| 17 | 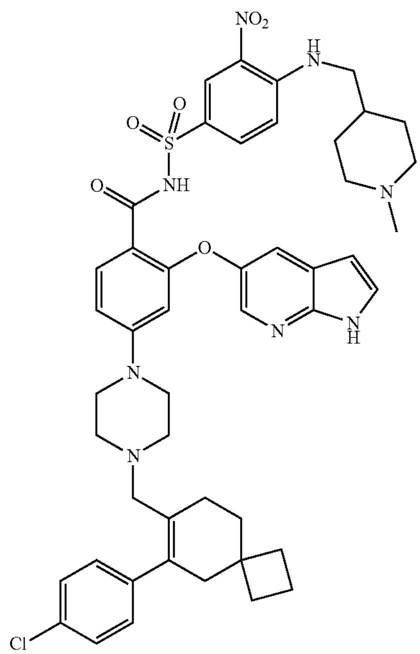 [SMILES: CN1CCC(CNc2ccc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2[N+](=O)[O-])CC1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(tetrahydro-2H-pyran-4-yl)piperidin-4-yl)methyl)amino)phenyl)sulfonyl)benzamide |
| 18 | 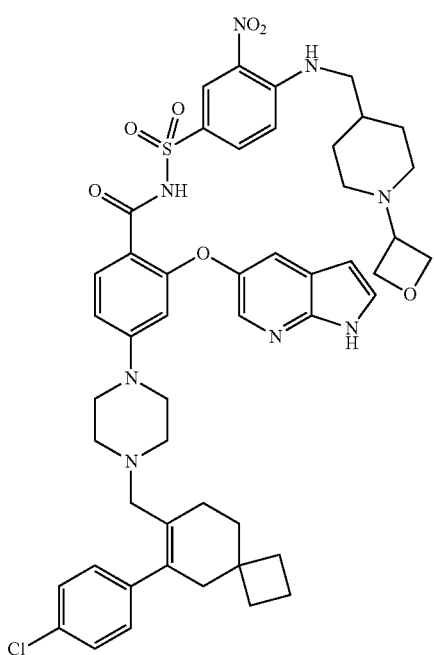 [SMILES: O=C(NS(=O)(=O)c1ccc(NCC2CCN(C3COC3)CC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(oxetan-3-yl)piperidin-4-yl)methyl)amino)phenyl)sulfonyl)benzamide |

TABLE 1-continued
| No. | Structure | Name |
|---|---|---|
| 19 | 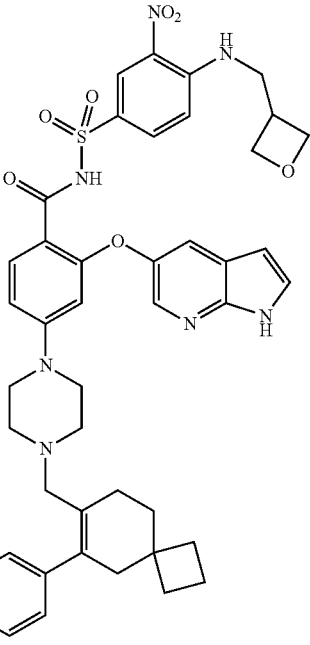 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((oxetan-3-ylmethyl)amino)phenyl)sulfonyl)benzamide |
| 20 | 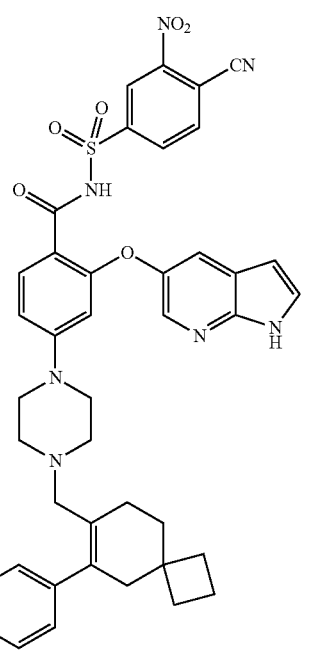 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-cyano-3-nitrophenyl)sulfonyl)benzamide |

TABLE 1-continued

| No. | Structure | Name |
|---|---|---|
| 21 | 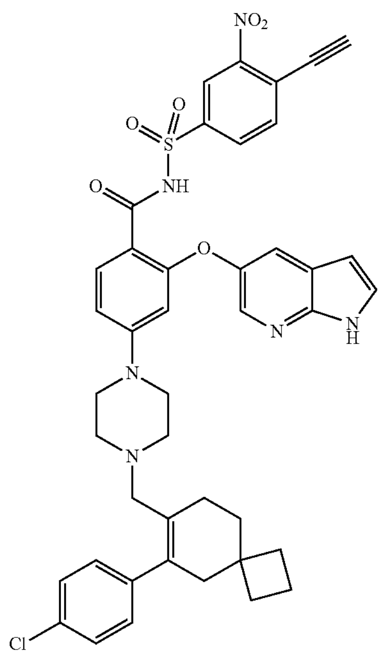 [SMILES: C#Cc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-ethynyl-3-nitrophenyl)sulfonyl)benzamide |

In some embodiments, the inhibitor of formulae I-A~I-i is one or more compounds of Table 1-A, or a pharmaceutically acceptable salt or solvate thereof.

TABLE 1-A

| No. | Structure | Name |
|---|---|---|
| 22 | 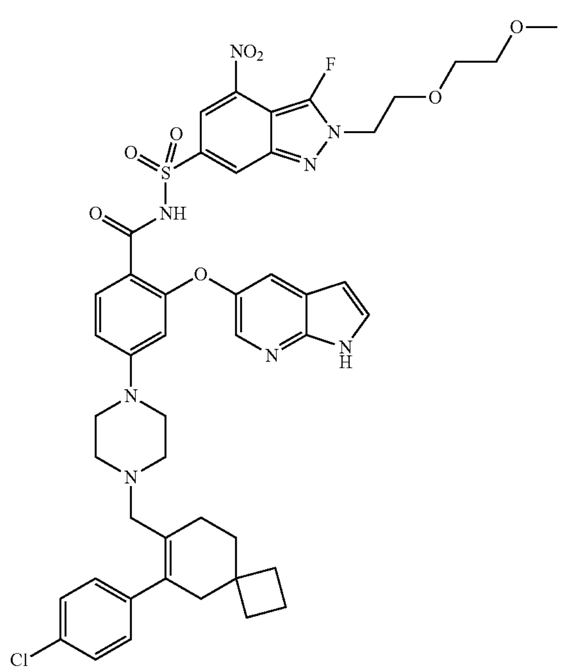 [SMILES: COCCOCCn1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2c1F] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-2-(2-(2-methoxyethoxy)ethyl)-4-nitro-2H-indazol-6-yl)sulfonyl)benzamide |

TABLE 1-A-continued

| No. | Structure | Name |
|---|---|---|
| 23 | 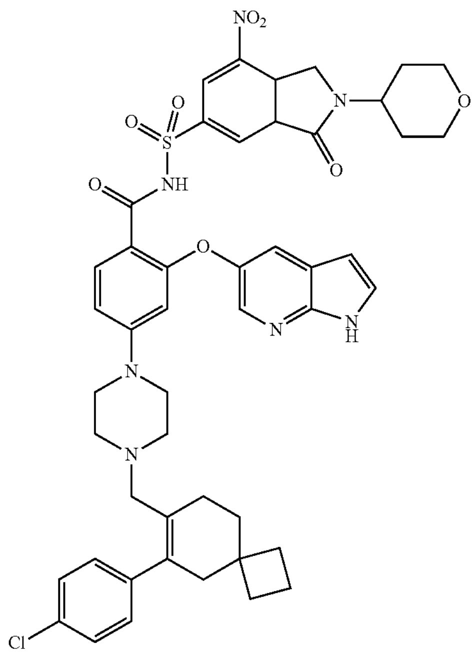 [SMILES: O=C(NS(=O)(=O)C1=CC2C(=O)N(C3CCOCC3)CC2C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-((6-(4-chlorophenyl)spiro[3.5]non-6-en-7-yl)methyl)piperazin-1-yl)-N-((7-nitro-3-oxo-2-(tetrahydro-2H-pyran-4-yl)-2,3,3a,7a-tetrahydro-1H-isoindol-5-yl)sulfonyl)benzamide |
| 24 | 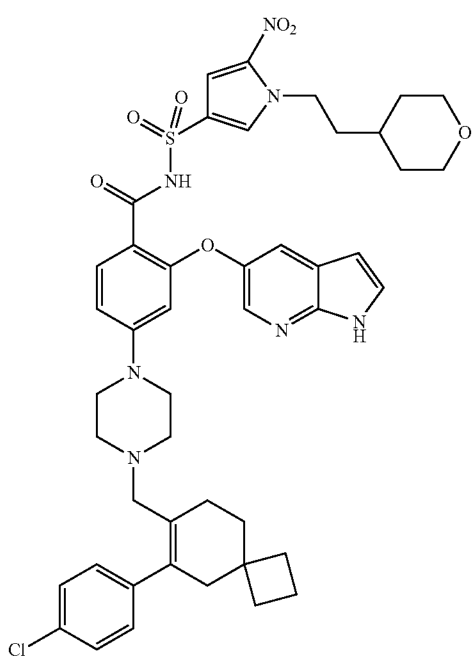 [SMILES: O=C(NS(=O)(=O)c1cc([N+](=O)[O-])n(CCC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-((6-(4-chlorophenyl)spiro[3.5]non-6-en-7-yl)methyl)piperazin-1-yl)-N-((5-nitro-1-(2-(tetrahydro-2H-pyran-4-yl)ethyl)-1H-pyrrol-3-yl)sulfonyl)benzamide |

TABLE 1-A-continued
| No. | Structure | Name |
|---|---|---|
| 25 | 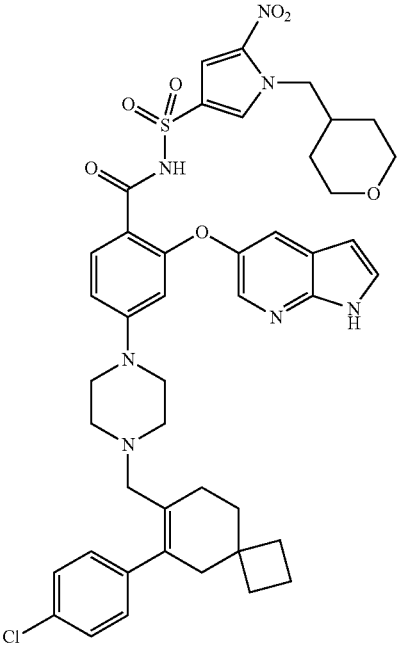 [SMILES: O=C(NS(=O)(=O)c1cc([N+](=O)[O-])n(CC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-((tetrahydro-2H-pyran-4-yl)methyl)-1H-pyrrol-3-yl)sulfonyl)benzamide |
| 26 | 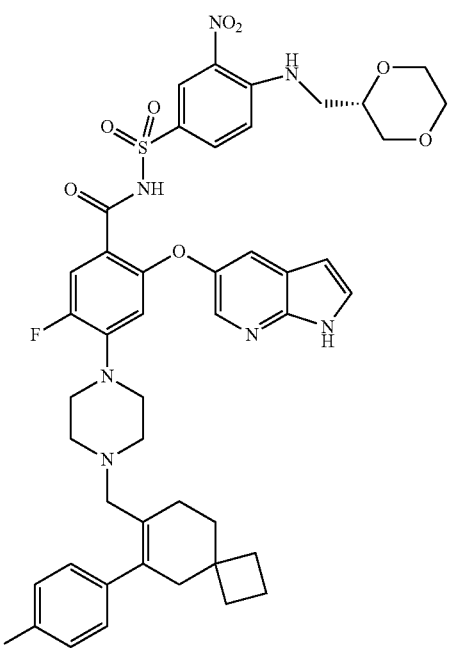 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |

TABLE 1-A-continued
| No. | Structure | Name |
|---|---|---|
| 27 | 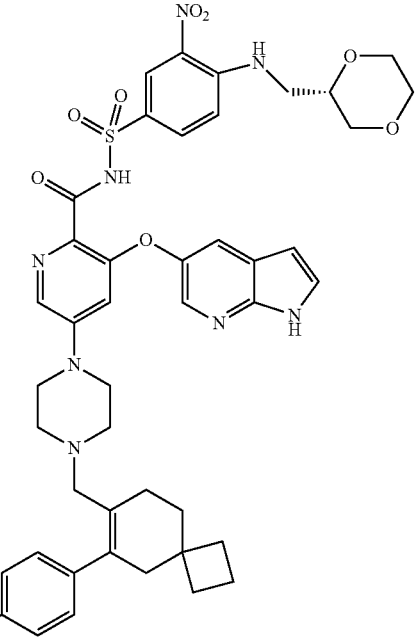 | (S)-N-((4-(((1,4-dioxan-2-yl)methyl)amino)-3-nitrophenyl)sulfonyl)-3-((1H-pyrrolo[2,3-b]pyridin-5-yl)oxy)-5-(4-((6-(4-chlorophenyl)spiro[3.5]non-6-en-7-yl)methyl)piperazin-1-yl)picolinamide |
| 28 | 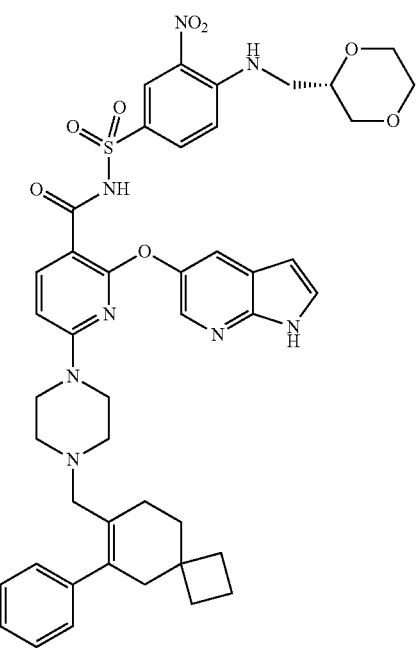 | (S)-N-((4-(((1,4-dioxan-2-yl)methyl)amino)-3-nitrophenyl)sulfonyl)-2-((1H-pyrrolo[2,3-b]pyridin-5-yl)oxy)-6-(4-((6-(4-chlorophenyl)spiro[3.5]non-6-en-7-yl)methyl)piperazin-1-yl)nicotinamide |

TABLE 1-A-continued

| No. | Structure | Name |
|---|---|---|
| 29 | 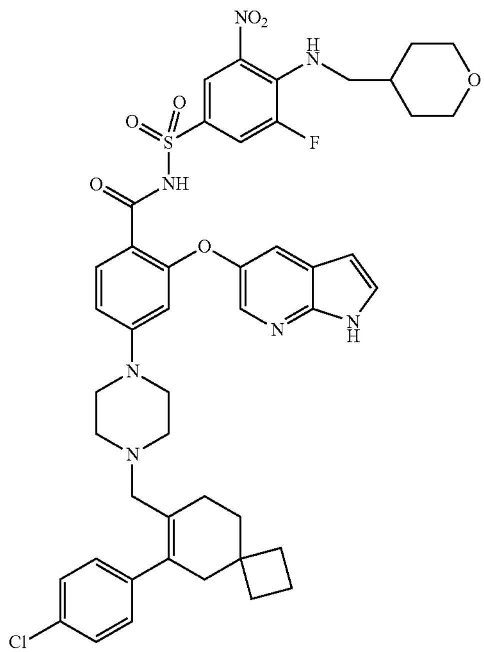 [SMILES: O=C(NS(=O)(=O)c1cc(F)c(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-5-nitro-4-(((tetrahydro-2H-pyran-4-yl)methyl)amino)phenyl)sulfonyl)benzamide |
| 30 | 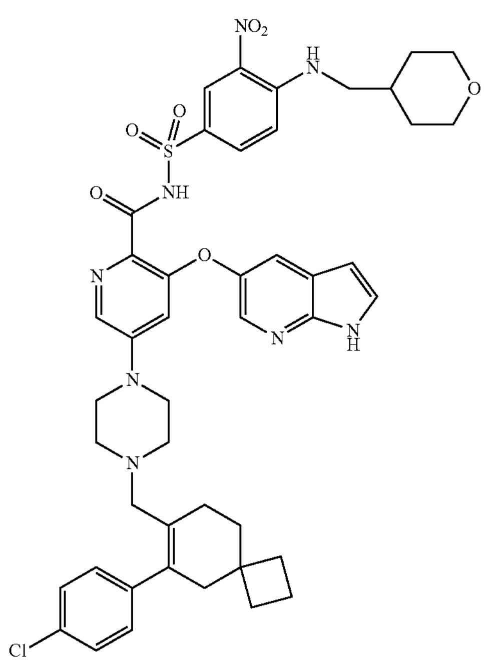 [SMILES: O=C(NS(=O)(=O)c1ccc(NCC2CCOCC2)c([N+](=O)[O-])c1)c1ncc(N2CCN(CC3=C(c4ccc(Cl)cc4)CC4(CCC4)CC3)CC2)cc1Oc1cnc2[nH]ccc2c1] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)picolinamide |

TABLE 1-A-continued

| No. | Structure | Name |
|---|---|---|
| 31 | 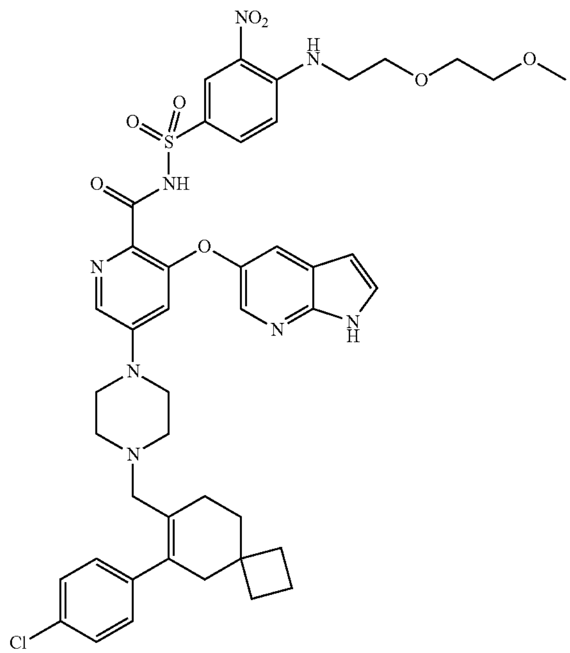 [SMILES: COCCOCCNc1ccc(S(=O)(=O)NC(=O)c2ncc(N3CCN(CC4=C(c5ccc(Cl)cc5)CC5(CCC5)CC4)CC3)cc2Oc2cnc3[nH]ccc3c2)cc1[N+](=O)[O-]] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |
| 32 | 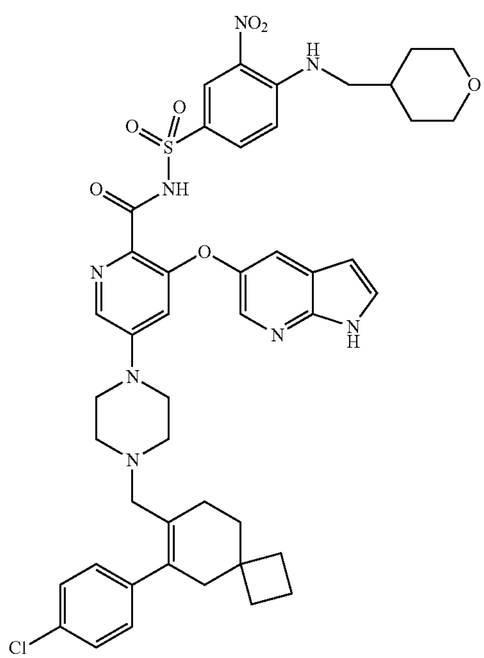 [SMILES: O=C(NS(=O)(=O)c1ccc(NCC2CCOCC2)c([N+](=O)[O-])c1)c1ncc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)nicotinamide |

TABLE 1-A-continued
| No. | Structure | Name |
|---|---|---|
| 33 | 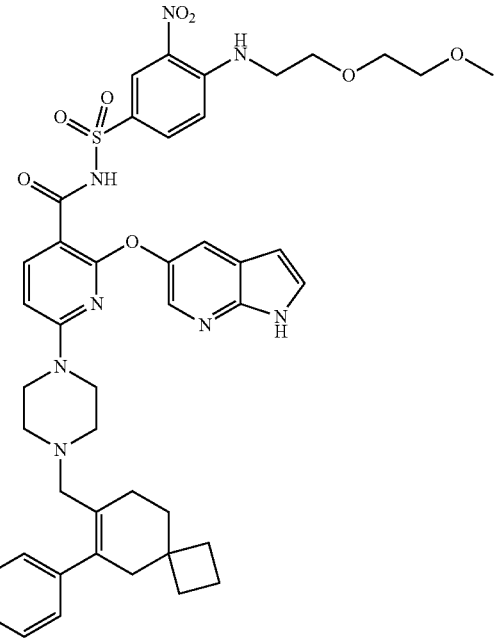 | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)nicotinamide |
| 34 | 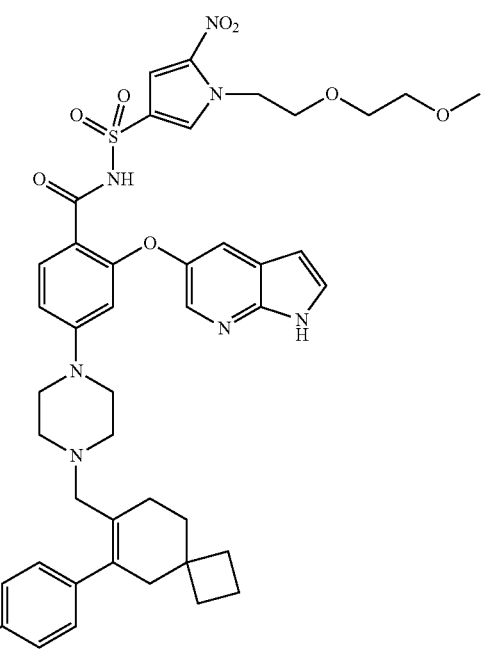 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-((2-(2-methoxyethoxy)ethyl)-5-nitro-1H-pyrrol-3-yl)sulfonyl)benzamide |

TABLE 1-A-continued
| No. | Structure | Name |
|---|---|---|
| 35 | 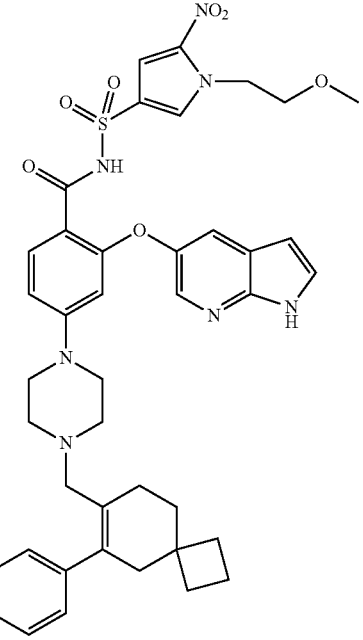 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-(2-methoxyethyl)-5-nitro-1H-pyrrol-3-yl)sulfonyl)benzamide |
| 36 | 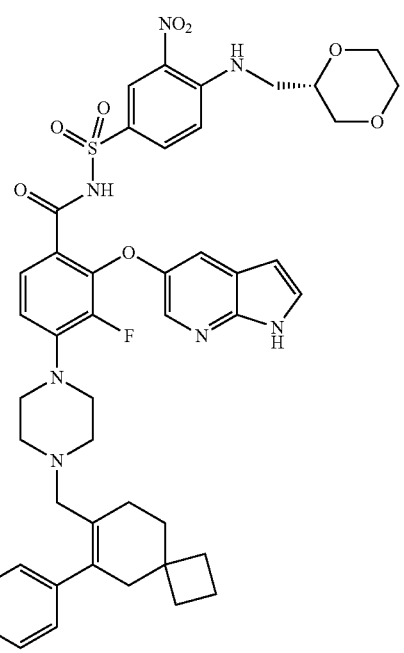 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluorobenzamide |

TABLE 1-A-continued
| No. | Structure | Name |
|---|---|---|
| 37 | 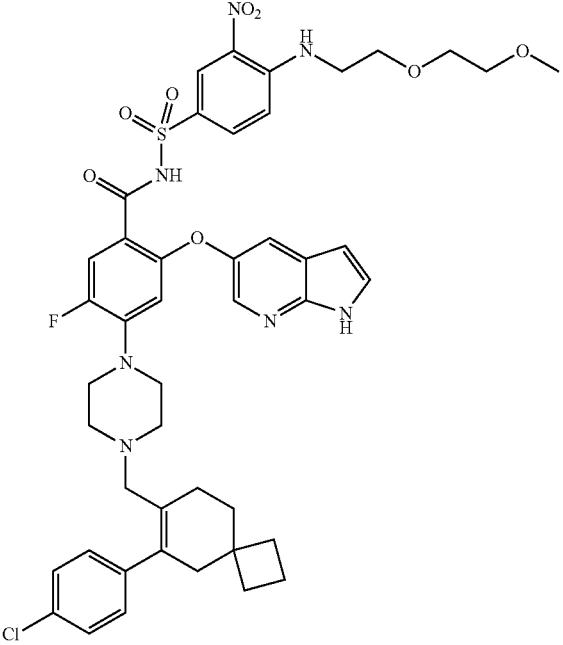 [SMILES: COCCOCCNc1ccc(S(=O)(=O)NC(=O)c2cc(F)c(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluoro-N-((4-((2-(2-methoxyethoxy)ethyl)amino)-3-nitrophenyl)sulfonyl)benzamide |
| 38 | 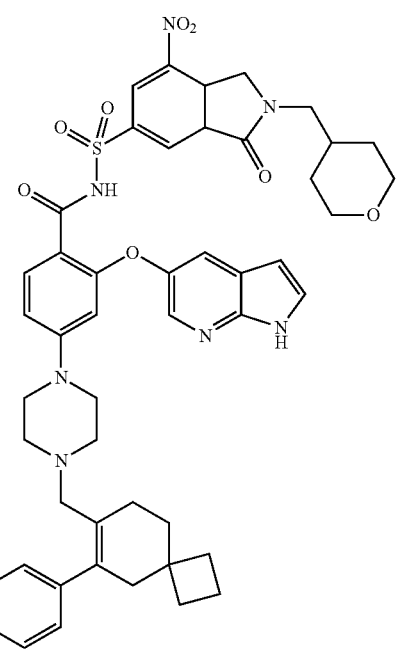 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-((tetrahydro-2H-pyran-4-yl)methyl)-2,3,3a,7a-tetrahydro-1H-isoindol-5-yl)sulfonyl)benzamide |

TABLE 1-A-continued

| No. | Structure | Name |
|---|---|---|
| 39 | 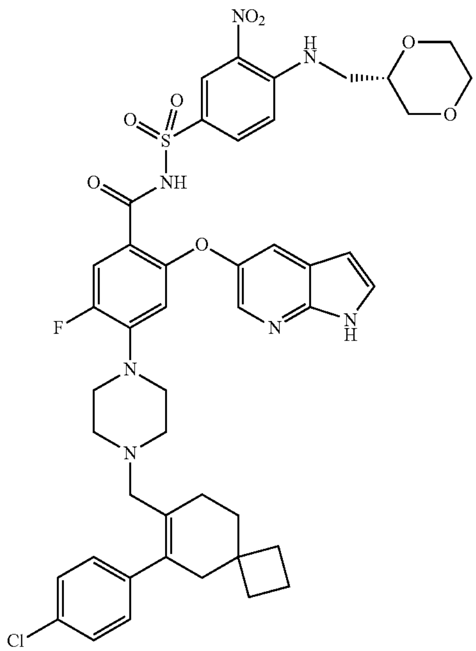 [SMILES: O=C(NS(=O)(=O)c1ccc(NC[C@H]2COCCO2)c([N+](=O)[O-])c1)c1cc(F)c(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |
| 40 | 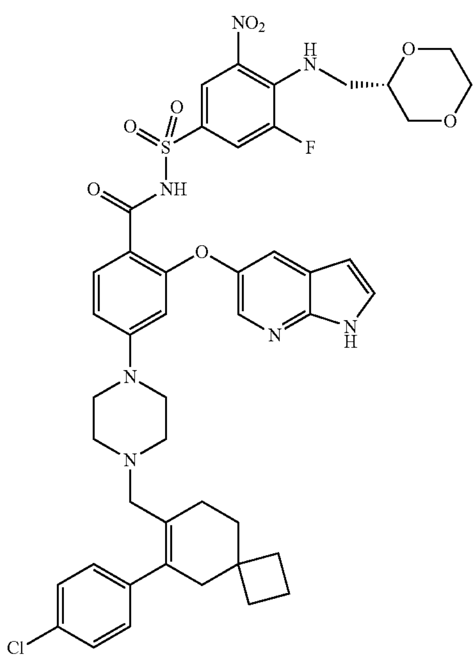 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-A-continued

| No. | Structure | Name |
|---|---|---|
| 41 | 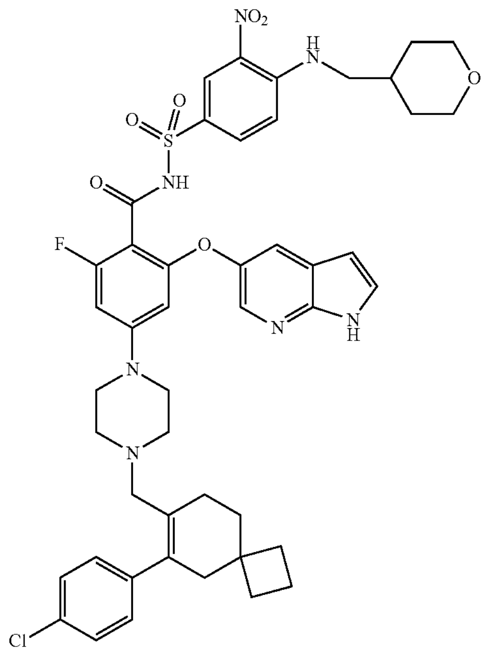 [SMILES: O=C(NS(=O)(=O)c1ccc(NCC2CCOCC2)c([N+](=O)[O-])c1)c1c(F)cc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-6-fluoro-N-((3-nitro-4-(((tetrahydro-2H-pyran-4-yl)methyl)amino)phenyl)sulfonyl)benzamide |
| 42 | 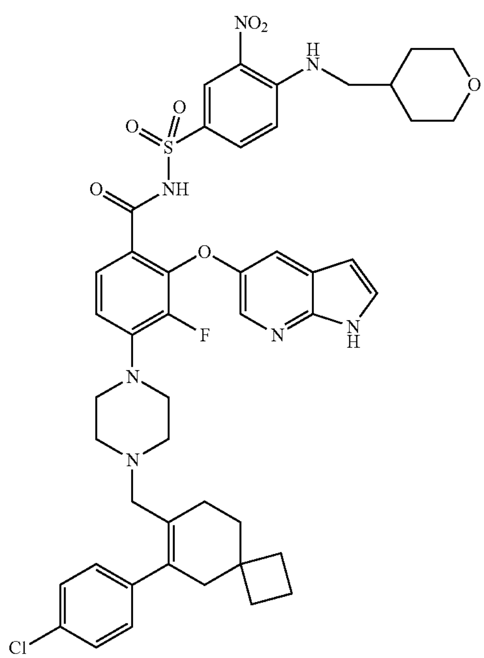 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)c(F)c1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((3-nitro-4-(((tetrahydro-2H-pyran-4-yl)methyl)amino)phenyl)sulfonyl)benzamide |

TABLE 1-A-continued
| No. | Structure | Name |
|---|---|---|
| 43 | 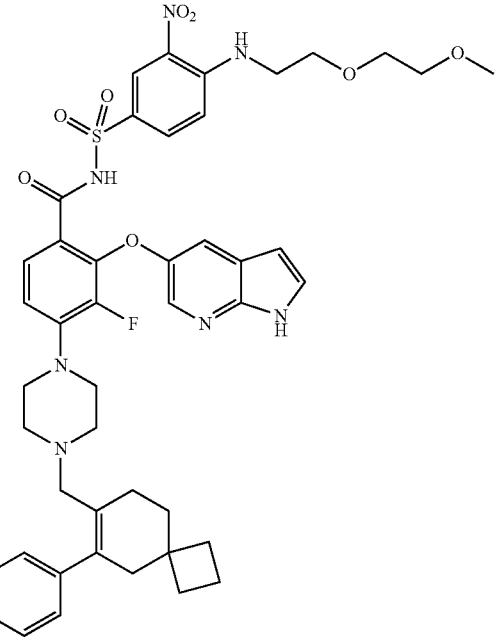 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((4-((2-(2-methoxyethoxy)ethyl)amino)-3-nitrophenyl)sulfonyl)benzamide |
| 44 | 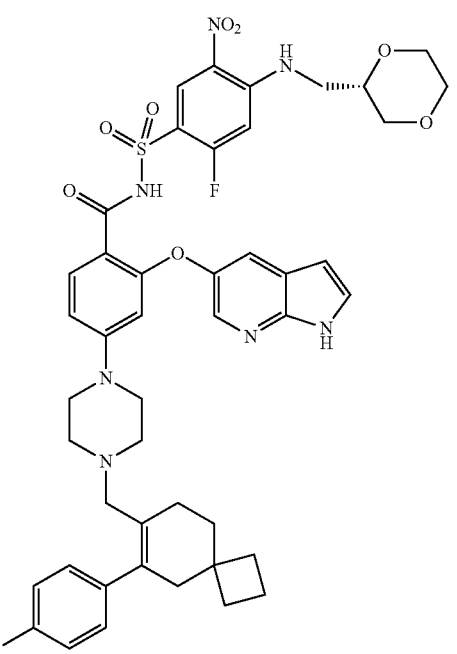 | (S)-N-((4-(((1,4-dioxan-2-yl)methyl)amino)-2-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-A-continued

| No. | Structure | Name |
|---|---|---|
| 45 | 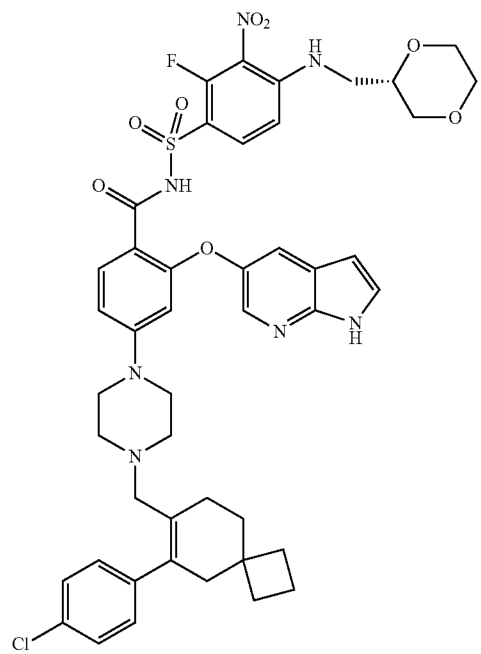 [SMILES: O=C(NS(=O)(=O)c1ccc(NC[C@H]2COCCO2)c([N+](=O)[O-])c1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 46 | 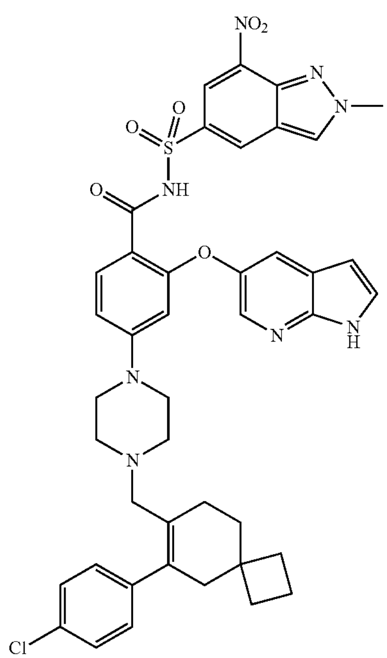 [SMILES: Cn1cc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-methyl-7-nitro-2H-indazol-5-yl)sulfonyl)benzamide |

TABLE 1-A-continued
| No. | Structure | Name |
|---|---|---|
| 47 | 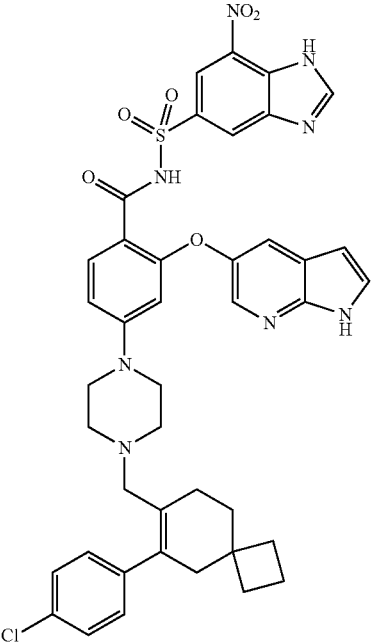 [SMILES: O=C(NS(=O)(=O)c1cc([N+](=O)[O-])c2[nH]cnc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1H-benzo[d]imidazol-5-yl)sulfonyl)benzamide |
| 48 | 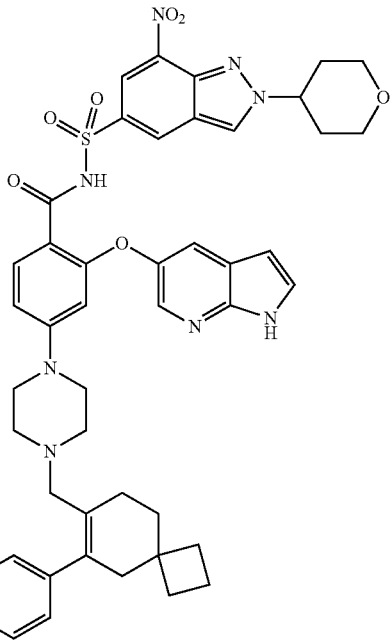 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(tetrahydro-2H-pyran-4-yl)-2H-indazol-5-yl)sulfonyl)benzamide |

TABLE 1-A-continued

| No. | Structure | Name |
|---|---|---|
| 49 | 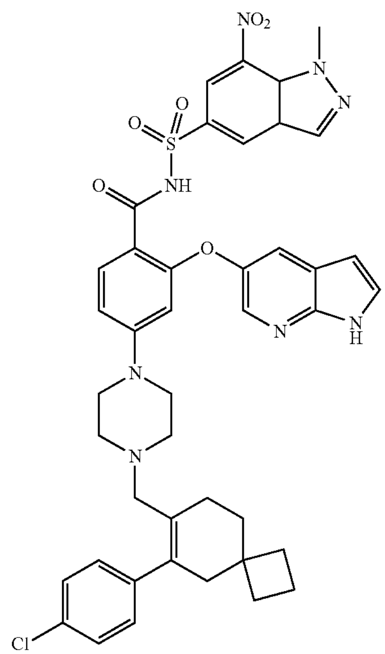 [SMILES: CN1N=CC2C=C(S(=O)(=O)NC(=O)c3ccc(N4CCN(CC5=C(c6ccc(Cl)cc6)CC6(CCC6)CC5)CC4)cc3Oc3cnc4[nH]ccc4c3)C=C([N+](=O)[O-])C21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-7-nitro-1H-indazol-5-yl)sulfonyl)benzamide |
| 50 | 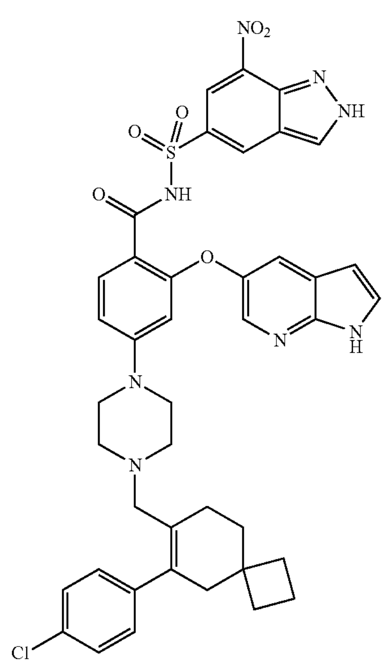 [SMILES: O=C(NS(=O)(=O)c1cc([N+](=O)[O-])c2n[nH]cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2H-indazol-5-yl)sulfonyl)benzamide |

TABLE 1-A-continued

| No. | Structure | Name |
|---|---|---|
| 51 | 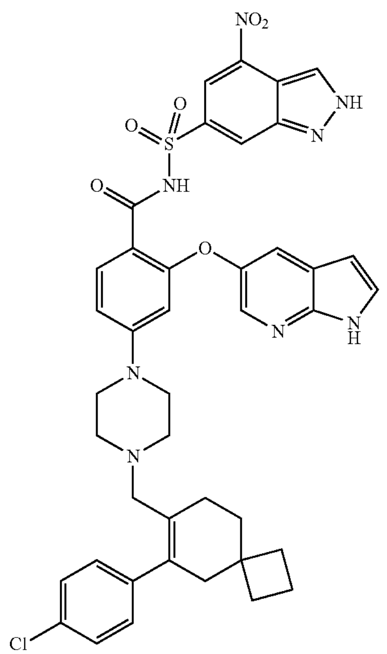 [SMILES: O=C(NS(=O)(=O)c1cc([N+](=O)[O-])c2c[nH]nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2H-indazol-6-yl)sulfonyl)benzamide |
| 52 | 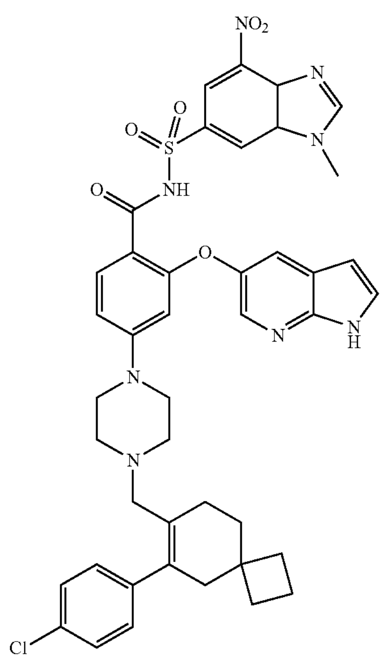 [SMILES: CN1C=NC2C([N+](=O)[O-])=CC(S(=O)(=O)NC(=O)c3ccc(N4CCN(CC5=C(c6ccc(Cl)cc6)CC6(CCC6)CC5)CC4)cc3Oc3cnc4[nH]ccc4c3)=CC21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-4-nitro-1H-benzo[d]imidazol-6-yl)sulfonyl)benzamide |

TABLE 1-A-continued
| No. | Structure | Name |
|---|---|---|
| 53 | 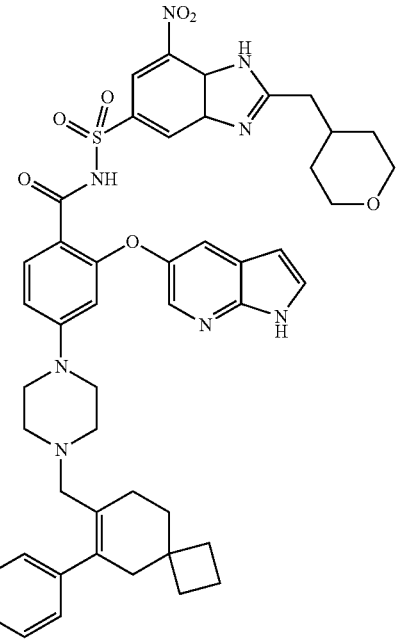 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-1H-benzo[d]imidazol-5-yl)sulfonyl)benzamide |
| 54 | 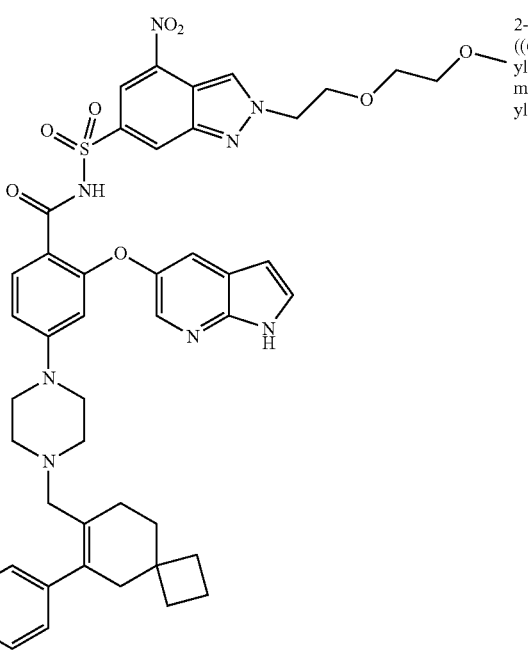 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-(2-methoxyethoxy)ethyl)-4-nitro-2H-indazol-6-yl)sulfonyl)benzamide |

| No. | Structure | Name |
|---|---|---|
| 55 | 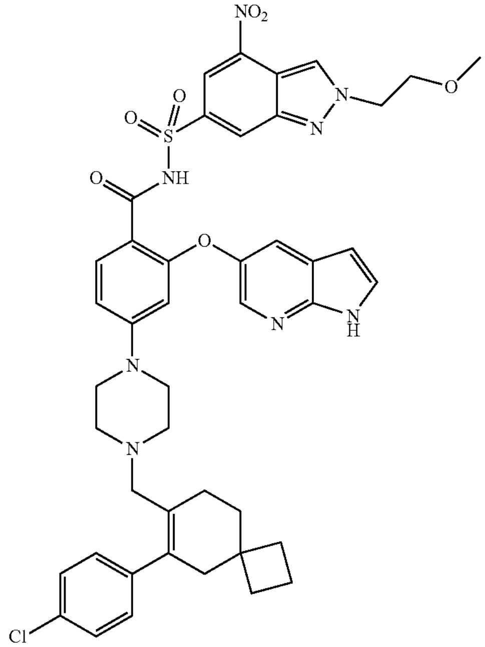 [SMILES: COCCn1cc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-methoxyethyl)-4-nitro-2H-indazol-6-yl)sulfonyl)benzamide |
| 56 | 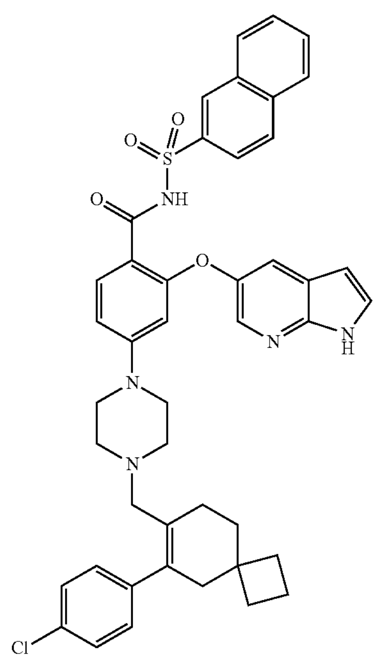 [SMILES: O=C(NS(=O)(=O)c1ccc2ccccc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-(naphthalene-2-ylsulfonyl)benzamide |

In some embodiments, the inhibitor of formulae I-A~I-i is a compound of Table 1-B, or a pharmaceutically acceptable salt or solvate thereof.

TABLE 1-B

| No. | Structure | Name |
|---|---|---|
| 57 | 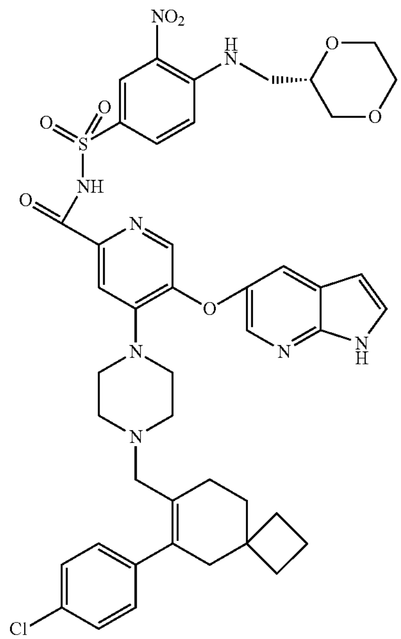 [SMILES: O=C(NS(=O)(=O)c1ccc(NC[C@H]2COCCO2)c([N+](=O)[O-])c1)c1cc(N2CCN(CC3=C(c4ccc(Cl)cc4)CC4(CCC4)CC3)CC2)c(Oc2cnc3[nH]ccc3c2)cn1] | (S)-N-((4-(((1,4-dioxan-2-yl)methyl)amino)-3-nitrophenyl)sulfonyl)-5-((1H-pyrrolo[2,3-b]pyridin-5-yl)oxy)-4-(4-((6-(4-chlorophenyl)spiro[3.5]non-6-en-7-yl)methyl)piperazin-1-yl)picolinamide |

In some embodiments, the inhibitor of formulae I-A~I-i is a compound selected from one or more of the compounds of Table 1-C or a pharmaceutically acceptable salt or solvate thereof.

TABLE 1-C

| No. | Structure | Name |
|---|---|---|
| 58 | 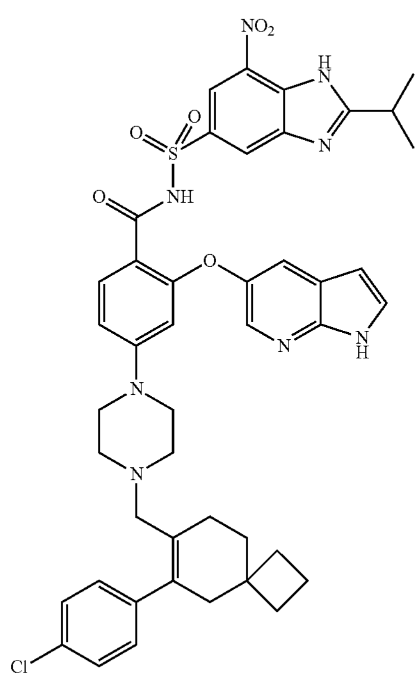 [SMILES: CC(C)c1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2[nH]1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-isopropyl-7-nitro-1H-benzo[d]imidazol-5-yl)sulfonyl)benzamide |

TABLE 1-C-continued

| No. | Structure | Name |
| --- | --- | --- |
| 59 | 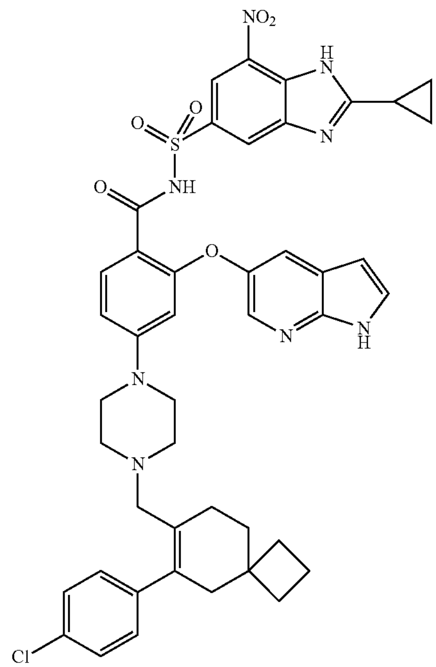 [SMILES: O=C(NS(=O)(=O)c1cc([N+](=O)[O-])c2[nH]c(C3CC3)nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-cyclopropyl-7-nitro-1H-benzo[d]imidazol-5-yl)sulfonyl)benzamide |
| 60 | 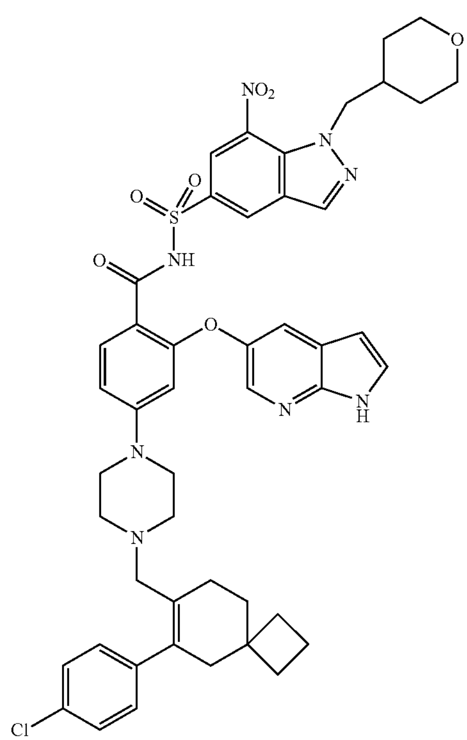 [SMILES: O=C(NS(=O)(=O)c1cc([N+](=O)[O-])c2c(cnn2CC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1-((tetrahydro-2H-pyran-4-yl)methyl)-1H-indazol-5-yl)sulfonyl)benzamide |

TABLE 1-C-continued
| No. | Structure | Name |
|---|---|---|
| 61 | 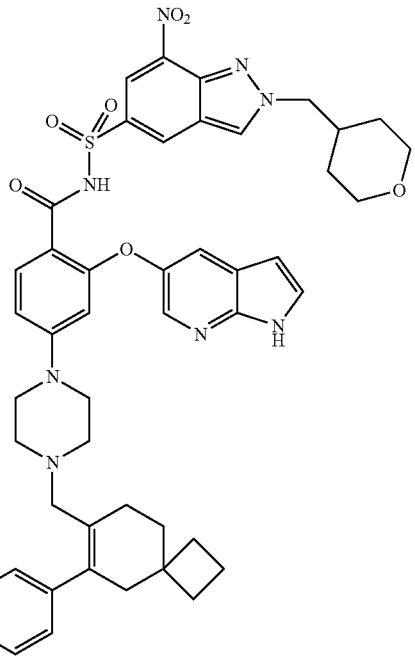 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-2H-indazol-5-yl)sulfonyl)benzamide |
| 62 | 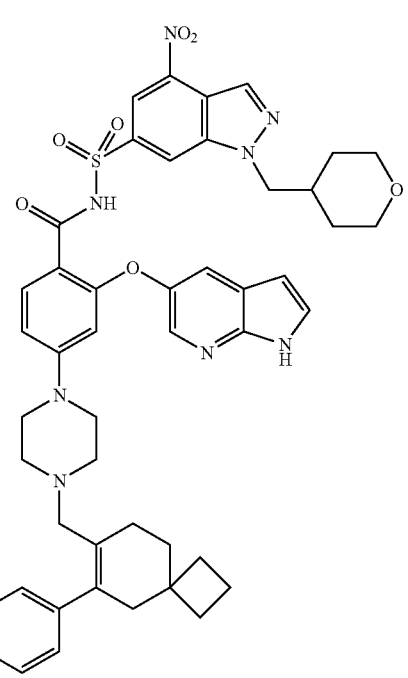 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-1-((tetrahydro-2H-pyran-4-yl)methyl)-3a,7a-dihydro-1H-indazol-6-yl)sulfonyl)benzamide |

TABLE 1-C-continued

| No. | Structure | Name |
| --- | --- | --- |
| 63 | 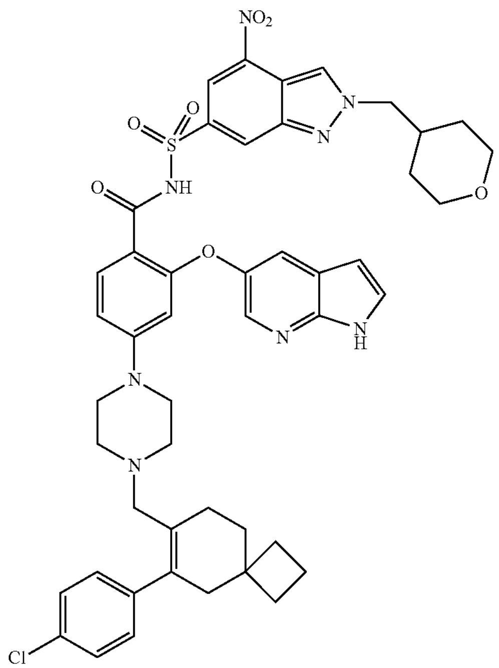 [SMILES: O=C(NS(=O)(=O)c1cc([N+](=O)[O-])c2cn(CC3CCOCC3)nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2-((tetrahydro-2H-pyran-4-yl)methyl)-2H-indazol-6-yl)sulfonyl)benzamide |
| 64 | 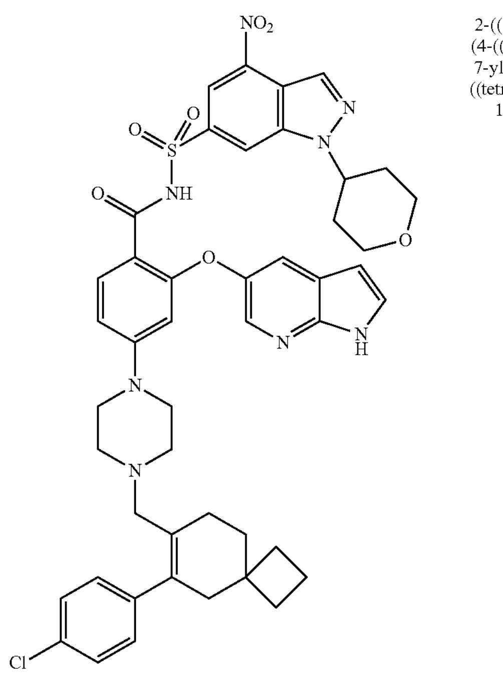 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-1-((tetrahydro-2H-pyran-4-yl)-3a,7a-dihydro-1H-indazol-6-yl)sulfonyl)benzamide |

TABLE 1-C-continued

| No. | Structure | Name |
|---|---|---|
| 65 | 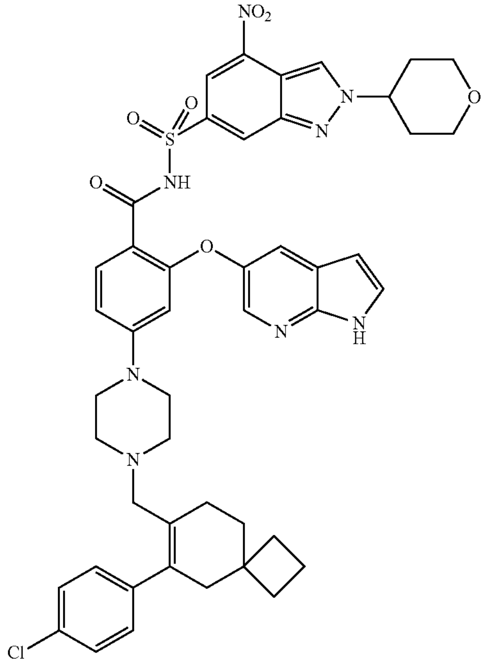 [SMILES: O=C(NS(=O)(=O)c1cc([N+](=O)[O-])c2cn(C3CCOCC3)nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2-(tetrahydro-2H-pyran-4-yl)-2H-indazol-6-yl)sulfonyl)benzamide |
| 66 | 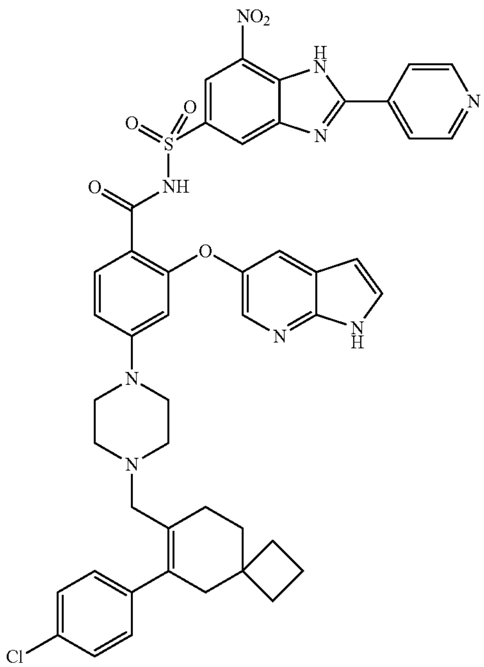 [SMILES: O=C(NS(=O)(=O)c1cc([N+](=O)[O-])c2[nH]c(-c3ccncc3)nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(pyridin-4-yl)-1H-benzo[d]imidazol-5-yl)sulfonyl)benzamide |

The compounds of the above general formulae I-A, I-b~I-i and the individual specific compounds used in the present invention have been disclosed in WO2018/027097A1, and can be synthesized and tested for activity according to the method described in WO20318/0270971A1, the entire contents of which are incorporated herein by reference.

Compounds of the above general formulae I-A, I-b~I-i for use in the present invention have a Bcl-2 and/or a Bcl-xL IC50 of less than about 10 μM, e.g., less than about 5 μM, less than about 1 μM, less than about 0.5 μM, less than about 0.1 μM, less than about 0.05 μM, less than about 0.025 μM, less than about 0.010 μM, less than about 0.005 μM, less than about 0.0025 μM, less than about 0.001 μM of Bcl-2 and/or Bcl-xL IC50. In particular, the compounds listed in Table 1 and Tables 1-A, 1-B and 1-C, exhibit selective inhibitory activity against Bcl-2.

In some embodiments, the Bcl-2/Bcl-xL inhibitor is a compound having the general formula (I), (II), (III), or (IV):

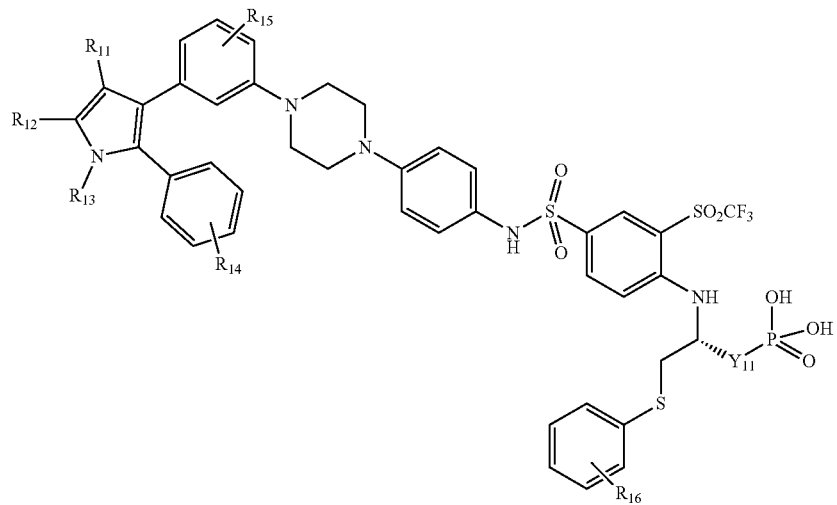
(I)
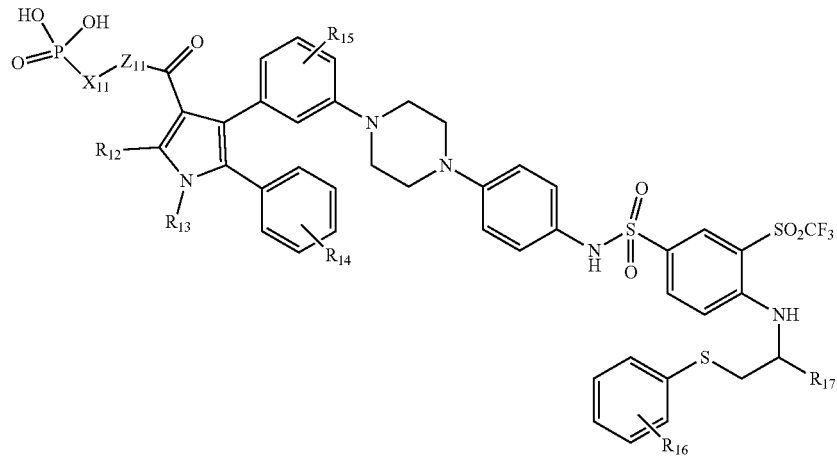
(II)
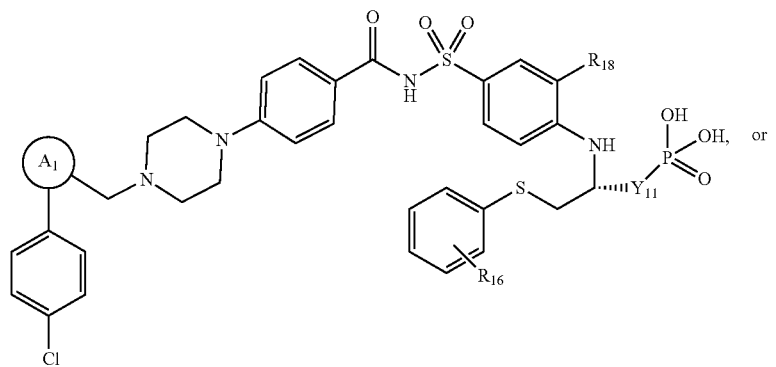
(III)

-continued (IV)

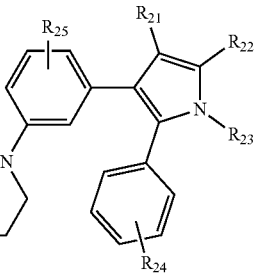

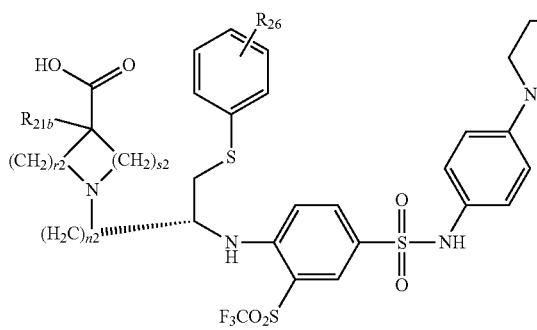

wherein ring $A_1$ is

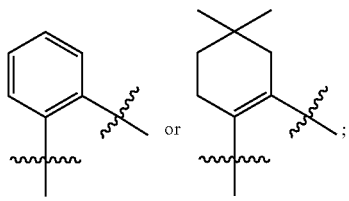 or 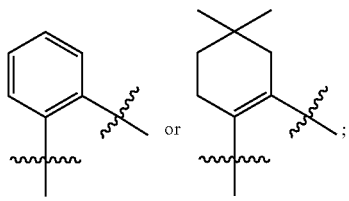 ;

Substituted or unsubstituted $X_{11}$ is selected from the group consisting of alkylene, alkenylene, cycloalkylene, cycloalkenylene and heterocycloalkylene;

$Y_{11}$ is selected from the group consisting of $(CH_2)_nN(R_{11}{}^a)$ and

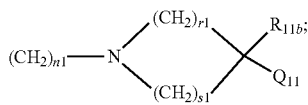

$Q_{11}$ is selected from the group consisting of O, $O(CH_2)_{1-3}$, $NR_{11}{}^c$, $NR_{11}{}^c(C_{1-3}\text{alkylene})$, $OC(=O)(C_{1-3}\text{alkylene})$, $C(=O)O$, $C(=O)O(C_{1-3}\text{alkylene})$, $NHC(=O)(C_{1-3}\text{alkylene})$, $C(=O)NH$ and $C(=O)NH(C_{1-3}\text{alkylene})$;

$Z_{11}$ is O or $NR_{11}{}^c$;

$R_{11}$ and $R_{12}$ are independently selected from the group consisting of H, CN, $NO_2$, halogen, alkyl, cycloalkyl, alkenyl, cycloalkenyl, alkynyl, aryl, heteroaryl, heterocycloalkyl, $OR_1'$, $SR_1'$, $NR_1'R_1'''$, $COR_1'$, $CO_2R_1'$, $OCOR_1'$, $CONR_1'R_1''$, $CONR_1'SO_2R_1''$, $NR_1'COR_1''$, $NR_1'CONR_1''R_1'''$, $NR_1'C=SNR_1''R_1'''$, $NR_1'SO_2R_1''$, $SO_2R_1'$ and $SO_2NR_1'R_1''$;

$R_{13}$ is selected from the group consisting of H, alkyl, cycloalkyl, alkenyl, cycloalkenyl, alkynyl, aryl, heteroaryl, heterocycloalkyl, $OR_1'$, $NR_1'R_1''$, $OCOR_1'$, $CO_2R_1'$, $COR_1'$, $CONR_1'R_1''$, $CONR_1'SO_2R_1''$, $C_{1-3}\text{alkyleneCH(OH)CH}_2\text{OH}$, $SO_2R_1'$ and $SO_2NR_1'R_1''$;

$R_1'$, $R_1''$ and $R_1'''$ are each independently H, alkyl, cycloalkyl, alkenyl, cycloalkenyl, alkynyl, aryl, heteroaryl, $C_{1-3}\text{alkyleneheterocycloalkyl}$ or heterocycloalkyl;

$R_1'$ and $R_1''$ or $R_1''$ and $R_1'''$ may together with the atoms to which they are attached form a 3-7 membered ring;

$R_{14}$ is hydrogen, halogen, $C_{1-3}\text{alkyl}$, $CF_3$ or CN;

$R_{15}$ is hydrogen, halogen, $C_{1-3}\text{alkyl}$, substituted $C_{1-3}\text{alkyl}$, hydroxyalkyl, alkoxy or substituted alkoxy;

$R_{16}$ is selected from the group consisting of H, CN, $NO_2$, halogen, alkyl, cycloalkyl, alkenyl, cycloalkenyl, alkynyl, aryl, heteroaryl, heterocycloalkyl, $OR_1'$, $SR_1'$, $NR_1'R_1''$, $CO_2R_1'$, $OCOR_1'$, $CONR_1'R_{19}'''$, $CONR_1'SO_2R_1''$, $NR_1'COR_1''$, $NR_1'CONR_1''R_1'''$, $NR_1'C=SNR_1''R_1'''$, $NR_1'SO_2R_1''$, $SO_2R_1'$ and $SO_2NR_1'R_1''$;

Substituted or unsubstituted $R_{17}$ is selected from the group consisting of hydrogen, alkyl, alkenyl, $(CH_2)_{0-3}$-cycloalkyl, $(CH_2)_{0-3}$-cycloalkenyl, $(CH_2)_{0-3}$-heterocycloalkyl, $(CH_2)_{0-3}\text{aryl}$, and $(CH_2)_{0-3}\text{heteroaryl}$;

$R_{18}$ is selected from the group consisting of hydrogen, halogen, $NO_2$, CN, $CF_3SO_2$, and $CF_3$;

$R_{11}{}^a$ is selected from the group consisting of hydrogen, alkyl, heteroalkyl, alkenyl, hydroxyalkyl, alkoxy, substituted alkoxy, cycloalkyl, cycloalkenyl and heterocycloalkyl;

$R_{11}{}^b$ is hydrogen or alkyl;

$R_{11}{}^c$ is selected from the group consisting of hydrogen, alkyl, substituted alkyl, hydroxyalkyl, alkoxy, and substituted alkoxy; and $n_1$, $r_1$ and s1 are each independently 1, 2, 3, 4, 5 or 6;

$R_{21}$ is $SO_2R_2'$;

$R_{22}$ is alkyl, preferably $C_{1-4}\text{alkyl}$, more preferably methyl, propyl or isopropyl;

$R_{23}$ is alkyl, preferably $C_{1-4}\text{alkyl}$, more preferably methyl, propyl or isopropyl;

$R_{24}$ is halogen, preferably fluorine, chlorine;

$R_{25}$ is halogen, preferably fluorine, chlorine;

$R_{26}$ is selected from the group consisting of H, halogen and alkyl, preferably fluoro, chloro, $C_{1-4}\text{alkyl}$, more preferably methyl, propyl or isopropyl;

$R_{21b}$ is H or alkyl, preferably $C_{1-4}\text{alkyl}$, more preferably methyl, propyl or isopropyl;

$n_2$, $r_2$ and $s_2$ are each independently 1, 2, 3, 4, 5 or 6, more preferably $r_2$ and $s_2$ are both 2 and $n_2$ is 3, 4 or 5, more preferably $n_2$, $r_2$ and $s_2$ are all 2; and $R_2'$ is alkyl, preferably $C_{1-4}\text{alkyl}$, more preferably methyl, propyl or isopropyl.

In the above general formula (I), (II) or (III), in some embodiments, $R_{11}$ and $R_{12}$ or $R_{12}$ and $R_{13}$ may together form a ring. In other embodiments, $R_1'$ and $R_1''$ or $R_1''$ and $R_1'''$ can together with the atoms to which they are attached form a 3-7 membered ring.

In some preferred embodiments, $X_{11}$ is alkylene, and in preferred embodiments, $C_{1-3}$alkylene.

In some embodiments, $Y_{11}$ is

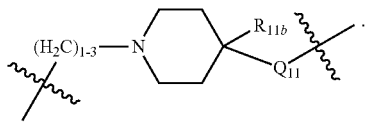

In a preferred embodiment, $n_1$ is 2. In other preferred embodiments, $R_{11b}$ is hydrogen or $C_{1-3}$alkyl.

In other preferred embodiments, $Q_{11}$ is O, $O(CH_2)_{1-3}$, $C(=O)O(CH_2)_{1-3}$, $OC(=O)(CH_2)_{1-3}$, or $C(=O)O(C_3H_7)_{1-3}$. In some embodiments, $Q_{11}$ is O, $OCH_2$, $C(=O)OCH_2$, $C(=O)O(CH_2)_2$, $C(=O)O(CH_2)_3$, $OC(=O)CH_2$, or $C(=O)O(CH(CH_3)CH_2)$.

In some embodiments, $Z_{11}$ is O, NH or $N(C_{1-3}$alkyl). In preferred embodiments, $Z_{11}$ is O, NH or $NCH_3$.

In some embodiments, $R_{11}$ is $SO_2R_1'$, $SO_2NR_1'R_1''$, $NR_1'SOR_1''$, H or alkyl. In some preferred embodiments, $R_{11}$ is $SO_2(C_{1-3}$alkyl), $SO_2N(C_{1-3}$alkyl)$_2$, $NHSO_2(C_{1-3}$alkyl), H, or $C_{1-3}$alkyl. One preferred embodiment of $R_1$ is $SO_2CH_3$.

In some embodiments, $R_{12}$ and $R_{13}$ are independently H, $C_{1-3}$alkyl or cycloalkyl. $R_{12}$ may also be halogen. In some preferred embodiments, $R_{12}$ and $R_{13}$ are independently methyl, ethyl, n-propyl, isopropyl, cyclopentyl, or cyclohexyl. $R_{12}$ can also be Cl or F.

In some embodiments, $R_{14}$ is H or halogen, preferably H, Cl or F. In other embodiments, $R_{15}$ is H, halogen or $C_{1-3}$alkyl, preferably H, methyl, ethyl, n-propyl, isopropyl, F or Cl. In other embodiments, $R_{16}$ is H, halogen, alkyl, or cycloalkyl. In some preferred embodiments, $R_{16}$ is H, F, Cl, $C_{1-3}$alkyl, cyclopentyl, or cyclohexyl.

In some embodiments, $R_{17}$ is $(CH_2)_{0-3}$-cycloalkyl or $(CH_2)_{0-3}$-heterocycloalkyl. In a preferred embodiment, $R_{17}$ is $(CH_2)_{0-3}$-cycloalkyl, optionally substituted with —OH. In one embodiment, $R_{17}$ is

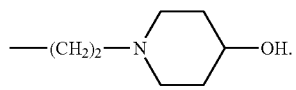

In some embodiments, $R_{18}$ is $CF_3SO_2$ or $CF_3$. In various embodiments, $R_{11a}$, $R_{11b}$, and $R_{11c}$ are each independently H or $C_{1-3}$alkyl.

For the above Bcl-2/Bcl-xL inhibitors of the general formulae (I)~(IV) of the present invention, the term "alkyl" refers to a straight or branched chain saturated $C_{1-10}$hydrocarbon group, non-limiting examples of which include methyl, ethyl and straight or branched propyl, butyl, pentyl, hexyl, heptyl, octyl, nonyl and decyl. The term "$C_n$" means that the alkyl group has n carbon atoms. The term "alkylene" refers to an alkyl group having a substituent. Alkyl, such as methyl, or alkylene, such as —$CH_2$— may be unsubstituted or substituted, for example, with halogen, trifluoromethyl, trifluoromethoxy, hydroxy, alkoxy, nitro, cyano, alkylamino or amino.

For the above Bcl-2/Bcl-xL inhibitors of the general formulae (I)~(IV) of the present invention, the terms "alkenyl" and "alkenylene" are defined identically as the terms "alkyl" and "alkylene", except that they contain a carbon-carbon double bond. The terms "alkynyl" and "alkynylene" are defined identically as "alkyl" and "alkylene" except that they contain a carbon-carbon triple bond.

For the above Bcl-2/Bcl-xL inhibitors of the general formulae (I)~(IV) of the present invention, the terms "aryl" refers to a monocyclic or polycyclic aromatic radical, preferably a monocyclic or bicyclic aromatic radical. Unless otherwise specified, an aryl group may be unsubstituted or substituted by one or more, especially 1-4 groups independently selected from, for example, halogen, alkyl, alkenyl, —$OCF_3$, —$CF_3$, —$NO_2$, —CN, —NC, —OH, alkoxy, amino, alkylamino, —$CO_2H$, —$CO_2$alkyl, —OCOalkyl, aryl and heteroaryl.

For the above Bcl-2/Bcl-xL inhibitors of the general formulae (I)~(IV) according to the invention, the term "heteroaryl" refers to a monocyclic or bicyclic ring system which comprises one or two aromatic rings and at least one nitrogen, oxygen or sulfur atom in the aromatic ring. Unless otherwise specified, heteroaryl groups may be unsubstituted or substituted by one or more, in particular 1 to 4, substituents selected, for example, from halogen, alkyl, alkenyl, —$OCF_3$, —$CF_3$, —$NO_2$, —CN, —NC, —OH, alkoxy, amino, alkylamino, —$CO_2H$, —$CO_2$alkyl, —OCOalkyl, aryl and heteroaryl.

For the above Bcl-2/Bcl-xL inhibitors of the general formulae (I)~(IV) of the present invention, the term "cycloalkyl" refers to a monocyclic aliphatic ring containing 3 to 8 carbon atoms. The term "heterocycloalkyl" refers to a monocyclic or bicyclic ring system containing at least one nitrogen, oxygen, or sulfur atom in the ring system. The terms "heteroaryl" and "heterocycloalkyl" include ring systems containing at least one oxygen, nitrogen or sulfur atom, and include ring systems containing oxygen and nitrogen atoms, oxygen and sulfur atoms, nitrogen and sulfur atoms, and nitrogen, oxygen and sulfur atoms.

In some embodiments, the Bcl-2/Bcl-xL inhibitor of general formulae (I)~(IV) is selected from the compounds in Table 2 below, or a pharmaceutically acceptable salt thereof, or a solvate thereof.

TABLE 2

| No. | Structure |
|---|---|
| 67 | 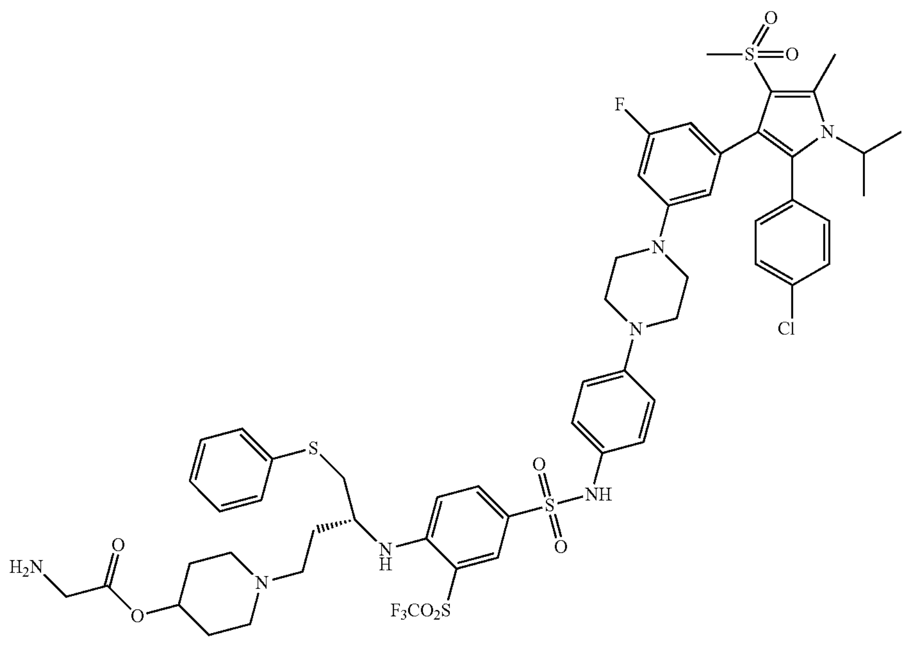 |
| 68 | 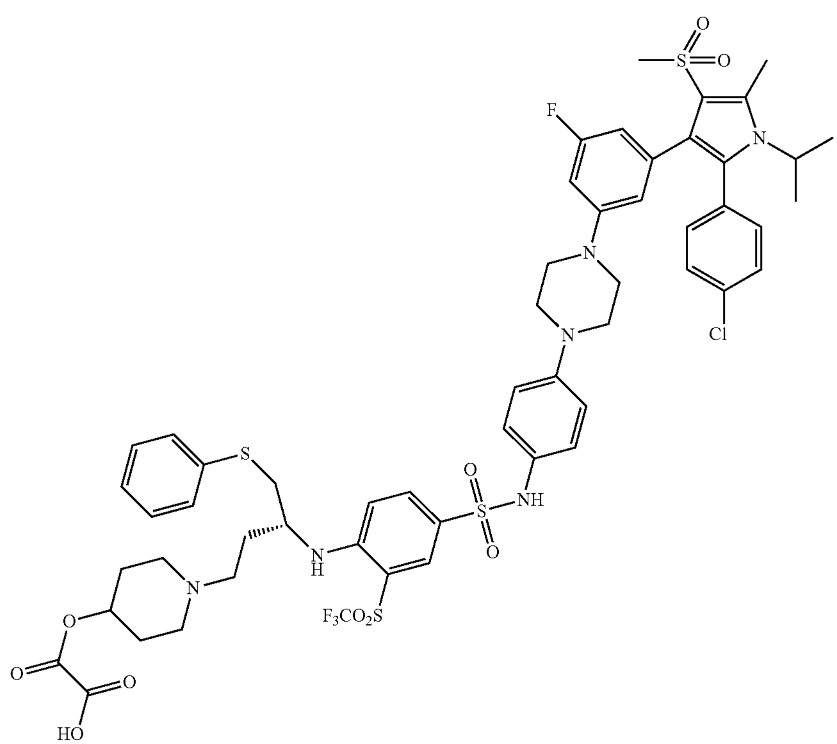 |

TABLE 2-continued
| No. | Structure |
|---|---|
| 69 | 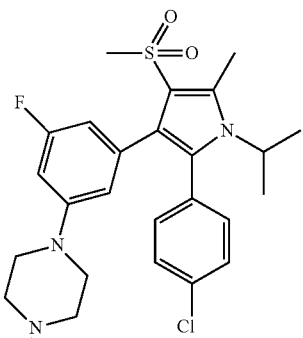 |
| 70 | 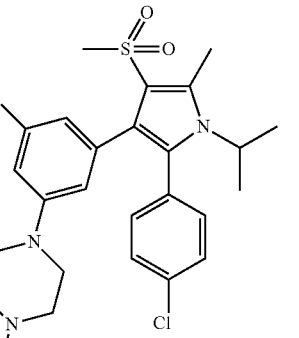 |

TABLE 2-continued
| No. | Structure |
|---|---|
| 71 | 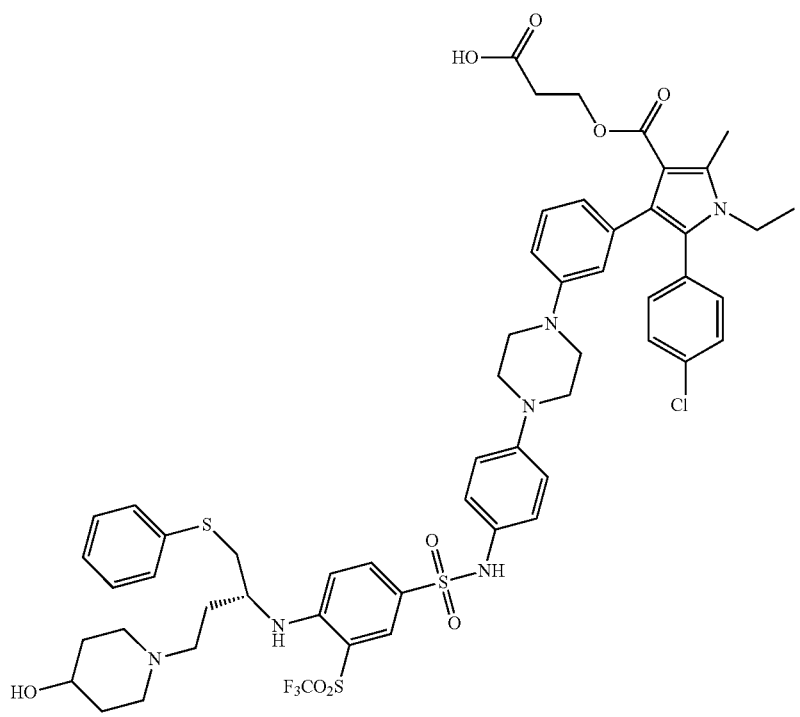 |
| 72 | 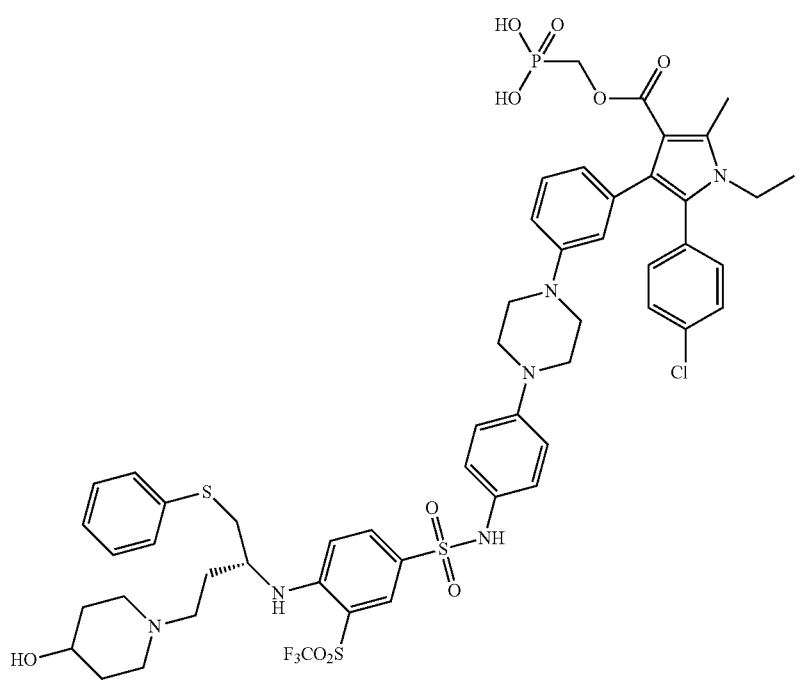 |

111 112
TABLE 2-continued
| No. | Structure |
|-----|-----------|
| 73  | 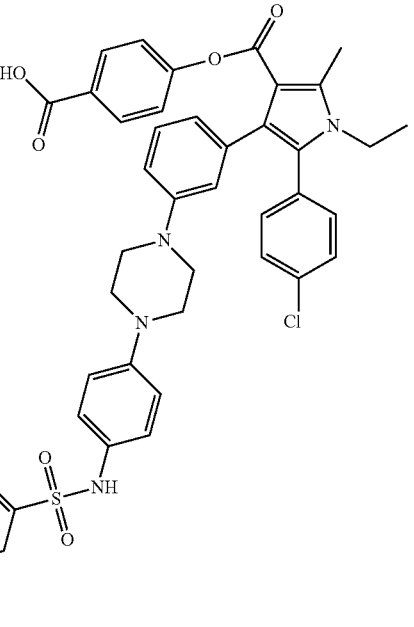 |
| 74  | 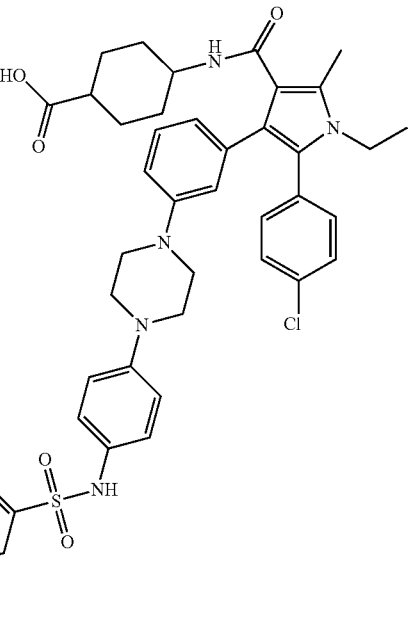 |

TABLE 2-continued
| No. | Structure |
|---|---|
| 75 | 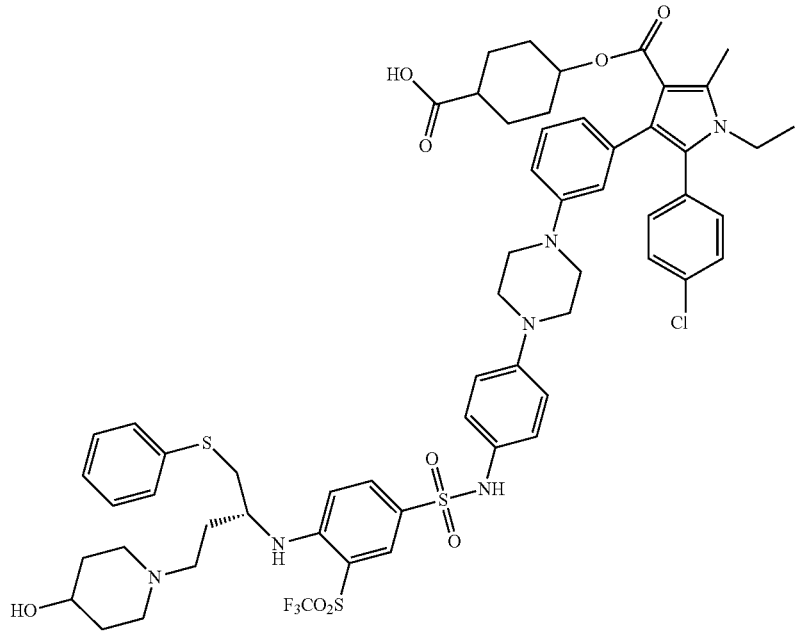 |
| 76 | 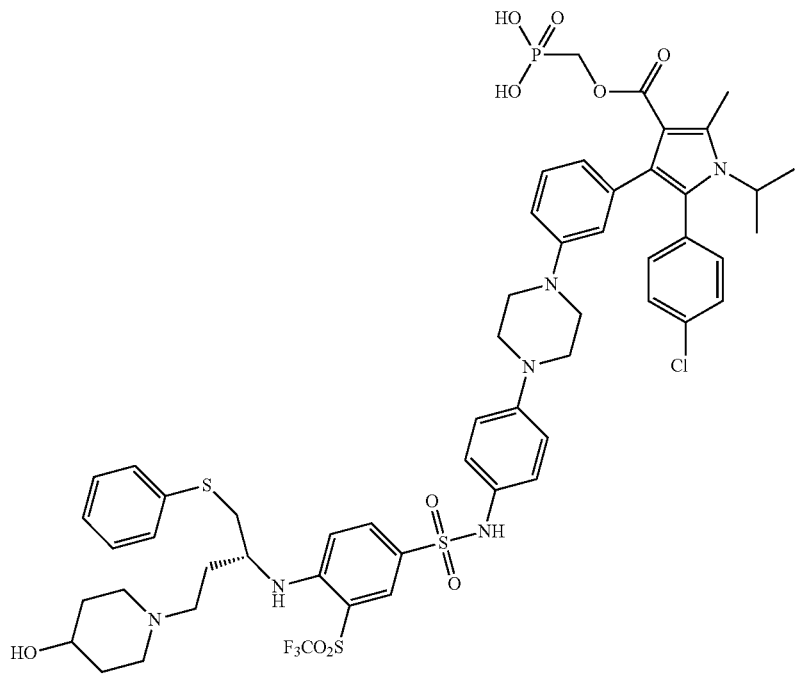 |

TABLE 2-continued
| No. | Structure |
|---|---|
| 77 | 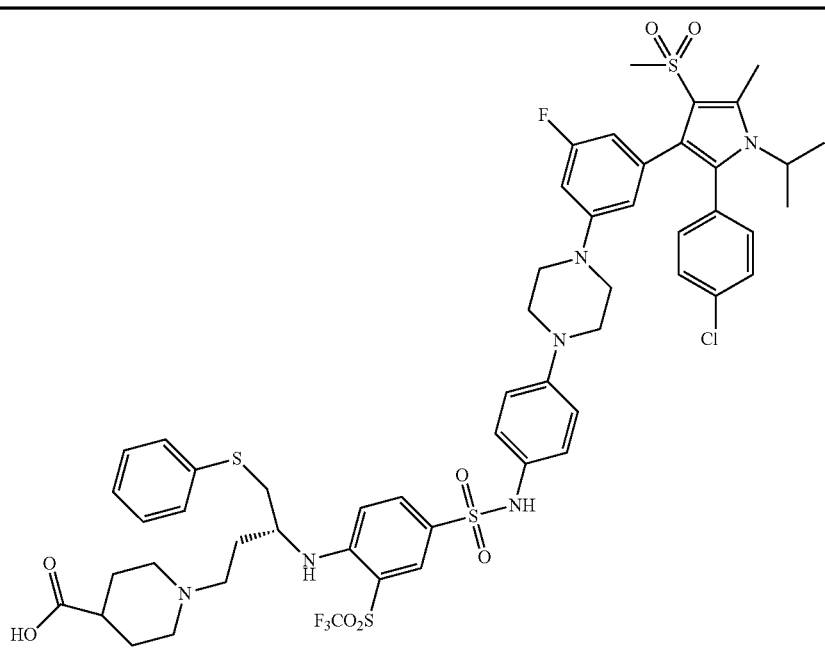 |
| 78 | 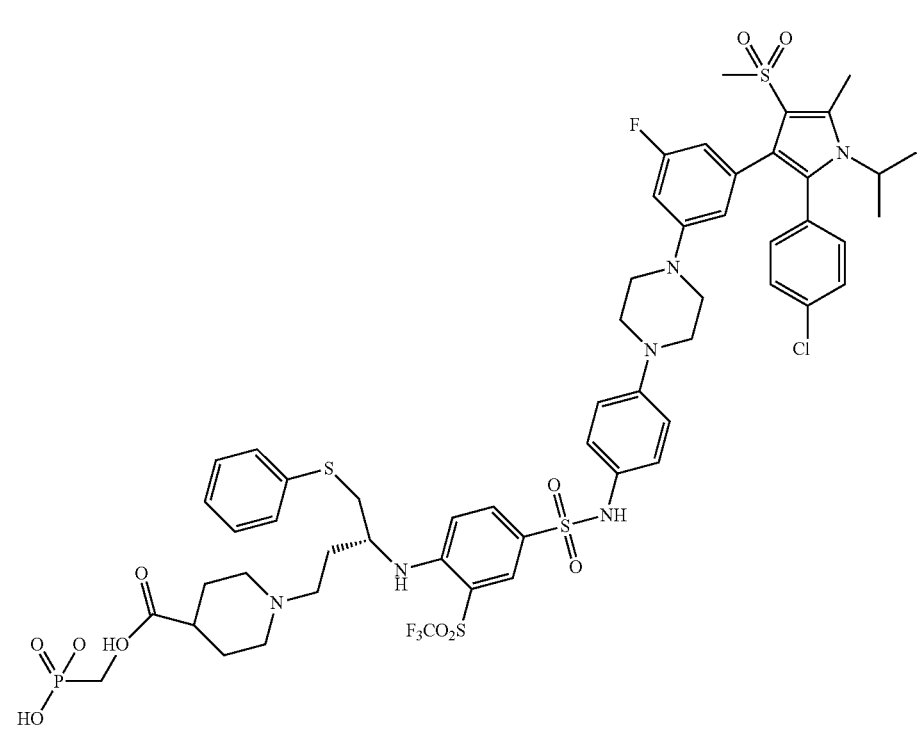 |

TABLE 2-continued
| No. | Structure |
|---|---|
| 79 | 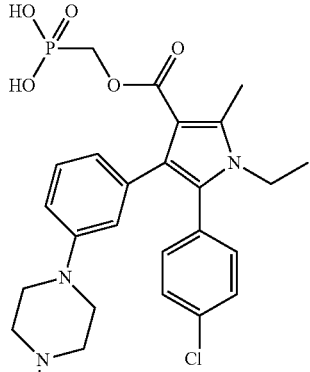 |
| 80 | 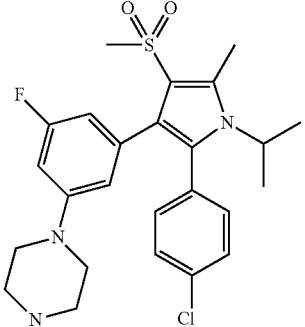 |

120
TABLE 2-continued
| No. | Structure |
|---|---|
| 81 | 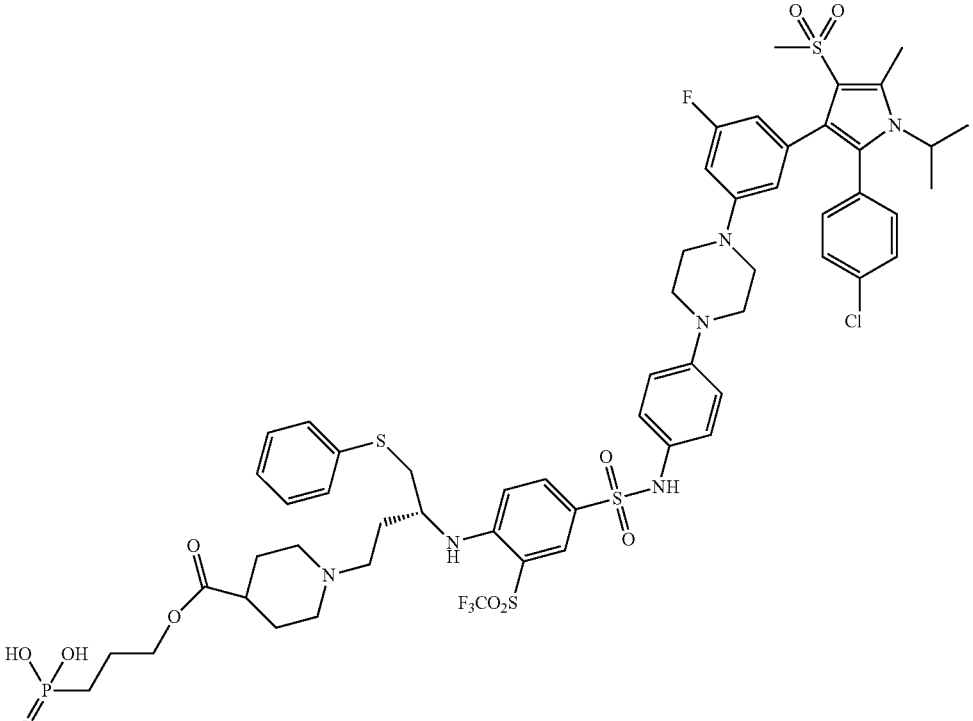 |
| 82 | 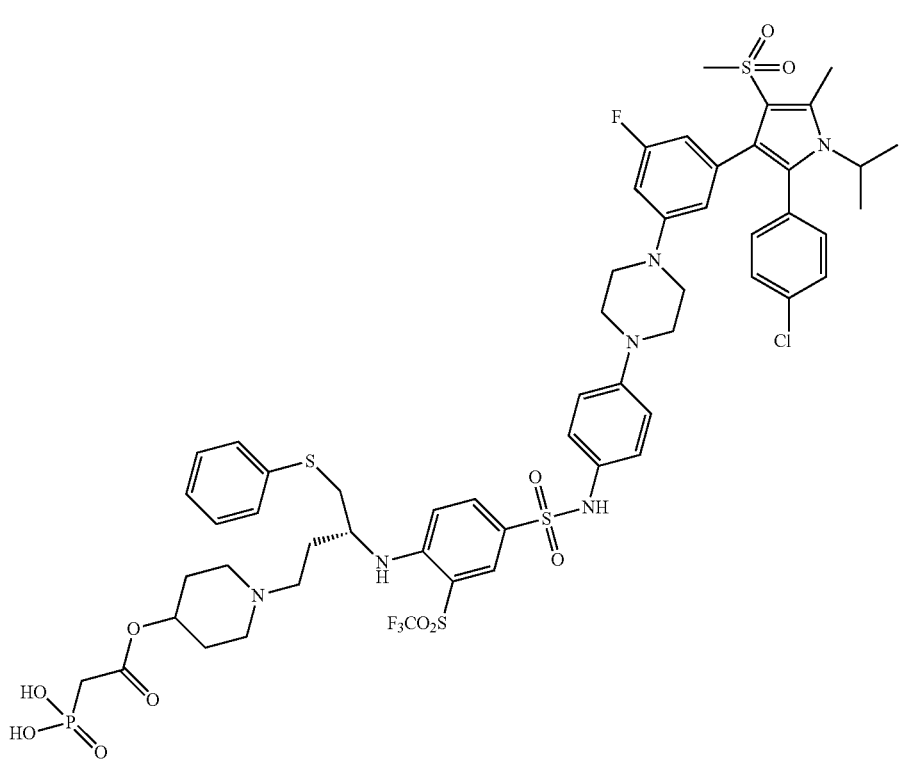 |

TABLE 2-continued
| No. | Structure |
|---|---|
| 83 | 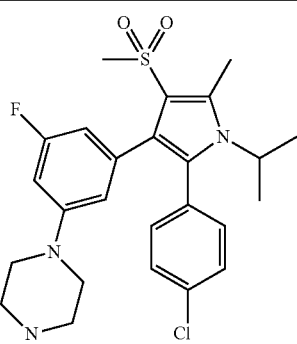 |
| 84 | 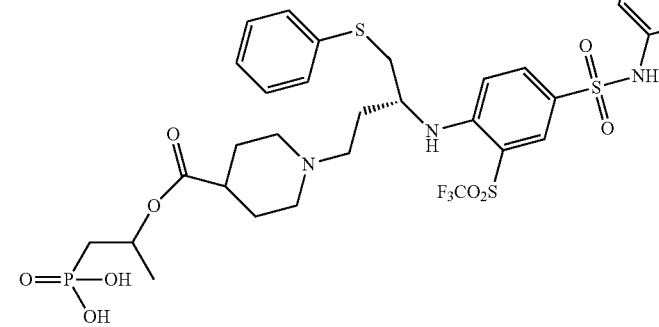 |

TABLE 2-continued
| No. | Structure |
|---|---|
| 85 | 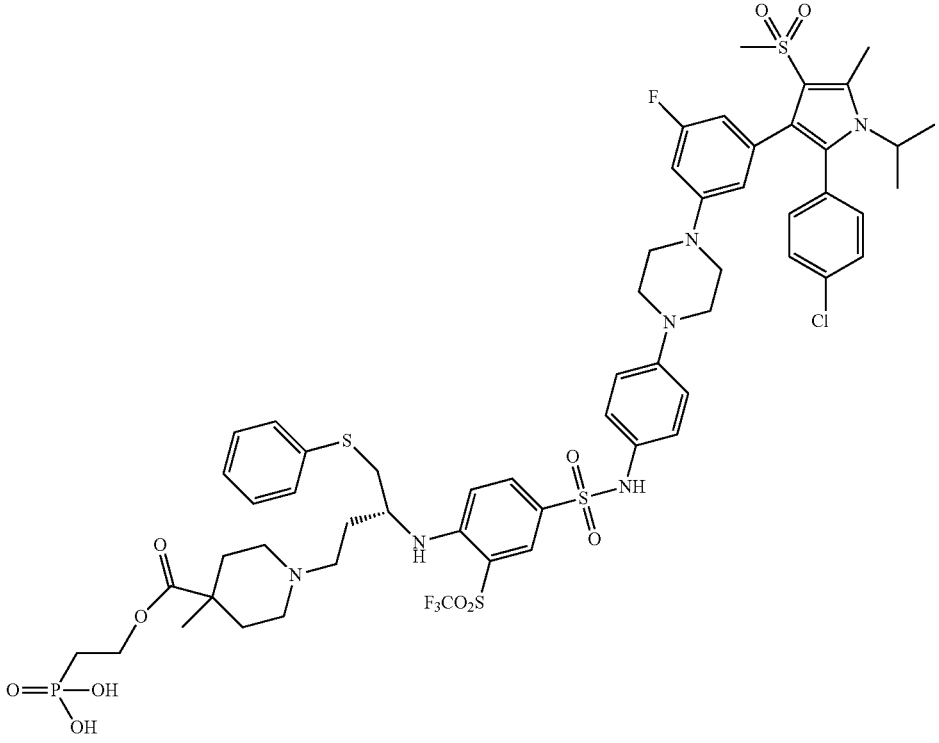 |
| 86 | 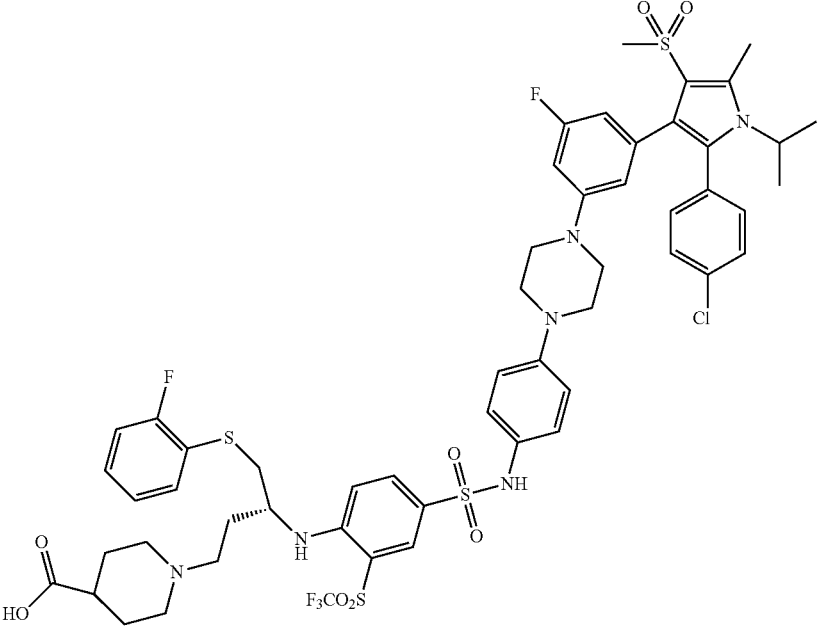 |

TABLE 2-continued
| No. | Structure |
|---|---|
| 87 | 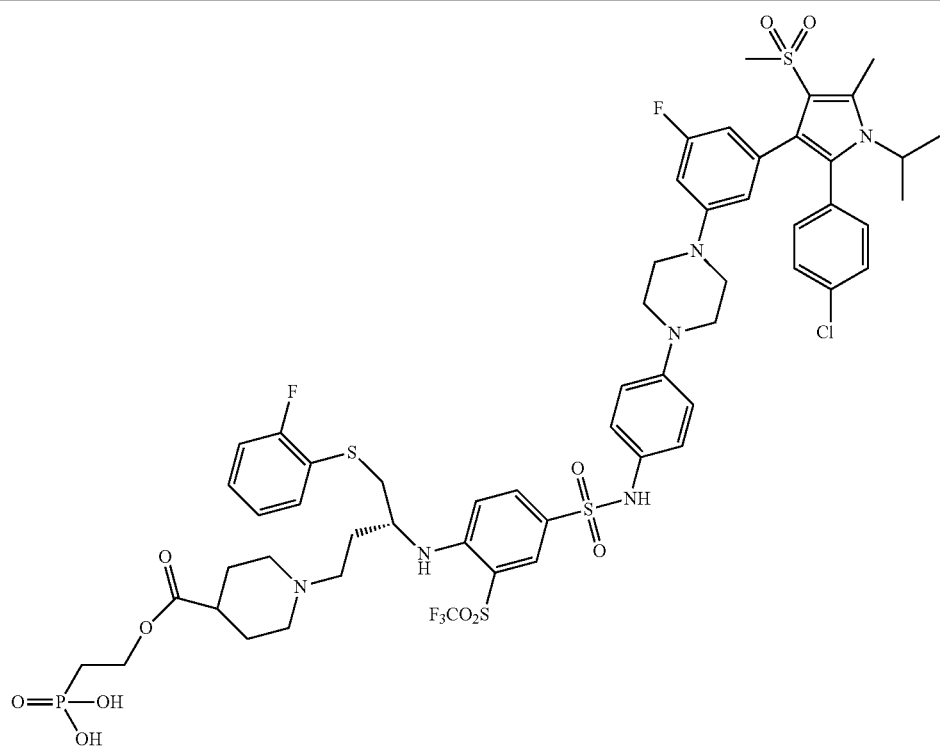 |
| 88 | 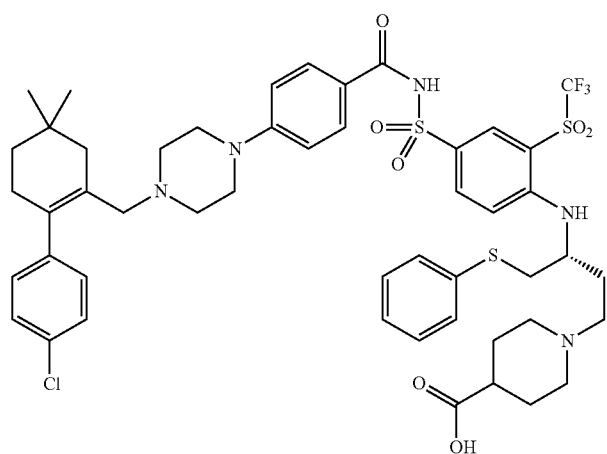 [SMILES: CC1(C)CCC(c2ccc(Cl)cc2)=C(CN2CCN(c3ccc(C(=O)NS(=O)(=O)c4ccc(N[C@H](CCN5CCC(C(=O)O)CC5)CSc5ccccc5)c(S(=O)(=O)C(F)(F)F)c4)cc3)CC2)C1] |

TABLE 2-continued

| No. | Structure |
|-----|-----------|
| 89  | 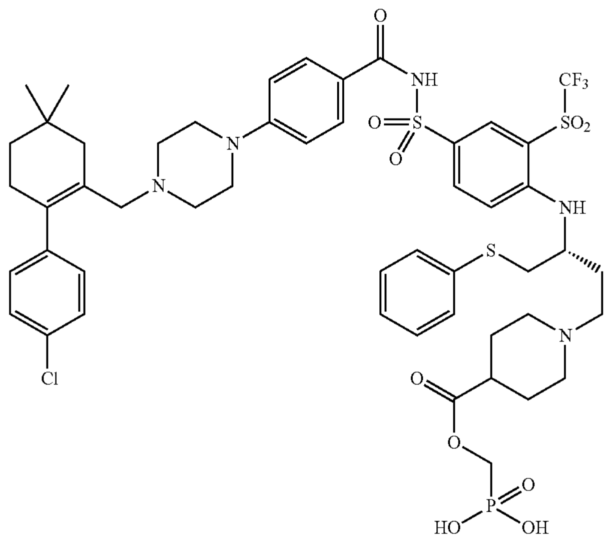 [SMILES: CC1(C)CCC(c2ccc(Cl)cc2)=C(CN2CCN(c3ccc(C(=O)NS(=O)(=O)c4ccc(N[C@H](CCN5CCC(C(=O)OCP(=O)(O)O)CC5)CSc5ccccc5)c(S(=O)(=O)C(F)(F)F)c4)cc3)CC2)C1]          |
| 90  | 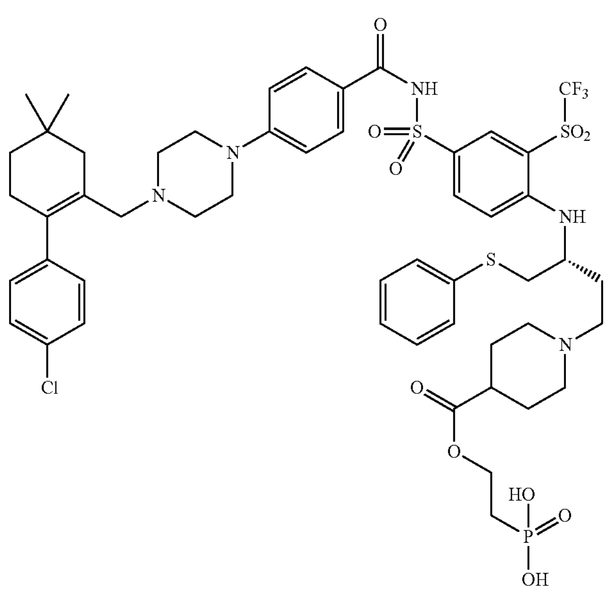 [SMILES: CC1(C)CCC(c2ccc(Cl)cc2)=C(CN2CCN(c3ccc(C(=O)NS(=O)(=O)c4ccc(N[C@H](CCN5CCC(C(=O)OCCP(=O)(O)O)CC5)CSc5ccccc5)c(S(=O)(=O)C(F)(F)F)c4)cc3)CC2)C1]          |

TABLE 2-continued
| No. | Structure |
|---|---|
| 91 | 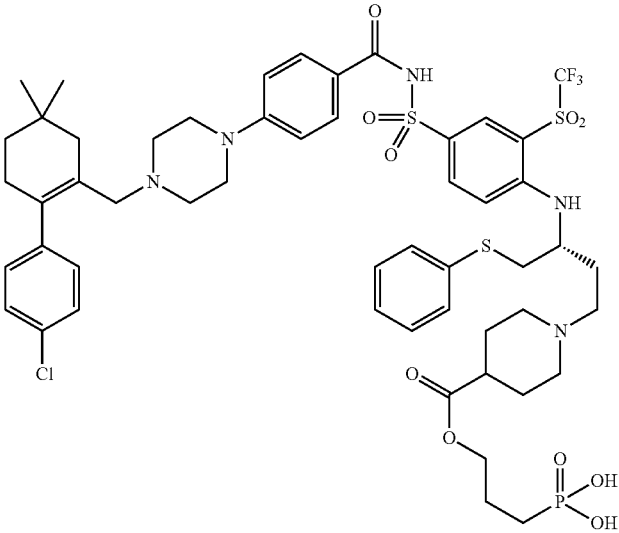 [SMILES: CC1(C)CCC(c2ccc(Cl)cc2)=C(CN2CCN(c3ccc(C(=O)NS(=O)(=O)c4ccc(N[C@H](CCN5CCC(C(=O)OCCCP(=O)(O)O)CC5)CSc5ccccc5)c(S(=O)(=O)C(F)(F)F)c4)cc3)CC2)C1] |
| 92 | 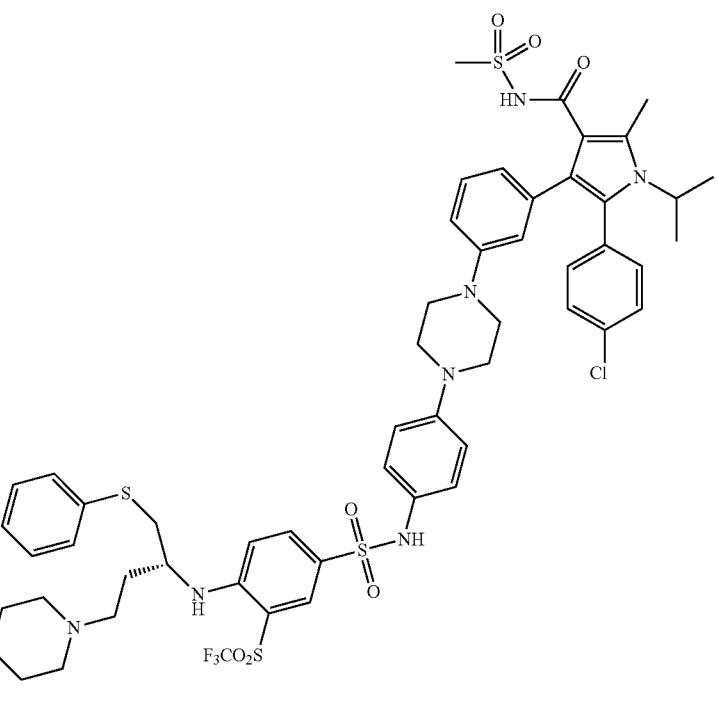 |

| No. | Structure |
|---|---|
| 93 | 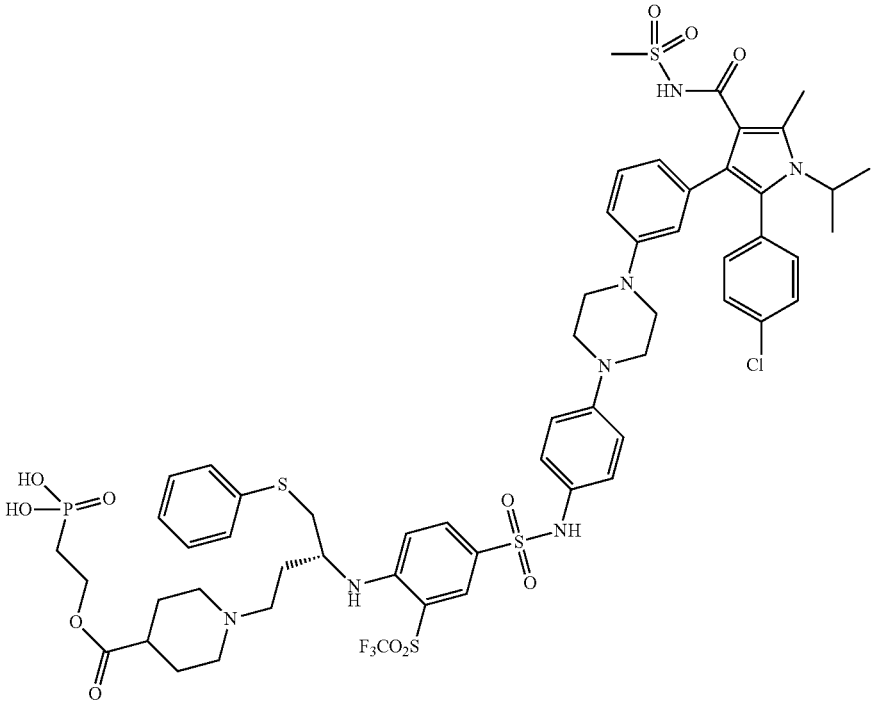 |
| 94 | 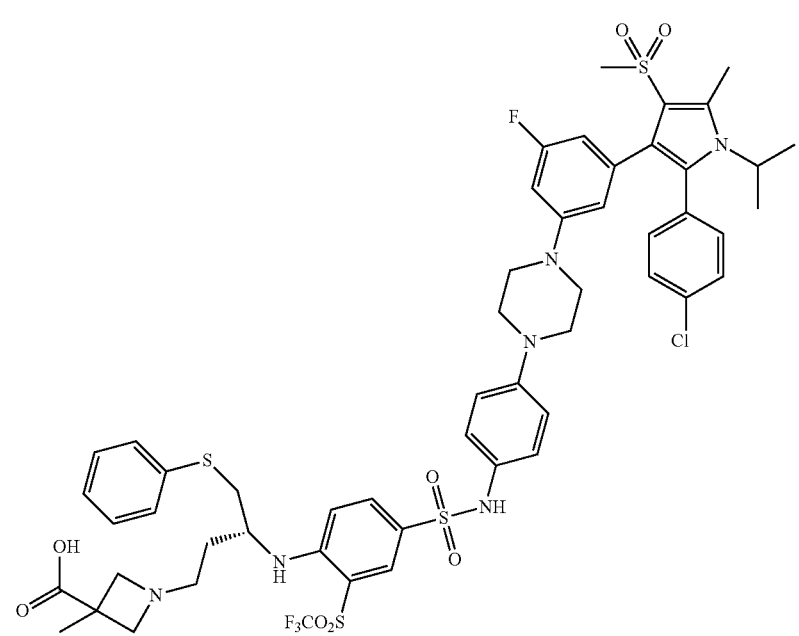 |

TABLE 2-continued
| No. | Structure |
|---|---|
| 95 | 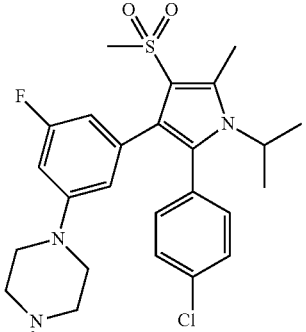 |
| 96 | 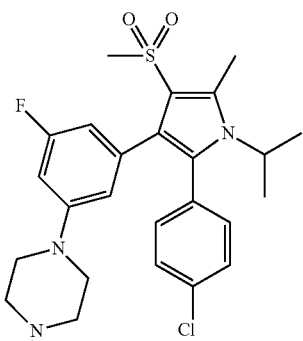 |

TABLE 2-continued
| No. | Structure |
|---|---|
| 97 | 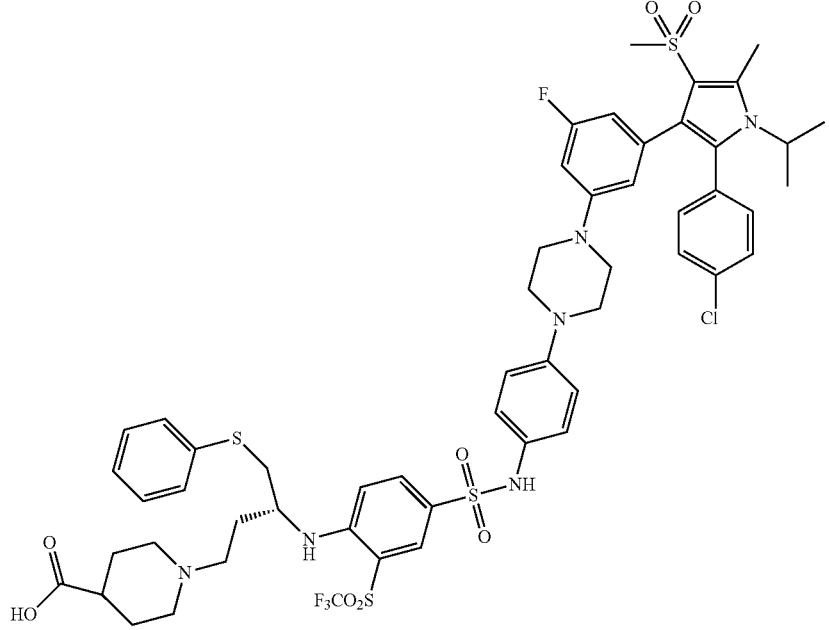 |
| 98 | 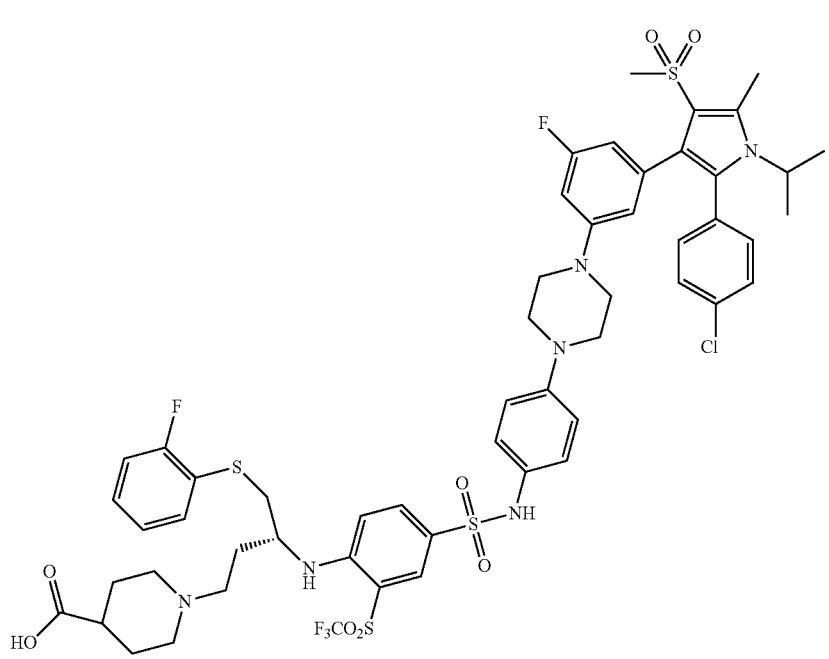 |

TABLE 2-continued
| No. | Structure |
|---|---|
| 99 | 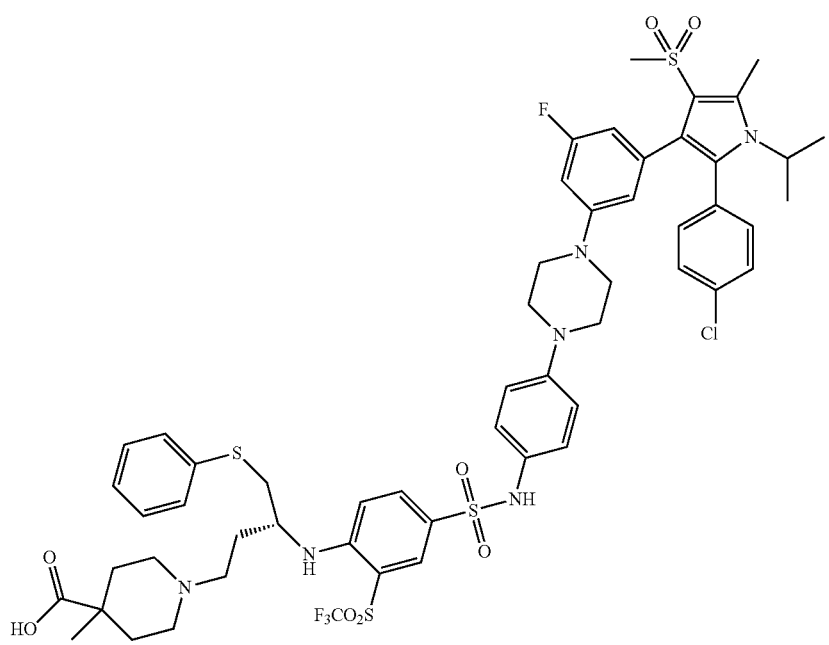 |
| 100 | 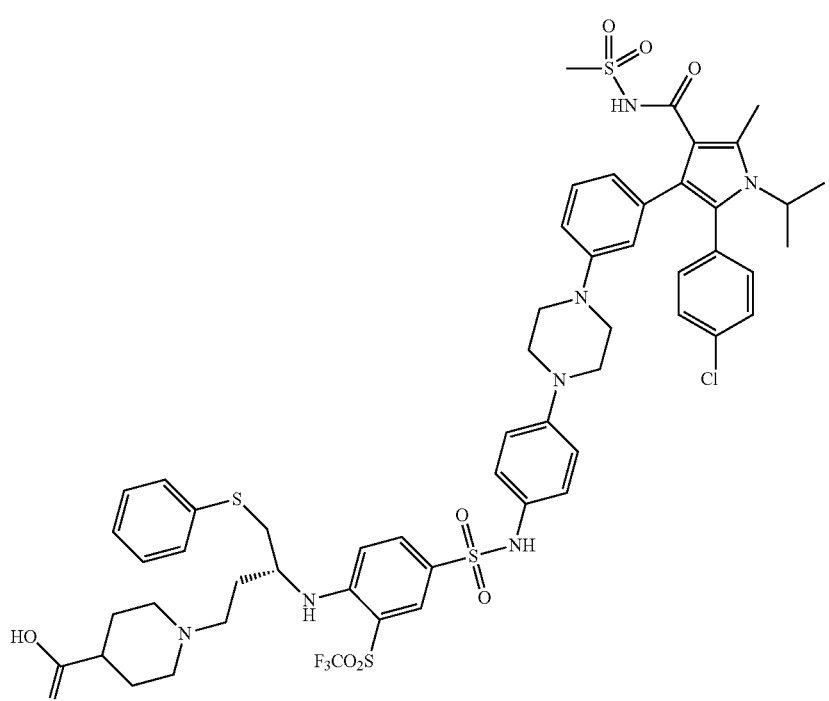 |

TABLE 2-continued

| No. | Structure |
| --- | --- |
| 101 | 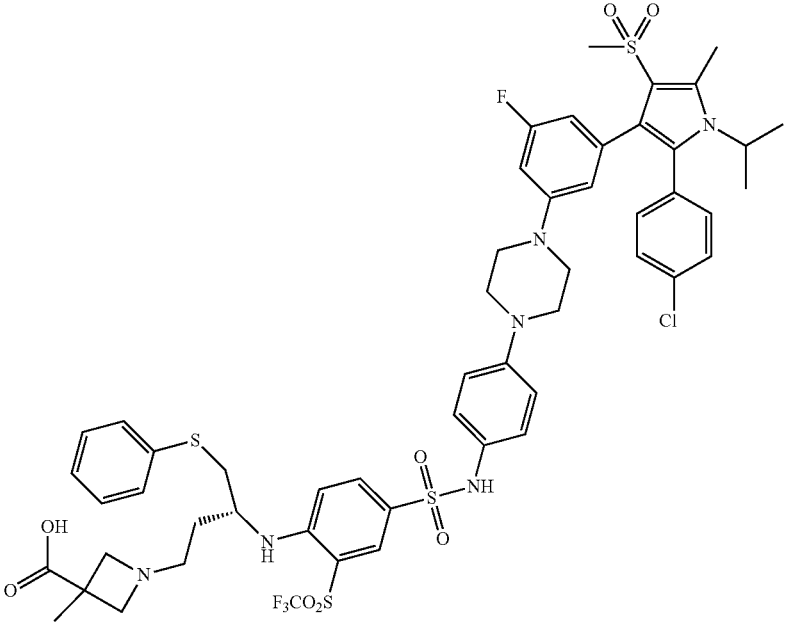 |

In some embodiments, the Bcl-2/Bcl-xL inhibitor of general formulae (I)-(IV) is (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylsulfanyl)butyl)piperidine-4-carbonyloxy)propylphosphonic acid (i.e., compound 81 in the above table, sometimes referred to simply as "compound 81") or a pharmaceutically acceptable salt thereof, represented by the following structural formula:

generation BCL-2 inhibitor in blood circulation through chemical structure modification, but can also be activated by specific enzyme in tissues to effectively kill tumor cells; its platelet toxicity is reduced by 10-30 times, but the activity is about 10 times that of the first generation BCL-2 inhibitor.

The Bcl-2/Bcl-xL inhibitor of the general formulae (I) to (IV) according to the present invention is preferably also (R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl) phenyl)-sulfamoyl)-2-(trifluoromethylsulfo-

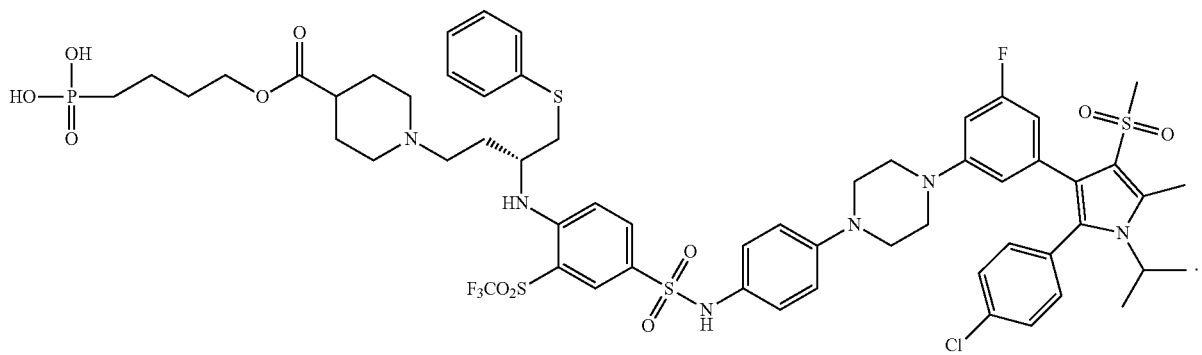

The compound 81 is a second generation new target BCL-2/Bel-xL protein inhibitor, which selectively binds with Bcl-2, Bel-xL and Bcl-w proteins with high affinity, and the IC50 is 1.6 nM, 4.4 nM and 9.3 nM respectively. Compound 81 binds weakly to Mcl-1. The Compound 81 effectively reduces the defect of platelet toxicity of the first nyl)phenylamino)-4-(phenylsulfanyl)butyl)piperidine-4-carboxylic acid (i.e. Compound 97 in the above table, sometimes abbreviated as "Compound 97", Compound 97 being an active metabolite of Compound 81 or a pharmaceutically acceptable salt thereof, represented by the following structural formula:

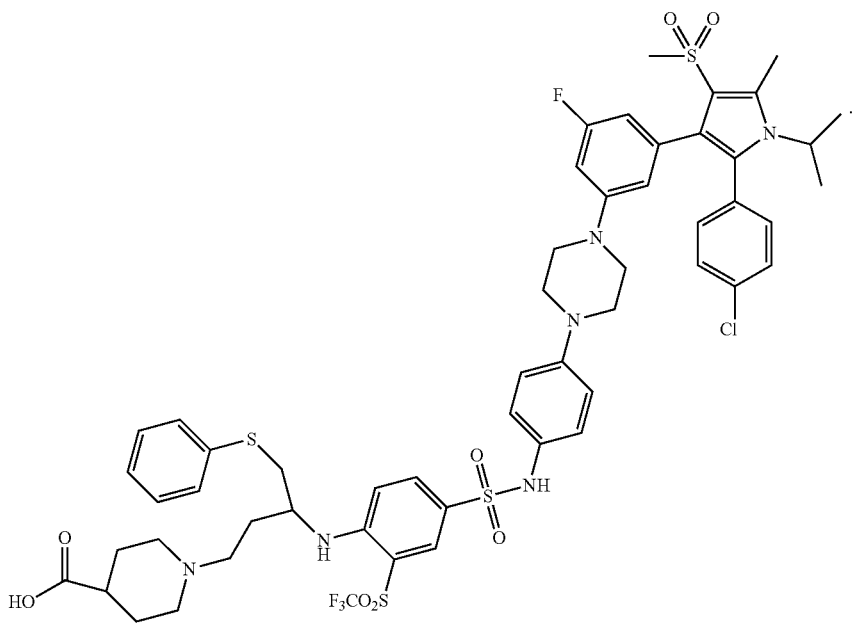

The Bcl-2/Bcl-xL inhibitors of the above general formulae (I)~(V) in the pharmaceutical composition of the present invention can be synthesized and verified for activity thereof according to the method described in WO2014/113413A1.

The compounds of the above formula (I), (II) or (III) have been disclosed in WO2014/113413A1, the entire content of which is incorporated herein by reference. The above general formula (IV) is disclosed in PCT/CN2019/070508, the entire content of the specification of which is incorporated herein by reference.

In some embodiments, the chemotherapeutic agent used in the present invention is selected from one or more of actinomycin, all-trans retinoic acid, azacitidine, azathioprine, bleomycin, bortezomib, carboplatin, capecitabine, cisplatin, chlorambucil, cyclophosphamide, cytarabine, daunorubicin, doxifluridine, doxorubicin, epirubicin, vakrubicin, adriamycin, epothilone, fluorouracil, gemcitabine, hydroxyurea, idarubicin, imatinib, irinotecan, mechlorethamine, mercaptopurine, methotrexate, mitoxantrone, oxaliplatin, paclitaxel, docetaxel, pemetrexed, teniposide, etoposide, thioguanine, topotecan, vemurafenib, vinblastine, vincristine, vindesine, vinorelbine, camptothecin, or hydroxycamptothecine.

In some embodiments, the chemotherapeutic agent is selected from the group consisting of cephalotaxine alkaloids or active derivatives thereof, including but not limited to cephalotaxine, harringtonine, isoharringtonine, homoharringtonine, deoxyharringtonine, homodeoxyharringtonine, drupacine, demethylcephalotaxinone, 11-hydroxycephalotaxine, or epiwilsonine.

In a preferred embodiment, the chemotherapeutic agent is homoharringtonine, or an active derivative thereof.

In some embodiments, the combination product is in the form of a pharmaceutical composition.

In some embodiments, the Bcl-2/Bcl-xL inhibitor and chemotherapeutic agent are each in separate formulations.

In some embodiments, the combination product is in the form of a kit.

In some embodiments, the Bcl-2/Bcl-xL inhibitor and the chemotherapeutic are administered simultaneously or sequentially.

In some embodiments, the Bcl-2/Bcl-xL inhibitor and chemotherapeutic agent are administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the combination product of the present invention comprising the Bcl-2/Bcl-xL inhibitor and a chemotherapeutic agent in the form of a pharmaceutical composition (preferably, each in separate dosage units) may be administered daily, as desired, including but not limited to: 1, 2, 3, 4, 5 or 6 times.

In some embodiments, the combination product of the present invention comprising the Bcl-2/Bcl-xL inhibitor and a chemotherapeutic agent in the form of a pharmaceutical composition (preferably, in dosage unit form) may be administered daily, including but not limited to, as needed: 1, 2, 3, 4, 5 or 6 times.

In some embodiments, the combination product may be administered by: oral, buccal, inhalation spray, sublingual, rectal, transdermal, vaginal mucosal, transmucosal, topical, nasal or intestinal administration; injection, such as intramuscular injection, subcutaneous injection, intramedullary injection, as well as intrathecal, brain direct administration, in situ administration, subcutaneous, intra-abdominal, intravenous injection, intraarticular synovium, intrasternal, intrahepatic, intralesional, intracranial, intraperitoneal, nasal, or intraocular injection or other drug delivery means.

In some embodiments, the Bcl-2/Bcl-xL inhibitor, or a pharmaceutically acceptable salt or solvate thereof, is administered in an amount of about 0.0025 to 1500 mg/day for an adult weighing 60 kg. The amount of said Bcl-2 selective inhibitor is 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 460 mg, 470 mg, 480 mg, 487 mg, 490 mg, 500 mg, 550 mg, 600 mg, 650 mg, 700 mg, 750 mg, 800 mg, 850 mg, 900 mg, 950 mg, 1000 mg, and ranges between the amounts, for example, 1 mg-1000 mg, 30 mg-900 mg, 30 mg-800 mg, 30 mg-900 mg, 30 mg-800 mg, 30 mg-700 mg, 30 mg-600 mg, 30 mg-500 mg, 30 mg-490 mg, 30 mg-487 mg and the like, and the chemotherapeutic agent, or a pharmaceutically acceptable salt or solvate thereof, is administered in an amount of from about 0.005 mg/day to about 5000 mg/day. The amount of the chemotherapeutic agent, such as homoharringtonine, is 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 4.1 mg, 4.2 mg, 4.3 mg, 4.4 mg, 4.5 mg, 4.6 mg, 4.7 mg, 4.8 mg, 4.88 mg, 4.9 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, and ranges between the amounts, for example 0.1-1000 mg, 0.5 mg-1000 mg, 1 mg-1000 mg, 4.88 mg-1000 mg, 4.88 mg-900 mg, 4.88 mg-800 mg, 4.88 mg-700 mg, 4.88 mg-600 mg, 4.88 mg-500 mg, 4.88 mg-400 mg, 4.88 mg-300 mg, 4.88 mg-200 mg, 4.88 mg-100 mg, 4.88 mg-50 mg, 4.88 mg-10 mg, etc.

In some embodiments, the combination product further comprises a pharmaceutically acceptable carrier, diluent or excipient.

In some embodiments, the combination product is in the form of a tablet, capsule, granule, syrup, powder, lozenge, sachet, cachet, elixir, suspension, emulsion, solution, syrup, aerosol, ointment, cream, and injection.

In a second aspect, the present invention relates to the use of a Bcl-2/Bcl-xL inhibitor and a chemotherapeutic agent for the preparation of a medicament for the prevention and/or treatment of a disease selected from cancer.

In some embodiments, the Bcl-2/Bcl-xL inhibitor and the chemotherapeutic agent are those compounds (e.g., compound I-A, or compounds of formulae (I)~(IV)) and chemotherapeutic agents as specifically described in the first aspect of the invention, or pharmaceutically acceptable salts or solvates thereof.

In some embodiments, the medicament is in the form of a pharmaceutical composition.

In some embodiments, the Bcl-2/Bcl-xL inhibitor and the chemotherapeutic agent are each in separate formulations.

In some embodiments, the Bcl-2/Bcl-xL inhibitor and the chemotherapeutic agent are administered simultaneously or sequentially.

In some embodiments, the Bcl-2/Bcl-xL inhibitor and the chemotherapeutic agent are administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the medicament of the present invention containing the Bcl-2/Bcl-xL inhibitor and chemotherapeutic agent in a form of pharmaceutical composition (preferably, each in separate dosage units) may be administered daily, as desired, including but not limited to: 1, 2, 3, 4, 5 or 6 times.

In some embodiments, the medicament of the present invention containing the Bcl-2/Bcl-xL inhibitor and chemotherapeutic agent in a form of pharmaceutical composition (preferably, in dosage unit form) may be administered daily, as desired, including but not limited to: 1, 2, 3, 4, 5 or 6 times.

In some embodiments, the medicament may be administered by: oral, buccal, inhalation spray, sublingual, rectal, transdermal, vaginal mucosal, transmucosal, topical, nasal or intestinal administration; injection, such as intramuscular injection, subcutaneous injection, intramedullary injection, as well as intrathecal, brain direct administration, in situ administration, subcutaneous, intra-abdominal, intravenous injection, intraarticular synovium, intrasternal, intrahepatic, intralesional, intracranial, intraperitoneal, nasal, or intraocular injection or other drug delivery means.

In some embodiments, the daily amounts of the Bcl-2/Bcl-xL inhibitor or pharmaceutically acceptable salt or solvate thereof and the chemotherapeutic agent or pharmaceutically acceptable salt or solvate thereof are as set forth in the first aspect of the invention in the detailed description above.

Further, the cancer described in the present invention includes, but is not limited to, cancers selected from the group consisting of: adrenal cancer, lymphoepithelioma, acinic cell carcinoma, lymphoma, acoustic neuroma, acute lymphocytic leukemia, acral lentigious melanoma, acute myelogeous leukemia, acrospiroma, chronic lymphocytic leukemia, acute eosinophilic leukemia, liver cancer, acute erythroid leukemia, small cell lung cancer, acute lymphoblastic leukemia, non-small cell lung cancer, acute megakaryoblastic leukemia, MALT lymphoma, acute monocytic leukemia, malignant fibrous histiocytoma, acute promyelocytic leukemia, malignant peripheral nerve sheath tumor, adenocarcinoma, malignant triton tumor, adenoid cystic carcinoma, mantle cell lymphoma, adenoma, marginal zone B-cell lymphoma, adenomatoid odontogenic tumor, mast cell leukemia, adenosquamous carcinoma, mediastinal germ cell tumor, adipose tissue neoplasm, medullary carcinoma of the breast, adrenocortical carcinoma, medullary thyroid cancer, adult T-cell leukemia/lymphoma, medulloblastoma, aggressive NK-cell leukemia, melanoma, AIDS-related lymphoma, meningioma, alveolar rhabdomyosarcoma, merkel cell cancer, alveolar soft part sarcoma, mesothelioma, ameloblastic fibroma, metastatic urothelial carcinoma, anaplastic large cell lymphoma, mixed Mullerian tumor, anaplastic thyroid cancer, mucinous tumor, angioimmunoblastic T-cell lymphoma, multiple myeloma, angiomyolipoma, muscle tissue neoplasm, angiosarcoma, mycosis fungoides, astrocytoma, myxoid liposarcoma, atypical teratoid rhabdoid tumor, myxoma, B-cell chronic lymphocytic leukemia, myxosarcoma, B-cell prolymphocytic leukemia, nasopharyngeal carcinoma, B-cell lymphoma, neurinoma, basal cell carcinoma, neuroblastoma, biliary tract cancer, neurofibroma, bladder cancer, neuroma, blastoma, nodular melanoma, bone cancer, ocular cancer, Brenner tumor, oligoastrocytoma, Brown tumor, oligodendroglioma, Burkitt's lymphoma, oncocytoma, breast cancer, optic nerve sheath meningioma, brain cancer, optic nerve tumor, carcinoma, oral cancer, carcinoma in situ, osteosarcoma, carcinosarcoma, ovarian cancer, cartilage tumor, Pancoast tumor, cementoma, papillary thyroid cancer, myeloid sarcoma, paraganglioma, chondroma, pinealoblastoma, chordoma, pineocytoma, choriocarcinoma, pituicytoma, choroid plexus papilloma, pituitary adenoma, clear-cell sarcoma of the kidney, pituitary tumor, craniopharyngioma, plasmacytoma, cutaneous T-cell lymphoma, polyembryoma, cervical cancer, precursor T-lymphoblastic lymphoma, colorectal cancer, primary central nervous system lymphoma, Degos disease, primary effusion lymphoma, desmoplastic small round cell tumor, primary peritoneal cancer, diffuse large B-cell lymphoma, prostate cancer, dysembryoplastic neuroepithelial tumor, pancreatic cancer, dysgerminoma, pharyngeal cancer, embryonal carcinoma, pseudomyxoma periotonei, endocrine gland neoplasm, renal cell carcinoma, endodermal sinus tumor, renal medullary carcinoma, enteropathy-associated T-cell lymphoma, retinoblastoma, esophageal cancer, rhabdomyoma, fetus in fetu, rhabdomyosarcoma, fibroma, Richter's transformation, fibrosarcoma, rectal cancer, follicular lymphoma, sarcoma, follicular thyroid cancer, Schwannomatosis, ganglioneuroma, seminoma, gastrointestinal cancer, Sertoli cell tumor, germ cell tumor, sex cord-gonadal stromal tumor, gestational choriocarcinoma, signet ring cell carcinoma, giant cell fibroblastoma, skin cancer, giant cell tumor of the bone, small blue round cell tumors, glial tumor, small cell carcinoma, glioblastoma multiforme, soft tissue sarcoma, glioma, somatostatinoma, gliomatosis cerebri, soot wart, glucagonoma, spinal tumor, gonadoblastoma, splenic marginal zone lymphoma, granulosa cell tumor, squamous cell carcinoma, gynandroblastoma, synovial sarcoma, gallbladder cancer, Sezary's disease, gastric cancer, small intestine cancer, hairy cell leukemia, squamous carcinoma, hemangioblastoma, stomach cancer, head and neck cancer, T-cell lymphoma, hemangiopericytoma, testicular cancer, hematological malignancy, thecoma, hepatoblastoma, thyroid cancer, hepatosplenic T-cell lymphoma, transitional cell carcinoma, Hodgkin's lymphoma, throat cancer, non-Hodgkin's lymphoma, urachal cancer, invasive lobular carcinoma, urogenital cancer, intestinal cancer, urothelial carcinoma, kidney cancer, uveal melanoma, laryngeal cancer, uterine cancer, lentigo maligna, verrucous carcinoma, lethal midline carcinoma, visual pathway glioma, leukemia, vulvar cancer, leydig cell tumor, vaginal cancer, liposarcoma, Waldenstrom's macroglobulinemia, lung cancer, Warthin's tumor, lymphangioma, Wilms' tumor, and lymphangiosarcoma.

Preferably, the cancer is selected from the group consisting of bladder cancer, breast cancer, cervical cancer, colon cancer (including colorectal cancer), esophageal cancer, head and neck cancer, liver cancer, lung cancer (small cell lung cancer and non-small cell lung cancer), melanoma, myeloma, neuroblastoma, ovarian cancer, pancreatic cancer, prostate cancer, kidney cancer, sarcoma (including osteosarcoma), skin cancer (including squamous cell carcinoma), stomach cancer, testicular cancer, thyroid cancer, uterine cancer, mesothelioma, cholangiocarcinoma, leiomyosarcoma, liposarcoma, melanoma, nasopharyngeal cancer, neuroendocrine cancer, ovarian cancer, renal cancer, salivary gland cancer, spindle cell carcinoma-induced metastases, non-hodgkin's lymphoma, Hodgkin's lymphoma, and hematological malignancies such as Acute Myeloid Leukemia (AML), Acute Lymphocytic Leukemia (ALL), diffuse large B-cell lymphoma (DLBCL), Follicular Lymphoma (FL), Chronic Lymphocytic Leukemia (CLL), Chronic Myelogenous Leukemia (CML), Mantle Cell Lymphoma (MCL).

Preferably, the cancer is selected from hematological malignancies, including but not limited to Acute Myelogenous Leukemia (AML), Acute Lymphoblastic Leukemia (ALL), Chronic Lymphocytic Leukemia (CLL), Chronic Myeloid Leukemia (CML), acute eosinophilic cell leukemia, acute erythrocytic leukemia, acute megakaryocytic leukemia, acute monocytic leukemia, acute promyelocytic leukemia, adult T-cell leukemia/lymphoma, aggressive NK-cell leukemia, mast cell leukemia, hairy cell leukemia, mixed lineage leukemia, non-Hodgkin lymphoma, Hodgkin lymphoma, Mantle Cell Lymphoma (MCL), diffuse large B-cell lymphoma (DLBCL), Follicular Lymphoma (FL), B-cell lymphoma, mucosa-associated lymphoid tissue (MALT) lymphoma, anaplastic large cell lymphoma, T-cell lymphoma, Burkitt's lymphoma, T lymphoblastic lymphoma, primary central nervous system lymphoma, primary effusion lymphoma, multiple myeloma, macroglobulinemia, myelodysplastic syndrome (MDS), primary thrombocytosis, polycythemia vera, primary myelofibrosis.

Preferably, the cancer is of the above-mentioned classes that are resistant to chemotherapy.

Most preferably, the cancer is Acute Myelogenous Leukemia (AML) or myelodysplastic syndrome (MDS), especially chemotherapy-resistant Acute Myelogenous Leukemia (AML) or myelodysplastic syndrome (MDS).

In the third aspect, the present invention relates to a combination product comprising a Bcl-2/Bcl-xL inhibitor and a chemotherapeutic agent for use in the prevention and/or treatment of cancer. Further, the cancer includes, but is not limited to, those described in the above detailed description of the invention in the second aspect of the invention.

In some embodiments, the Bcl-2/Bcl-xL inhibitor is a compound as those specifically described in the first aspect of the invention (e.g., compound I-A, or compounds of formulae (I)-(IV)), or a pharmaceutically acceptable salt or solvate thereof, and the chemotherapeutic agent is as those specifically described in the first aspect of the invention, or a pharmaceutically acceptable salt or solvate thereof.

In some embodiments, the combination product is in the form of a pharmaceutical composition.

In some embodiments, the Bcl-2/Bcl-xL inhibitor and the chemotherapeutic agent are each in separate formulations.

In some embodiments, the combination product is in the form of a kit.

In some embodiments, the Bcl-2/Bcl-xL inhibitor and the chemotherapeutic agent are administered simultaneously or sequentially.

In some embodiments, the Bcl-2/Bcl-xL inhibitor and the chemotherapeutic agent are administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the combination product of the invention comprising the Bcl-2/Bcl-xL inhibitor and the chemotherapeutic agent, e.g., a kit, in the form of a pharmaceutical composition (preferably, each in separate dosage units) can be administered daily, as desired, including but not limited to: 1, 2, 3, 4, 5 or 6 times.

In some embodiments, the combination product of the present invention comprising the Bcl-2/Bcl-xL inhibitor and the chemotherapeutic agent in the form of a pharmaceutical composition (preferably, in dosage unit form) may be administered daily, including but not limited to, as needed: 1, 2, 3, 4, 5 or 6 times.

In some embodiments, the combination product may be administered by: oral, buccal, inhalation spray, sublingual, rectal, transdermal, vaginal mucosal, transmucosal, topical, nasal or intestinal administration; injection, such as intramuscular injection, subcutaneous injection, intramedullary injection, as well as intrathecal, brain direct administration, in situ administration, subcutaneous, intra-abdominal, intravenous injection, intraarticular synovial membrane, intrasternal, intrahepatic, intralesional, intracranial, intraperitoneal, nasal, or intraocular injection or other drug delivery means.

In some embodiments, the daily dosage amounts of the Bcl-2/Bcl-xL inhibitor or pharmaceutically acceptable salt or solvate thereof and the chemotherapeutic agent or pharmaceutically acceptable salt or solvate thereof are as set forth in the first aspect of the invention in the above detailed description of the invention.

In the fourth aspect, the present invention relates to a method of preventing and/or treating cancer comprising administering to a subject in need thereof a prophylactically and/or therapeutically effective amount of a Bcl-2/Bcl-xL inhibitor and a chemotherapeutic agent. Further, the cancer includes, but is not limited to, those as described in the second aspect of the invention in the above detailed description of the invention.

In some embodiments, the Bcl-2/Bcl-xL inhibitor is a compound as those specifically described in the first aspect of the invention (e.g., compound I-A, or compounds of formulae (I)-(IV)), or a pharmaceutically acceptable salt or solvate thereof, and the chemotherapeutic agent is as those specifically described in the first aspect of the invention, or a pharmaceutically acceptable salt or solvate thereof.

In some embodiments, the Bcl-2/Bcl-xL inhibitor and the chemotherapeutic agent are in a pharmaceutical composition.

In some embodiments, the Bcl-2/Bcl-xL inhibitor and the chemotherapeutic agent are each in separate formulations, e.g., in a kit.

In some embodiments, the Bcl-2/Bcl-xL inhibitor and the chemotherapeutic agent are administered simultaneously or sequentially.

In some embodiments, the Bcl-2/Bcl-xL inhibitor and the chemotherapeutic agent are administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2/Bcl-xL inhibitor and the chemotherapeutic agent in a pharmaceutical composition (preferably, each in separate dosage units) can be administered daily, as desired, including but not limited to: 1, 2, 3, 4, 5 or 6 times.

In some embodiments, the Bcl-2/Bcl-xL inhibitor and the chemotherapeutic agent in a pharmaceutical composition (preferably, in dosage unit form) may be administered as needed daily, including but not limited to: 1, 2, 3, 4, 5 or 6 times.

In some embodiments, the Bcl-2/Bcl-xL inhibitor and the chemotherapeutic agent may be administered by: oral, buccal, inhalation spray, sublingual, rectal, transdermal, vaginal mucosal, transmucosal, topical, nasal or intestinal administration; injection, such as intramuscular injection, subcutaneous injection, intramedullary injection, as well as intrathecal, brain direct administration, in situ administration, subcutaneous, intra-abdominal, intravenous injection, intraarticular synovial membrane, intrasternal, intrahepatic, intralesional, intracranial, intraperitoneal, nasal, or intraocular injection or other drug delivery means.

In some embodiments, the Bcl-2/Bcl-xL inhibitor is administered daily at 0.017 mg/kg, 0.083 mg/kg, 0.17 mg/kg, 0.33 mg/kg, 0.5 mg/kg (30 mg per day for a 60 kg subject), 0.67 mg/kg, 0.83 mg/kg, 1 mg/kg, 1.16 mg/kg, 1.33 mg/kg, 1.5 mg/kg, 1.67 mg/kg, 2.5 mg/kg, 3.33 mg/kg, 4.17 mg/kg, 5 mg/kg, 5.83 mg/kg, 6.67 mg/kg, 7.5 mg/kg, 7.67 mg/kg, 7.83 mg/kg, 8 mg/kg, 8.12 mg/kg (487 mg per day for a 60 kg subject), 8.16 mg/kg, 8.33 mg/kg, 9.17 mg/kg, 10 mg/kg, 10.83 mg/kg, 11.66 mg/kg, 12.5 mg/kg, 13.33 mg/kg, 14.17 mg/kg, 15 mg/kg, 15.83 mg/kg, 16.67 mg/kg, and ranges therebetween, e.g., 0.017 mg-16.67 mg/kg, 0.083 mg-16.67 mg/kg, 0.17 mg-16.67 mg/kg, 0.33 mg-16.67 mg/kg, 0.5 mg-15 mg/kg, 0.5 mg-13.33 mg/kg, 0.5 mg-11.67 mg/kg, 0.5 mg-10 mg/kg, 0.5 mg-8.33 mg/kg, 0.5 mg-8.16 mg/kg, 0.5 mg-8.12 mg/kg, etc., and the daily administration of the chemotherapeutic agent, such as homoharringtonine, is 0.001 mg/kg, 0.005 mg/kg, 0.01 mg/kg, 0.02 mg/kg, 0.03 mg/kg, 0.04 mg/kg, 0.05 mg/kg, 0.04 mg/kg, 0.06 mg/kg, 0.07 mg/kg, 0.08 mg/kg, 0.09 mg/kg, 0.1 mg/kg, 0.5 mg/kg, 1 mg/kg, 2 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 300 mg/kg, 350 mg/kg, 400 mg/kg, 450 mg/kg, 500 mg, and ranges therebetween, for example, 0.001 mg-500 mg/kg, 0.005 mg-500 mg/kg, 0.01 mg-500 mg/kg, 0.05 mg-500 mg/kg, 0.08 mg-500 mg/kg, 0.08 mg-400 mg/kg, 0.08 mg-300 mg/kg, 0.08 mg-200 mg/kg, 0.08 mg-100 mg/kg, 0.08 mg-50 mg/kg, 0.08 mg-10 mg/kg, 0.08 mg-1 mg/kg, 0.08 mg-0.5 mg/kg, 0.08 mg-0.1 mg/kg, etc.

Most surprisingly, the present inventors have experimentally found that the combined administration of a Bcl-2/Bcl-xL inhibitor and a chemotherapeutic agent as defined herein not only results in a beneficial, especially synergistic, therapeutic effect, but also results in additional benefits due to the combined treatment, such as an unexpectedly prolonged efficacy, a broader range of treated diseases, and unexpectedly beneficial effects on AML/MDS related diseases and conditions, such as a significantly enhanced efficacy, thereby extending the dosing cycle and providing the patient with a longer survival benefit.

A further advantage is that lower doses of the respective drugs to be combined according to the invention can be used, for example, the required dose is not only smaller but also less frequently; or may be used to reduce the incidence of side effects, which are consistent to the desires and requirements of the patients to be treated. In particular, the combination product of the invention may reduce to some extent the hematological toxicity associated with said Bcl-2/Bcl-xL inhibitors and the cardiovascular toxicity associated with cephalotaxin alkaloids.

The combination of a Bcl-2/Bcl-xL inhibitor and a chemotherapeutic agent, particularly Compound 6 and homoharringtonine, can be demonstrated to be more effective in preventing or treating cancer, such as AML/MDS, by art-established test models, particularly those described herein.

The person skilled in the relevant art is fully enabled to select suitable animal test models to prove the hereinbefore and hereinafter indicated therapeutic indications and beneficial effects. Pharmacological activity may be demonstrated, for example, by in vivo assay methods in mice or clinical studies as described hereinafter.

General or preferred definitions of a given feature in various enumerated embodiments of the present invention may be combined with general or preferred definitions of other features to yield yet further embodiments of the present invention, as if such combinations were specifically and individually set forth herein, unless the context clearly indicates otherwise.

Unless a formula is clearly wrong, when the chemical name of any compound of the present invention is inconsistent with a given formula, the formula prevails.

In this specification, several prior publications are referenced. These publications, while not considered to be relevant to the patentability of the invention, are incorporated herein by reference in their entirety. The reference in this specification to any prior publication (or information derived from it), is not, and should not be taken as, an acknowledgment or admission or any form of suggestion that the corresponding prior publication (or information derived from it) forms part of the common general knowledge in the field of technology to which this specification relates.

SPECIFIC EMBODIMENTS

The present invention is further illustrated by the following specific examples and comparative examples, which are, however, to be construed as merely illustrative in more detail and not limitative of the remainder of the disclosure in any way whatsoever.

The experimental procedures, for which specific conditions are not noted in the following examples, are generally carried out according to the conventional conditions for such reactions, or according to the conditions recommended by the manufacturer.

The experimental materials and reagents used in the following examples are commercially available, prepared according to prior art methods or prepared according to methods similar to those disclosed in the present application, unless otherwise specified.

Synthesis Examples: Preparation of Exemplary Bcl-2 Selective Inhibitor Compounds (Compounds 3, 6 and 13)

Synthesis of Compound 3: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide

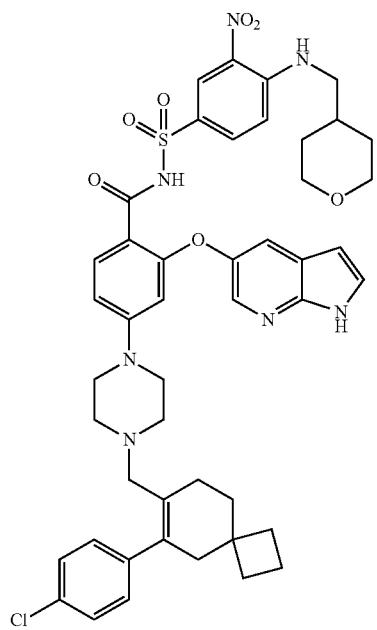 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1]

A mixture of 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoic acid (1.75 g, 3 mmol), 3-nitro-4-(((tetrahydro-2H-pyran-4-yl)methyl)amino)benzenesulfonamide (1.43 g, 4.5 mmol), EDCI (1.15 g, 6 mmol) and 4-(N,N-dimethylamino)pyridine (550 mg, 4.5 mmol) and dichloromethane (40 ml) was reacted at room temperature overnight before water was added. The aqueous layer was extracted with dichloromethane. The combined organic layers were washed with brine, concentrated and purified by silica gel column to give 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide (1.7 g, 64.4%) as a yellow solid.

1H NMR (400 MHz, methanol-d4) δ 8.70 (d, J=2.3 Hz, 1H), 8.01 (d, J=2.7 Hz, 1H), 7.87 (d, J=9.2, 2.3 Hz, 1H), 7.66 (d, J=8.9 Hz, 1H), 7.55 (d, J=2.7 Hz, 1H), 7.47 (d, J=3.4 Hz, 1H), 7.38 (d, J=8.4 Hz, 2H), 7.10 (d, J=8.4 Hz, 2H), 6.97 (d, J=9.2 Hz, 1H), 6.77 (dd, J=8.9, 2.4 Hz, 1H), 6.44 (d, J=3.4 Hz, 1H), 6.34 (d, J=2.4 Hz, 1H), 4.02-3.94 (m, 3H), 3.66 (s, 3H), 3.49-3.38 (m, 2H), 3.41-3.25 (m, 7H), 2.42 (s, 3H), 2.26 (s, 3H), 2.00-1.67 (m, 4H), 1.45-1.38 (m, 2H).

Synthesis of Compound 13: (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide

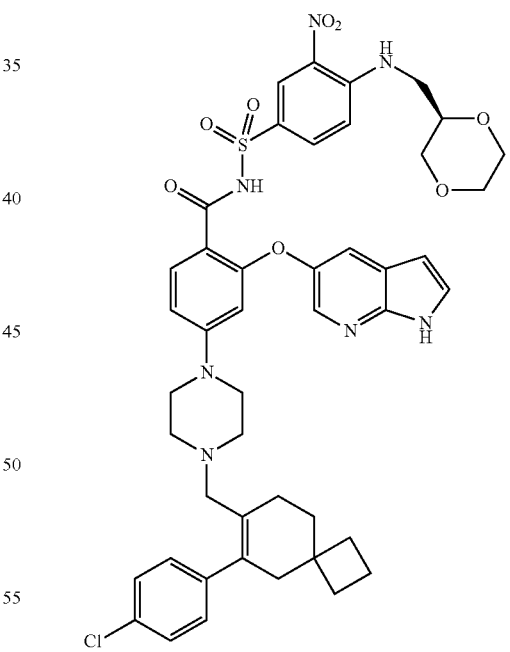

The title compound was prepared using procedures analogous to those described for the synthesis of Compound 3.

1H NMR (400 MHz, methanol-d4) δ 8.66 (d, J=2.4 Hz, 1H), 7.99 (d, J=2.4 Hz, 1H), 7.84 (dd, J=9.2, 2.4 Hz, 1H), 7.64 (d, J=8.9 Hz, 1H), 7.51 (d, J=2.4 Hz, 2H), 7.45 (d, J=3.3 Hz, 1H), 7.37 (d, J=8.4 Hz, 2H), 7.10 (d, J=8.4 Hz, 2H), 6.94 (d, J=9.2 Hz, 1H), 6.76 (dd, J=8.9, 2.3 Hz, 1H), 6.40 (d, J=3.3 Hz, 1H), 6.36 (d, J=2.3 Hz, 1H), 3.87 (dd, J=11.8, 4.2 Hz, 3H), 3.83-3.70 (m, 3H), 3.67 (s, 2H), 3.62 (dd, J=11.7, 2.9 Hz, 1H), 3.51-3.41 (m, 2H), 3.40-3.35 (m, 1H), 3.29 (dq, J=3.2, 1.6 Hz, 1H), 2.41 (s, 2H), 2.26 (s, 2H), 2.00-1.77 (m, 6H)

Synthesis of Compound 6: (S)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide

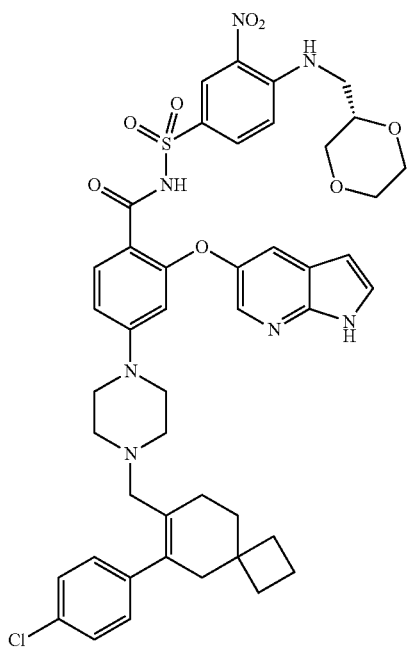 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

The title compound was prepared using procedures analogous to those described for the synthesis of Compound 13. MS: $C_{45}H_{48}ClN_7O_8S$, found 882.3047, calculated 882.3046.

1HNMR (400 MHz, d-DMSO): δ ppm: 11.70 (1H, s); 11.35 (1H, br); 8.59 (2H, m); 8.05 (1H, d, J=2.6); 7.84 (1H, dd, J1=9.2; J2=2.3); 7.51 (3H, m); 7.33 (2H, d, J=8.4); 7.10 (1H, d, J=9.2); 7.04 (2H, d, J=8.4); 6.66 (1H, dd, J1=8.8, J2=1.2); 6.39 (1H, dd, J1=3.6, J2=2.0); 6.19 (1H, d, J=1.2); 3.77-3.82 (3H, m); 3.64 (1H, t, J=11.2); 3.62 (1H, dd, J1=10.8, J2=2.4); 3.30-3.52 (4H, m); 3.06 (4H, m); 2.72 (2H, m); 2.13-2.23 (8H, m); 1.67~1.86 (6H, m); 1.58 (2H, m).

Activity Examples

List of Abbreviations

Abbreviations Full name in English
AML Acute myeloid leukemia
HHT Homoharringtonine
BAK BCL-2 associated X protein
BCL-2 B-cell Lymphoma 2
CI Combination index
CTG CellTiter-Glo
DMSO Dimethyl sulfoxide
FCM Flow cytometry
h Hours
$IC_{50}$ Half maximum inhibitory concentration
MCL-1 Myeloid Cell Leukemia 1
MSD MSD electrochemi luminescence detection
PARP-1 Poly ADP-ribose polymerase-1
PBS Phosphonate buffered saline
PI Propidium iodide
SEM Standard error of mean General Materials and Methods 1. Cell Lines AML cell lines are available from commercial sources, such as Nanjing COBIOER Biotechnology Ltd (OCI-AML-3 and MV-4-11), Japanese Cancer Research Resource Bank (JCRB: SKM-1). The cells were cultured in the corresponding medium all at 37° C. in a 5% $CO_2$ incubator. The culture conditions for the AML cell line used in this study are shown in table 1.

TABLE 1

| Culture conditions of AML/MDS cell lines | |
|---|---|
| Cell lines | Culture conditions |
| MV-4-11 | 90% IMDM basal medium; 10% fetal bovine serum; 1% penicillin-streptomycin |
| OCI-AML-3 | 90% RPMI 1640 basal medium; 10% fetal bovine serum; 1% penicillin-streptomycin |
| SKM-1 | 90% RPMI 1640 basal medium; 10% fetal bovine serum; 1% penicillin-streptomycin |

In the antiproliferative tests, cells were plated in 96-well plates (Corning, Cat. 3903) at 10000 cells/well/cell line. In the apoptosis assay, cells were plated in 24-well plates (Corning, Cat. 3524) at 200000 cells/well/cell line.

2. Reagents

The sources of the reagents used in this experiment are as follows: RPMI 1640 basal medium (Gibco, Cat. C11875500BT), IMDM basal medium (Gibco, Cat. C12440500BT), penicillin-streptomycin (Gibco, Cat. 15140122), fetal bovine serum (AUSGENEX, Cat. FBSSA500-S), dimethyl sulfoxide (Sigma, Cat. D8418), ACK lysis buffer (Life Technologies, Cat. A1049201), apoptosis test kit (BD, Cat. 556547), RIPA cell lysis buffer (Beyotime, Cat. P0013B), PMSF (YEASEN, Cat. 20104ES08), BCA protein concentration quantification kit (Beyotime, Cat. P0012), protease inhibitors (YEASEN, Cat. 20124ES10), phosphatase inhibitors (YEASEN, Cat. 20109ES05), 4-20% SDS-PAGE-precast gel (GenScript®, Cat. M42010M), PVDF Transfer Film (Millipore, Cat. IPVH00010), BSA (Bovine Serum Albumin) (GENVIEW, Cat. FA016-250), CellTiter-Glo® Luminescence cell viability detection kit (Promega, Cat. G7571), 20×TBS (Sangon Biotech., Cat. B548105-0500), enhanced ECL chemiluminescence detection kit (YEASEN, Cat. 36222ES76), anti-MCL-1 (Y37) antibody (Abcam, Cat. Ab186822), anti-BIM antibody (Abcam, Cat. Ab32158), anti-PUMA antibody (Abcam, Cat. Ab186917), anti-BAK antibody (Abcam, Cat. Ab220790), PARP-1 antibody (CST, Cat. 9532S), beta-actin (CST, Cat. 3700S), MCL-1 antibody (CST, Cat. 94296S), MYC antibody (CST, Cat. 13987T), Caspase-3 antibody (CST, Cat. 9665S), anti-GAPDH antibody (CST, Cat. 2118s), goat anti-rabbit-HRP (YEASEN, Cat. 33101ES60), and goat anti-mouse-HRP (YEASEN, Cat. 33201ES60), Annexin V-PI (propidium iodide) staining kit (BD, Cat. #556547).

3. Test Samples

The test sample stock solutions were prepared using the solvents listed in Table 2. The stock solutions have a concentration of $10^{-2}$M, and can be stored at −20° C. in dark for use. The stock solutions were diluted to the desired working concentration using serum-free medium as diluent.

TABLE 2

Test samples and preparation of stock solutions

| | Compounds | MW | Solvent | Sources |
|---|---|---|---|---|
| 1 | Compound 6 | 882.3 | DMSO | Prepared as described in WO2018/027097 |
| 2 | Homoharringtonine | 545.62 | DMSO | MCE (MedChemExpress LLC) |

4. Instrument

The instruments used in the tests include: Biosafety Cabinets (ESCO, Model AC2-4S1); $CO_2$ incubator (ESCO, Model CLM-170B-8-NF); Inverted microscope (COIC INDUSTRIAL, Model: XDS-1B); Smafy Electric Suction Apparatus (Shanghai Baojia Medical Instruments Limited, Model YX 930D); balance (Mettler-Toledo, AB135-S); low speed centrifuge (Shanghai Lu Xiangyi Centrifuge Instrument Co. Ltd, Model L600); ELIASA/microplate reader (Bio-Tek, Model: Synergy H1); 10 μL, 20 μL, 100 μL, 200 μL, 1000 μL Single Channel Pipettes (Eppendorf); Multichannel Pipettes (Eppendorf); Pipette Controller (INTEGRAPIPETBOY2, 155000 classic); Thermostat water bath (Shanghai YiHeng Science Instruments Co., Ltd., DK-8AX); Vortex oscillator (Haimen Qilin-Beier Instrument Manufacture Co., LTD, Kylin-Bell 5); Sterilization pot (Shanghai ShenAn Medical Instruments Co., Ltd., LDZM-60KCS); Chemiluminescence imager (Azure Biosystems, Model: Azure c300); Flow cytometer (Life technology, Model: Attune NxT); Ultra-sensitive Factor Electrochemiluminescence Analyzer (Meso Scale Discovery, Model: SECTOR S600).

5. Method for Analyzing Effect of Combined Medication

For combination tests, the results were further analyzed using the CalcuSyn program to calculate a Combination Index (CI) (Chou, T. C. (2010) "Drug combination studies and their synergy quantification using the Chou-Talalay method.", Cancer Res 70(2): 440-446). Calcusyn is a professional mixed drug analysis software, and the Calcusyn software can be used for accurately analyzing the combined drug effect and quickly calculating and analyzing the interaction of various drugs, including synergistic effect, addition effect, antagonistic effect and the like. The CI value of less than 1 for the combination of two drugs indicates that the combination has synergistic effect; CI value=1 indicates that the two drugs in combination have an additive effect; CI values>1 indicates that the combination is antagonistic.
CI (Joint Index):
  <0.1: 5+ very strong
  0.1-0.3: 4+ strong
  0.3-0.7: 3+ medium
  0.7-0.85: 2+ relatively mild
  0.85-0.90: 1+ mild Example 1: Synergistic Antiproliferative Effect of the Combination of Compound 6 and Homoharringtonine

[Experimental Methods]: CellTiter-Glo® Luminometric Cell Viability Assay (CTG Experiment)

The anti-proliferation effects of the test sample in three AML/MDS cell lines, namely MV-4-11 (Compound 6 sensitive cell line), OCI-AML-3 (Compound 6 non-sensitive cell line) and SKM-1 (Compound 6 non-sensitive cell line), were determined by quantifying ATP using CellTiter-Glo luminescence cell viability detection kits, according to the manufacturer's instructions.

First, cells in the logarithmic growth phase were collected, centrifuged, and the cell suspension was counted and diluted/adjusted to the desired concentration. After mixing, 90 μL of cell suspension were added to each well of a 96-well plate at $10 \times 10^3$ cells/well, and the cells were incubated in an incubator at 37° C. under 5% $CO_2$ for 2 hours. More than 3 blank control wells containing only medium (100 μL/well) without cells were set on the same plate to obtain background luminescence, and cell control wells, i.e., wells containing cells but treated with vehicle control, were set.

Based on the sensitivity of different cells to different drugs, the appropriate initial highest concentration was chosen, and serial dilutions were made in a 1:3 ratio to give 7 serial concentrations. 2 test samples were added to each well at 5 L/well, and the final concentration of drug tested in each well is shown on the abscissa of FIG. 1. The plates were incubated at 37° C. in a 5% $CO_2$ incubator for 24 hours. Duplicate wells were made for each concentration tested. Cell growth was observed daily under an inverted microscope.

Upon the completion of the culture, the 96-well plate and the contents were taken out of the incubator, balanced to room temperature at rt, adding 30 μL of CellTiter-Glo reagents into each well (in dark). The 96-well plate was placed on an orbital shaker to mix contents 2 minutes, allowing sufficient cell lysis; and the 96-well plate was incubated at room temperature for 10 minutes to stabilize the fluorescence signal.

Luminescence signals were detected using a Biotek synergy H1 microplate reader. Using the average fluorescence signal values of 2 replicate wells, the percent cell viability was calculated by the following formula:

Percent cell viability (%)=(fluorescence signal value of test well−fluorescence signal value of blank control well)/(fluorescence signal value of cell control well−fluorescence signal value of blank control well)×100%

[Experimental Results]

The results show that, the profile of the combination shifts to the left as compared to the profile for Compound 6 and HHT alone, suggesting that Compound 6 has enhanced antiproliferative effects in all AML/MDS cell lines tested. Combination efficacy analysis shows a combination index (CI value) of less than 0.1 at multiple combination concentrations, indicating that Compound 6 in combination with HHT has a synergistic antiproliferative effect in all AML/MDS cell lines tested. The specific CI values and the original dose-effect growth inhibition curves for Compound 6 in combination with HHT are detailed in FIG. 1.

Example 2: Synergistic Apoptosis Inducing Effect of Compound 6 and Homoharringtonine

[Experimental Methods]: Flow Cytometer Analysis

Cells were harvested after 24 hours of treatment with Compound 6 alone, HHT alone, or the combination of both, and washed once with phosphate buffered saline (PBS). Cells were stained with Annexin-V and PI and analyzed using an Attune NxT flow cytometer. Apoptosis profiles were obtained by analyzing 20000 cells per experimental condition.

Apoptosis was detected using Annexin V-PI (propidium iodide) staining kit according to the manufacturer's instructions. After treating the cells MV-4-11, OCI-AML-3 and SKM-1 with 10 nM Compound 6 alone, 10 nM or 30 nM HHT alone or the combination of both for 24 hours, the cells were harvested and washed once with PBS. Cells were bi-color stained with Annenix V-FITC and PI. After staining was complete, analysis was performed using an Attune NxT flow cytometer. Apoptosis profiles were obtained by analyzing 20000 cells per experimental condition.

[Experimental Results]

Figure 2:
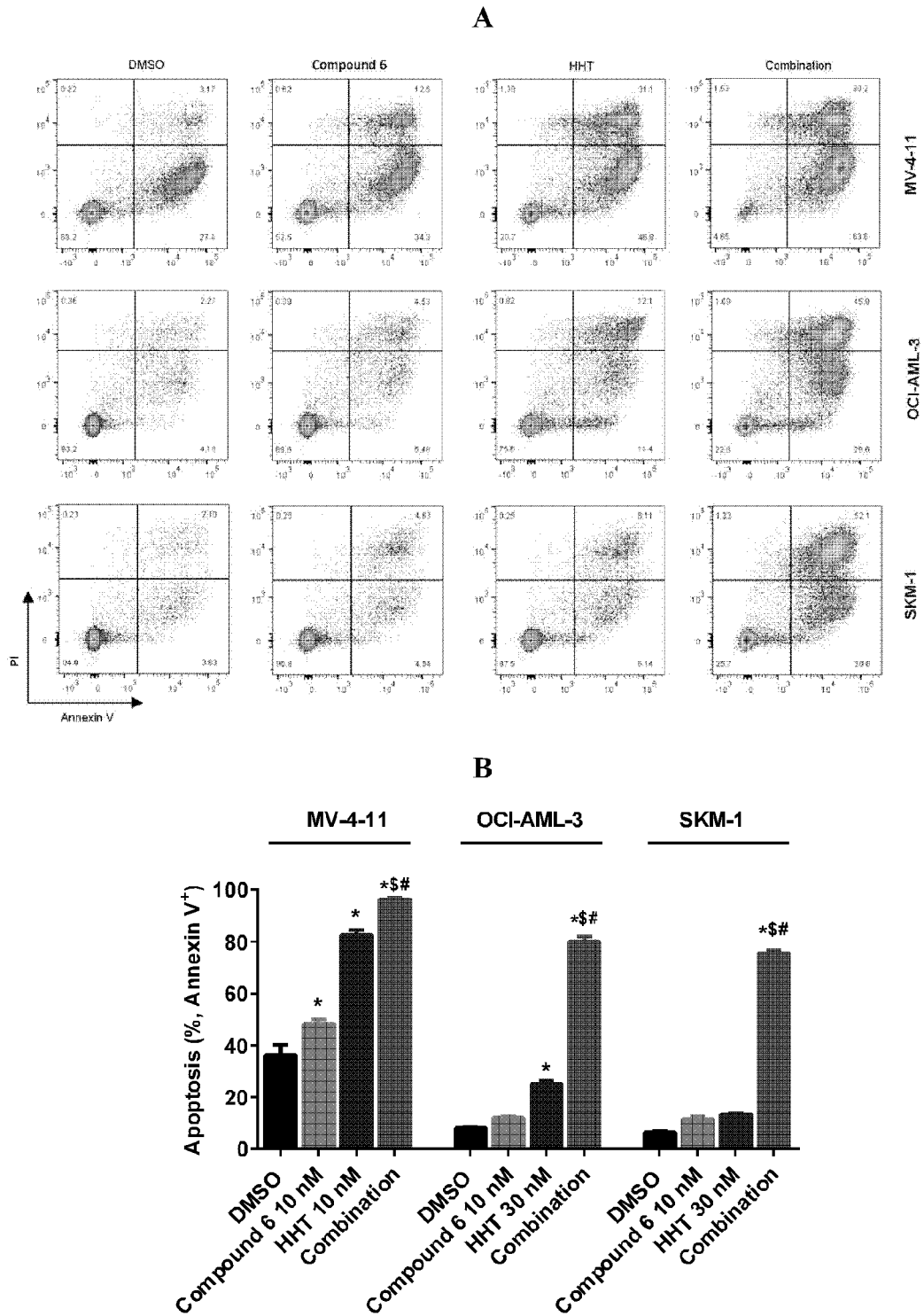

The results are shown in FIG. 2, Compound 6 and HHT administered alone induce certain apoptosis in the AML cell lines tested, as compared with the vehicle control DMSO. However, the combination significantly increases the proportion of apoptosis. For example, in OCI-AML-3 cells, Compound 6 (10 nM) and HHT (30 nM) alone induce 12.1% and 25.0% apoptosis, respectively, while the combination of both induces 80.1% apoptosis, statistically and significantly differing from the DMSO group and each drug alone. The detection results in MV-4-11 and SKM-1 cells also show that the combination of Compound 6 and HHT can remarkably induce apoptosis, with statistically significant difference from the vehicle control group and each single drug group. The apoptosis profiles and data statistics are detailed in FIG. 2.

Example 3: Compound 6 in Combination with Homoharringtonine Significantly Reduces Levels of Proto-Oncoproteins MYC and MCL-1 and Enhances Expression of Apoptosis Markers

[Experimental Methods]: Western Blot Assay

Western Blot assay was performed after 4 hours treatment of cells in logarithmic growth phase with Compound 6, HHT, either alone or in combination.

After 4 hours of interaction with 10 nM Compound 6 in combination with 10 nM or 30 nM HHT, cells were harvested and washed once with pre-cooled PBS. The cell pellets were lysed using RIPA lysate containing 1% PMSF and 1% protease inhibitor. The protein concentration was detected by using a BCA protein concentration detection kit. Cell lysates (20-50 μg) were separated by 4-20% SDS-PAGE. The separated proteins were transferred to PVDF membranes which were blocked using 1% BSA (bovine serum albumin) buffer at room temperature for 1 hours before incubated in a shaker at 4° C. overnight with primary antibody diluted in 1×TBST (Tris-Buffered Saline Tween-20) containing 1% BSA. The membranes were washed 3 times with 1×TBST each for 10 minutes, and then were incubated for 1 hour at room temperature using horseradish peroxidase (HRP)-tagged secondary antibodies (goat anti-rabbit-HRP (Yeasen, Cat. #33101ES60) and goat anti-mouse-HRP (Yeasen, Cat. #33201ES60), diluted according to the manufacturer's instructions). The membranes were washed 3 times with 1×TBST each for 10 minutes. HRP substrate was added onto the PVDF membrane. ECL hypersensitivity reagents (enhanced ECL chemiluminescence detection kit) were used to generate the signal. The signal intensity directly reflects the protein expression level.

[Experimental Results]

Figure 3:
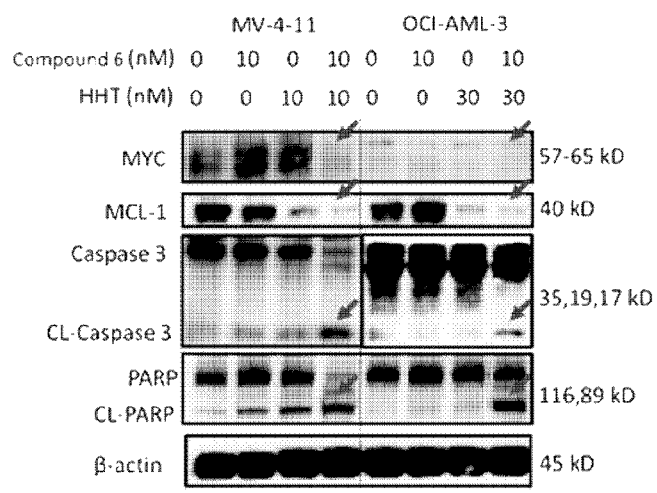
Figure 3:
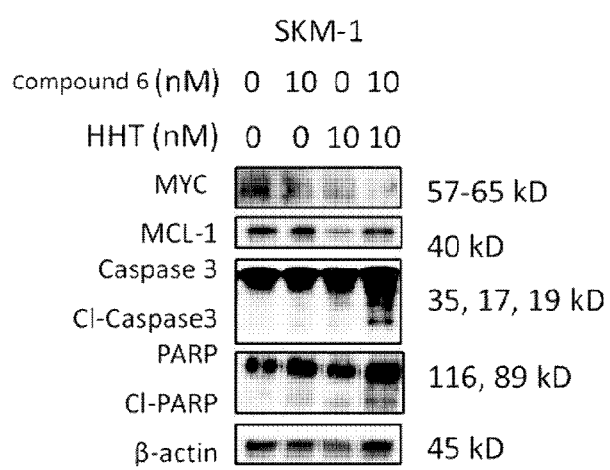

Western Blot results are shown in FIG. 3. In MV-4-11, OCI-AML-3 and SKM-1 cell lines, both HHT single drug group and the combined Compound 6 and HHT group can reduce the expression level of anti-apoptosis protein MCL-1, and particularly, significant difference is shown in MV-4-11. In the combined Compound 6 and HHT group, the expressions of the cleaved Caspase 3 (CL-Caspase) and the cleaved PARP-1 (CL-PARP) are significantly enhanced, which indicates that the combination of the two synergistically can induce the apoptosis. Meanwhile, in the three cell lines, the combined Compound 6 and HHT also significantly reduces the proto-oncoprotein MYC.

Example 4: Compound 6 in Combination with Homoharringtonine Interferes BCL-2:BIM, MCL-1:BAK and MCL-1:PUMA Complexes

[Experimental Methods]: MSD (Meso Scale Discovery) Method

The apoptosis-related protein complexes were detected by MSD electrochemical luminescence method after 4 hours treatment of cells in logarithmic growth phase with Compound 6, HHT, either alone or in combination.

The MSD method was performed to detect BCL-2:BIM, MCL-1:PUMA and MCL-1:BAK protein complexes. The AML/MDS cell lines were treated by Compound 6 or in combination with HHT for 4 hours, harvested, and then proteins were extracted with weak protein lysate (RIPA lysate, Beyotime, P0013D) and the concentration was adjusted to 1 mg/mL for use. Streptavidin-coated 96-well plates were blocked overnight with 150 μL of blocking solution (MesoScale Discovery, R93AA-2). The anti-BCL-2 antibody and the anti-MCL-1 protein were labeled with Sulfo-Tag (Sulfo-Tag NHS ester, MesoScale Discovery, R91AO-1); the anti-BIM, anti-PUMA and anti-BAK antibodies were labeled with biotin. 50 μL (1 g/mL) of biotin-labeled anti-BIM antibody, anti-PUMA antibody or anti-BAK antibody was added to the streptavidin-labeled plates, and after 1 hour of incubation, the plates were washed three times with PBS containing 0.5% Tween-20. Then 50 μg of cell lysate was added and incubated for 1 hour. After incubation, the plates were washed three times with PBS containing 0.5% Tween-20. Antibodies were then detected by incubating with Sulfo-tag labeled MCL-1 or BCL-2 (4 g/mL) for 60 minutes. The electroluminescent signal intensity was detected on a Meso Scale Discovery Sector S600.

[Experimental Results]

Figure 4:
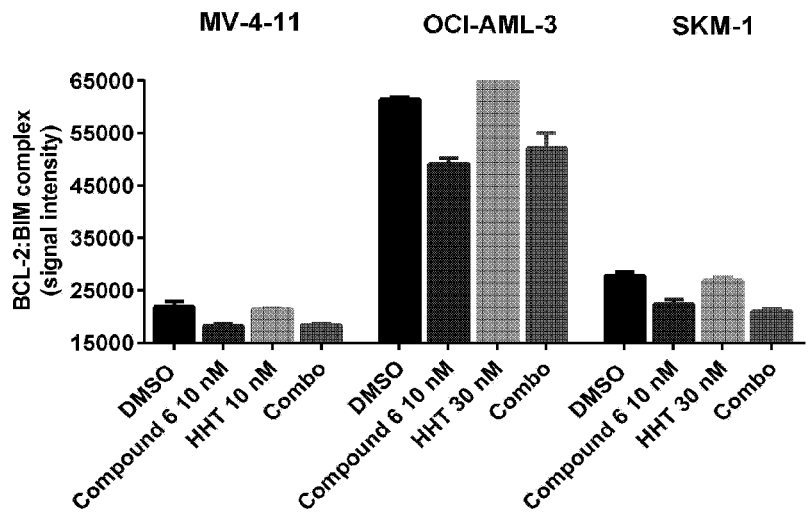
Figure 4:
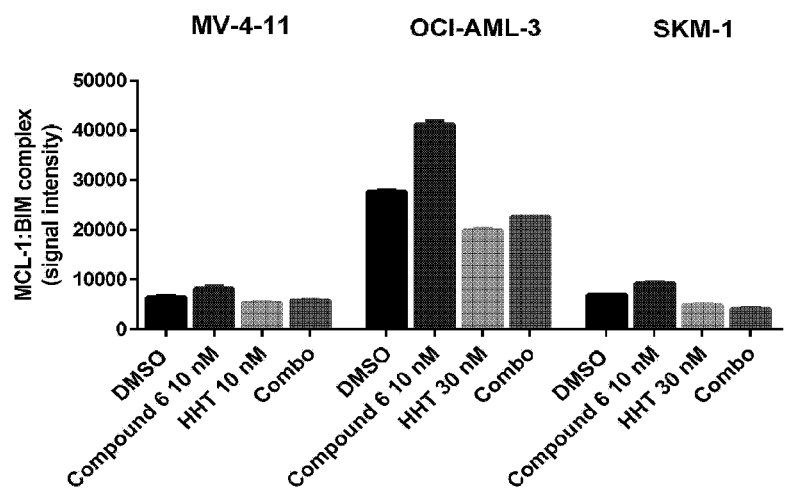
Figure 4:
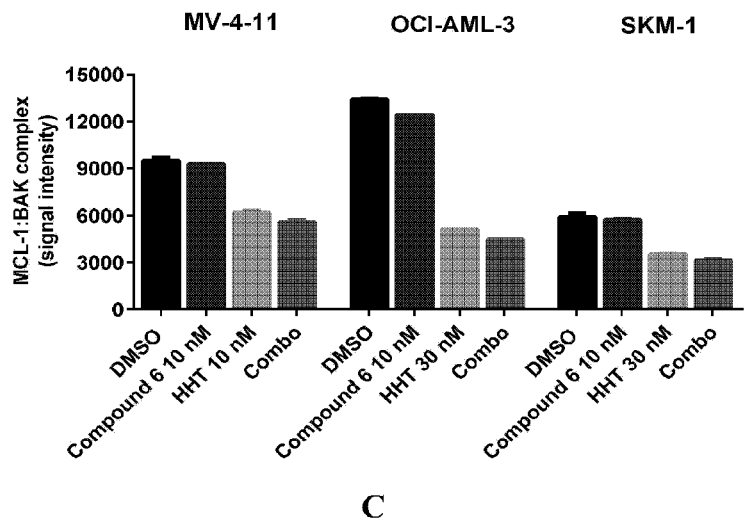
Figure 4:
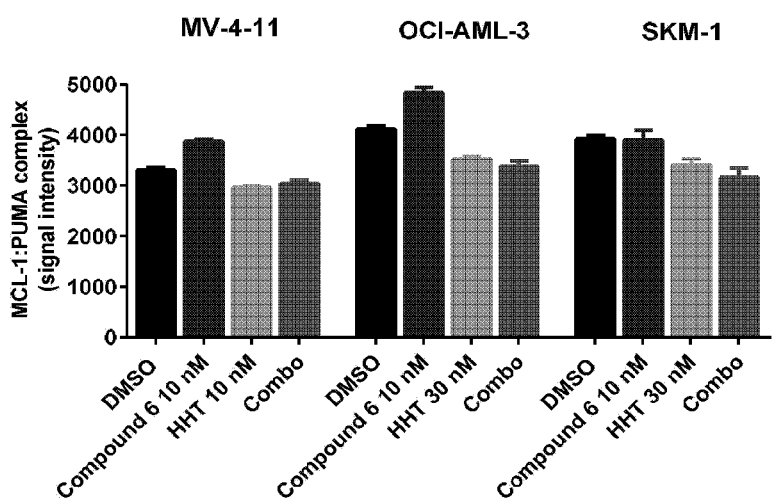

MSD results are shown in FIG. 4. After the cells are treated by Compound 6, the expression level of BCL-2:BIM complex is reduced, confirming that Compound 6 can antagonize the association of BCL-2 and BIM, inhibit the anti-apoptosis function of BCL-2 and release pro-apoptotic protein BIM. The significant reduction of MCL-1:BIM complex in the group treated with the combination of Compound 6 and HHT as compared with the group treated with Compound 6 alone, demonstrates that the combination of Compound 6 and HHT can simultaneously reduce BCL-2:BIM and MCL-1:BIM complexes, thereby releasing the pro-apoptotic protein BIM (FIGS. 4A and 4B).

As shown in FIG. 4C, the MCL/BAK complex in the group of the combination of Compound 6 and HHT is significantly reduced as compared with the control group and Compound 6 group, suggesting that Compound 6 in combination with HHT releases the pro-apoptotic protein BAK. As shown in FIG. 4D, the MCL-1:PUMA complex is also reduced to certain extent in the group of the combination of Compound 6 and HHT, as compared with the control and the single drug group, suggesting that Compound 6 in combination with HHT can release the pro-apoptotic protein PUMA.

Taken together, Compound 6 in combination with HHT can release more pro-apoptotic proteins BIM, BAK and PUMA.

Example 5: Synergistic Anti-Tumor Activity of Compound 6 in Combination with Homoharringtonine in Human MV-4-11 AML Xenograft Model in Mice In the above cell-based assays in vitro, MV-4-11 cells have shown as one of human AML cell lines having moderate sensitivity to Compound 6. This study thus established an xenograft tumor model in mice with human MV-4-11 cells to assess the anti-tumor activity of Compound 6 in combination with HHT.

[Experimental Methods]

MV-4-11 AML xenograft models were established by subcutaneously injecting MV-4-11 tumor cells ($10 \times 10^6$ cells+Matrigel gel/animal) into the right flank of the female BALB/c Nude mice (Supplier: Lingchang, SCXK (Shanghai) 2018-0003; Certificate number: 20180003004157) under the sterile condition. When the tumors reached an appropriate size (125 mm$^3$), mice were randomized into 6 groups: vehicle control, Compound 6 (50 mg/kg), positive control ABT-199 (50 mg/kg) (Batch number: K01-131-2; Jiangsu Aikon Biopharmaceutical R&D Co., Ltd), HHT (1 mg/kg), Compound 6 in combination with HHT treatment group and ABT-199 in combination with HHT treatment group. Treatment was initiated on the day of grouping (Day 1). Compound 6 and ABT-199 were orally administered once daily for consecutive 21 days. HHT was intraperitoneally administered once daily for consecutive 14 days. The tumor sizes (caliper) and animal body weights were measured twice a week.

[Experimental Results]

With the relative tumor volume (RTV) as measured above, the relative tumor proliferation rate T/C (%) was calculated according to the following formula:

$$T/C = T_{RTV}/C_{RTV} \times 100\%,$$

wherein $T_{RTV}$ is RTV for treatment groups; $C_{RTV}$ is RTV for vehicle control group; the evaluation criteria are: T/C (%)>40% is ineffective; T/C (%) less than or equal to 40% with statistical p<0.05 is effective.

Figure 5:
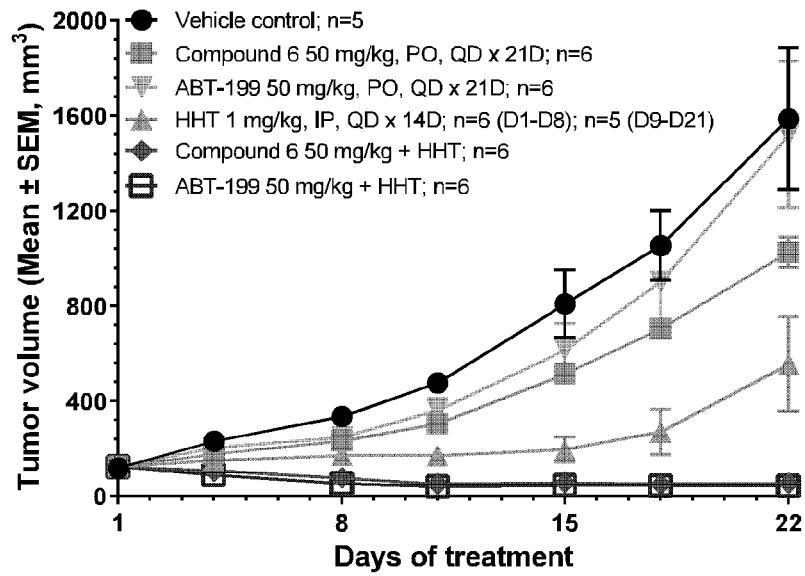
FIG. 5 shows the synergistic anti-tumor effects of compound 6 combination with HHT in subcutaneous MV-4-11 AML xenografts (Study No. SZ-EF-30-2018). (A) Tumor growth curve, (B) body weight change (%).
Figure 5:
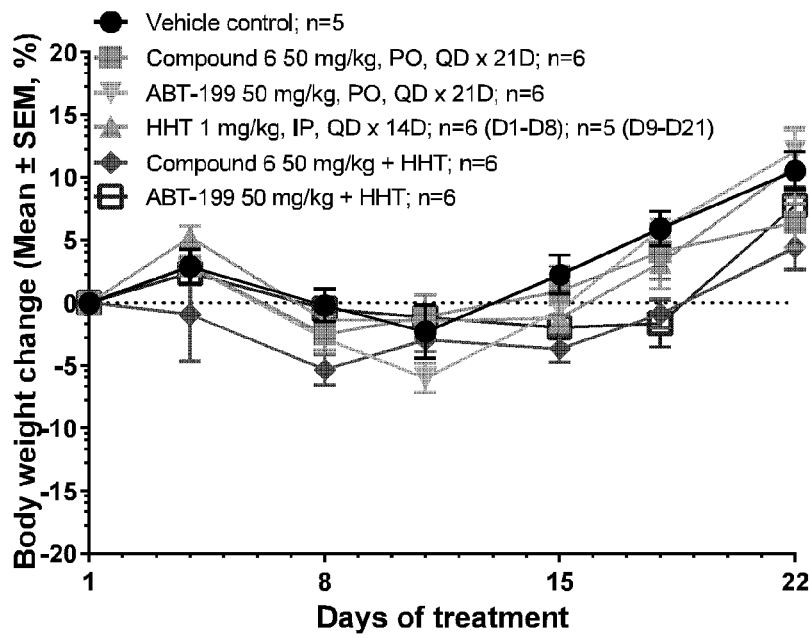

As shown in FIGS. 5A and 5B, the treatment with Compound 6 at 50 mg/kg or ABT-199 at 50 mg/kg demonstrated no antitumor activity in MV-4-11 xenograft model, resulting in T/C values of 62.76% (p>0.05, vs. vehicle control) and 88.27% (p>0.05, vs. vehicle control), respectively. Treatment with HHT at 1 mg/kg demonstrated moderate antitumor activity with a T/C value of 32.43% (p>0.05, vs. vehicle control) with 3/5 SD. The combination treatment of Compound 6 and HHT exhibited significant synergistic anti-AML activity, achieved a T/C value of 3.31% (p<0.05, vs. vehicle control; p<0.01, vs. Compound 6 group) with a synergy ratio of 6.14 and a remission rate of 100% (6/6 PR). In parallel, another FDA-approved BCL-2 inhibitor ABT-199 (venetoclax, 50 mg/kg) in combination with HHT (1 mg/kg) also exhibited significant synergistic anti-AML activity, achieving a T/C value of 2.59% (p<0.05, vs. vehicle control; p<0.01, vs. ABT-199 group) with a synergy ratio of 11.07 and a remission rate of 100% (6/6 PR). In contrast, no CR or PR occurred in Compound 6 or ABT-199 single arm. These results demonstrated that Compound 6 in combination with HHT has significant anti-AML effect equivalent with that of ABT-199 in combination with HHT. No obvious body weight loss was observed under all treatments (FIG. 5B), indicating good tolerance for the above dosing regimen.

TABLE 3

| Treatment | RTV (D22) (Mean ± SEM) | T/C (%) (D22) | Synergy ratio$^a$ | mRECIST |
|---|---|---|---|---|
| Vehicle control | 13.33 ± 2.40 | — | — | 6/6 PD |
| Compound 6 50 mg/kg | 8.36 ± 0.76 | 62.76 | — | 6/6 PD |
| ABT-199 50 mg/kg | 11.77 ± 1.94 | 88.27 | — | 6/6 PD |
| HHT 1 mg/kg | 4.32 ± 1.42 | 32.43 | — | 3/5 SD, 2/5 PD |
| Compound 6 + HHT | 0.44 ± 0.04*## | 3.31 | 6.14 | 6/6 PR |
| ABT-199 + BHT | 0.34 ± 0.02*$$ | 2.59 | 11.07 | 6/6 PR |

*p < 0.05, vs. vehicle contro group;
p < 0.01, vs. Compound 6 group;
$$p < 0.01, vs. ABT-199 group;
$^a$Ratio > 1, synergistic; Ratio = 1, additive; Ratio < 1, antagonistic.
mRECIST (modified Response Evaluation Criteria in Solid Tumors):
CR: complete remission;
PR: partial remission;
SD: stable diseases;
PD: progression of diseases The results suggest that Compound 6 combined with HHT exerts synergetic antitumor activity in AML xenograft models, indicating the potential therapeutic application of this combination in treating AML patients.

Example 6: Synergistic Anti-Tumor Activity of Compound 6 in Combination with Homoharringtonine (HHT) in Human OCI-AML-3 AML Xenograft Models in Mice It has been shown that tumor cells highly expressing anti-apoptotic protein MCL-1 such as OCI-AML-3 cell, exhibit primary resistance to BCL-2 selective inhibitor (ABT-199) treatment (Pan et al., 2017, Cancer cell. 32(6), 748-760 e746). This study thus used OCI-AML-3 cells to establish an SC xenograft model in mice, in order to investigate whether Compound 6 in combination with HHT can overcome the primary resistance of AML for Compound 6 induced by high expression of MCL-1.

[Experimental Methods]

OCI-AML AML xenograft models were established by subcutaneously injecting $1 \times 10^6$ cells/animal OCI-AML-3 cells into the right flank of the female NOD SCID mouse (Supplier: Vital River Laboratories, SCXK (BeiJing) 2016-0006; Certificate number: 1100111911056971) under the sterile condition. When the tumors reached an appropriate size (133 mm$^3$), mice were randomized into 4 groups:

vehicle control, Compound 6 (50 mg/kg), HHT (0.75 mg/kg) and Compound 6 in combination with HHT treatment group. Treatment was initiated on the grouping day (D1). Compound 6 was orally administered once daily for consecutive 14 days. HHT was intraperitoneally injected once daily from D2 and continued for consecutive 7 days. The tumor sizes (caliper) and animal body weights were measured twice a week.

[Experimental Results]

T/Cs (%) were determined as described in the above Example 5.

Figure 6:
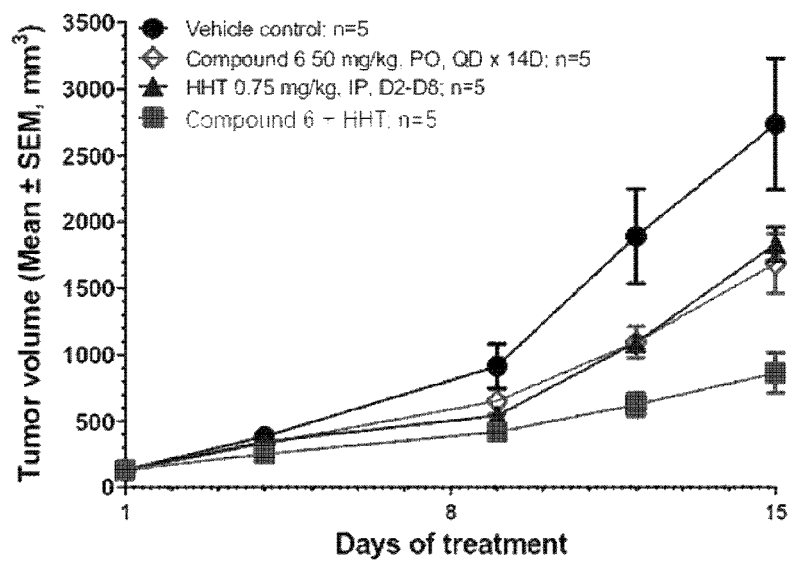
FIG. 6 shows the synergistic anti-tumor effects of compound 6 combination with HHT in subcutaneous OCI-AML-3 AML xenografts (Study No. SZ-EF-69-2019). (A) Tumor growth curve, (B) body weight change (%).
Figure 6:
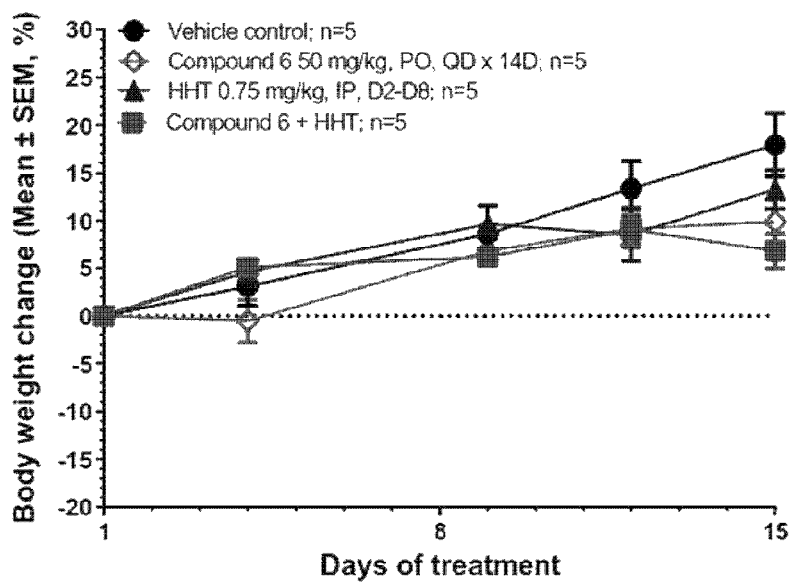

As shown in FIGS. 6A and 6B, OCI-AML-3 exhibited as a fast-growing xenograft tumor; animals of vehicle control were euthanized due to their tumor sizes exceeding the range allowed for animal welfare, and the study thus was terminated on D15. During the 15 days of treatment, Compound 6 single arm at 50 mg/kg failed to exhibit significant anti-tumor activity as expected, resulting in T/C value of 61.36% (p>0.05, vs. vehicle control); the treatment with HHT at 0.75 mg/kg also demonstrated no significant anti-tumor activity with a T/C value of 66.77% (p>0.05, vs. vehicle control). Importantly, the combination treatment of Compound 6 and HHT exhibited significant synergistic antitumor activity, achieved a T/C value of 33.02% (p<0.05, vs. vehicle control) with a synergy ratio of 1.24. No obvious body weight loss was observed under all treatments (FIG. 6B), indicating good tolerance for the above dosing regimen.

TABLE 4

| Treatment | RTV(D15) (Mean ± SEM) | T/C (%) (D15) | Synergy ratio$^a$ |
|---|---|---|---|
| Vehicle control | 20.81 ± 4.01 | — | — |
| Compound 6 50 mg/kg | 12.77 ± 1.51 | 61.36 | — |
| EMT 0.75 mg/kg | 13.89 ± 0.82 | 66.77 | — |
| Compound 6 + HHT | 6.87 ± 1.60* | 33.02 | 1.24 |

*p < 0.05, vs. vehicle controlgroup;
$^a$Ratio > 1, synergistic; Ratio = 1, additive; Ratio < 1, antagonistic.

The results suggest that the combination of Compound 6 with HHT exerts highly synergistic antitumor activities, and sensitizes resistance models to cell killing, providing a new combination strategy for a more effective therapy for AML patients.

The invention claimed is:

1. A combination product for the treatment of acute myeloid leukemia (AML) or myelodysplastic syndrome (MDS) comprising a Bcl-2/Bcl-xL inhibitor and a chemotherapeutic agent, wherein the Bcl-2/Bcl-xL inhibitor is a compound having the following formula:

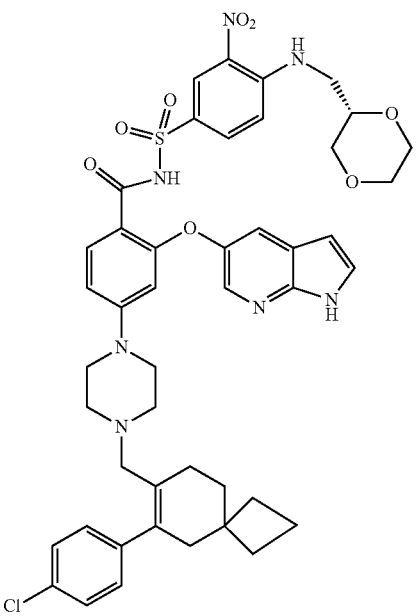 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt thereof;
wherein the chemotherapeutic agent is homoharringtonine or a pharmaceutically acceptable salt thereof.

2. The combination product according to claim 1, wherein the combination product is in the form of a pharmaceutical composition, optionally comprising a pharmaceutically acceptable carrier, diluent or excipient; or the Bcl-2/Bcl-xL inhibitor and the chemotherapeutic agent are each in separate formulations.

3. The combination product according to claim 2 wherein the Bcl-2/Bcl-xL inhibitor and the chemotherapeutic agent each in separate formulations are administered simultaneously or sequentially.

4. The combination product according to claim 1, wherein the combination product is in the form of tablets, capsules, granules, syrups, powders, lozenges, sachets, cachets, elixirs, suspensions, emulsions, solutions, syrups, aerosols, ointments, creams and injections.

5. A method of treating, reducing the frequency of symptoms of, or delaying the onset of symptoms of acute myeloid leukemia (AML) or myelodysplastic syndrome (MDS) in a patient in need thereof comprising administering a combination product according to claim 1.

6. The method according to claim 5, wherein the acute myeloid leukemia (AML) or myelodysplastic syndrome (MDS) is resistant to chemotherapy.

7. The method according to claim 5, wherein the Bcl-2/Bcl-xL inhibitor or pharmaceutically acceptable salt thereof in the combination product is administered in an amount of about 0.0025-1500 mg/day.

8. The method according to claim 5, wherein the chemotherapeutic agent or a pharmaceutically acceptable salt thereof in the combination product is administered in an amount of from about 0.005 mg/day to about 1000 mg/day.

* * * * *